(12) United States Patent
Shi

(10) Patent No.: US 7,153,971 B2
(45) Date of Patent: Dec. 26, 2006

(54) COMPOUNDS CONTAINING OXAZOLIDINONE MOIETY AND USES THEREOF

(75) Inventor: Yian Shi, Fort Collins, CO (US)

(73) Assignee: Colorado State University Research Foundation, Ft Collins, CO (US)

( * ) Notice: Subject to any disclaimer, the term of this patent is extended or adjusted under 35 U.S.C. 154(b) by 72 days.

(21) Appl. No.: 10/343,302

(22) PCT Filed: Aug. 28, 2001

(86) PCT No.: PCT/US01/27069

§ 371 (c)(1),
(2), (4) Date: Jul. 15, 2003

(87) PCT Pub. No.: WO02/18391

PCT Pub. Date: Mar. 7, 2002

(65) Prior Publication Data

US 2004/0039209 A1 Feb. 26, 2004

Related U.S. Application Data

(60) Provisional application No. 60/228,552, filed on Aug. 28, 2000.

(51) Int. Cl.
- C07D 263/62 (2006.01)
- C07D 301/12 (2006.01)
- C07D 413/02 (2006.01)
- C07D 498/10 (2006.01)
- C07D 498/20 (2006.01)

(52) U.S. Cl. .................. 548/216; 549/525; 549/531; 502/172

(58) Field of Classification Search .............. 548/216; 549/525, 531; 502/172
See application file for complete search history.

(56) References Cited

U.S. PATENT DOCUMENTS 5,902,814 A 5/1999 Gordon et al.
6,107,036 A 8/2000 Heindl et al.

OTHER PUBLICATIONS

Wang Z. et al., "An Efficient Catalytic Asymmetric Epoxidation Method," Journal of the American Chemical Society, American Chemical Society, Washington, D.C., U.S., vol. 119, pp. 11224-11235, 1997.
Tian H. et al., "Highly Enantioselective Epoxidation of cis-Olefins by Chiral Dioxirane," Journal of the American Chemical Society, American Chemical Society, Washington, D.C., U.S., vol. 122, No. 46, pp. 11551-11552, 2000.

*Primary Examiner*—Taofiq Solola
(74) *Attorney, Agent, or Firm*—Faegre & Benson LLP

(57) ABSTRACT

A compound and method for producing an enantiomerically enriched epoxide from an olefin using a chiral ketone and an oxidizing agent is disclosed. In particular, the compound is of the formula: I wherein $R^1$, $R^2$, $R^3$ and $R^4$ are those defined herein

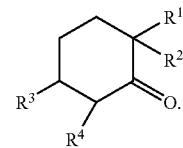

(I)

29 Claims, 2 Drawing Sheets

US 7,153,971 B2

COMPOUNDS CONTAINING OXAZOLIDINONE MOIETY AND USES THEREOF

This appln. claims the benefit of prov. appln. 60/228,552 filed on Aug. 28, 2000.

STATEMENT AS TO RIGHTS TO INVENTIONS MADE UNDER FEDERALLY SPONSORED RESEARCH AND DEVELOPMENT

The U.S. Government has a paid-up license in this invention and the right in limited circumstances to require the patent owner to license others on reasonable terms as provided for by the terms of Grant No. GM-59705 awarded by the National Institutes of Health.

FILED OF THE INVENTION

The present invention is directed to a chiral ketone and methods for using the same. In particular, the present invention is directed to using the chiral ketone and an oxidizing agent to epoxidize olefins.

BACKGROUND OF THE INVENTION

Epoxides are very important chiral building blocks for the synthesis of enantiomerically pure complex molecules. Asymmetric epoxidation of olefins presents a powerful strategy for the synthesis of enantiomerically enriched epoxides.

Among many epoxidation methods, chiral dioxiranes generated ill situ from an oxidizing agent and a chiral ketone have appeared to be promising reagents for asymmetric epoxidations. Since the first asymmetric epoxidation of olefins with dioxirane were reported in 1984, significant progress has been made in the area. A variety of cyclic chiral ketones have been used as catalysts to achieve enantioselectivity for the epoxidation of olefins.

However, there is a still need for an inexpensive, readily available, and general asymmetric epoxidation catalyst which can epoxidize a variety of olefins, in particular for cis and terminal olefins, with high enantioselectivity.

SUMMARY OF THE INVENTION

One aspect of the present invention provides a compound of the formula:

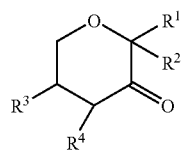

where one of $R^1$ and $R^2$ is —$OR^a$ and the other is -alkylene-$OR^b$, where each of $R^a$ and $R^b$ is independently a non-ring forming hydroxy protecting group, or $R^1$ and $R^2$ together with the carbon atoms to which they are attached to form an optionally substituted heterocyclyl; and each of $R^3$ and $R^4$ is independently hydrogen or —$OR^c$, where $R^c$ is a non-ring forming hydroxy protecting group, or $R^3$ and $R^4$ together with the carbon atoms to which they are attached to form an optionally substituted heterocyclyl, provided at least one of $R^1$ and $R^2$ together with the carbon atoms to which they are attached to or $R^3$ and $R^4$ together with the carbon atoms to which they are attached to form an optionally substituted nitrogen atom containing heterocyclyl.

In one embodiment, Compound of Formula I is used to produce an asymmetric epoxide from an olefin in the presence of an oxidizing agent.

Another aspect of the present invention provides, a method for producing a spiro-bicyclic compound of the formula:

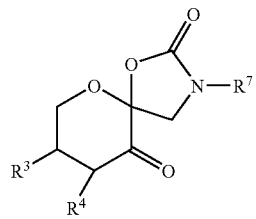

wherein each of $R^3$ and $R^4$ is independently hydrogen or —$OR^c$, where $R^c$ is a non-ring forming hydroxy protecting group, or $R^3$ and $R^4$ together with the carbon atoms to which they are attached to form an optionally substituted heterocyclyl; and $R^7$ is selected from the group consisting of hydrogen, alkyl, aryl, —$(R^8)_n$—$C(=O)$—$R^9$, and other nitrogen protecting group, where n is 0 or 1, $R^8$ is alkylene, and $R^9$ is hydroxy, alkyl, alkoxy, —$NR^aR^b$ (where $R^a$ and $R^b$ is independently hydrogen or alkyl), aryl and aryloxy; said method comprising:
 (a) contacting a carbohydrate with an amine under condition sufficient to produce an amino tetrahydroxy carbohydrate;
 (b) protecting two hydroxy groups by contacting the amino tetrahydroxy carbohydrate with a hydroxy protecting group under conditions sufficient to produce a dihydroxy-protected amino dihydroxy carbohydrate;
 (c) forming a heterocyclic moiety by contacting the dihydroxy-protected amino dihydroxy carbohydrate with an activated carbonate under conditions sufficient to produce a hydroxy spiro-bicyclic compound; and
 (d) oxidizing the hydroxy group contacting the hydroxy spiro-bicyclic compound with an oxidizing agent under conditions sufficient to produce the spiro-bicyclic compound of Formula IA.

Preferably, the spiro-bicyclic compound is enantiomerically enriched chiral compound. More preferably, the enantiomerically enriched spiro-bicyclic compound is of the formula:

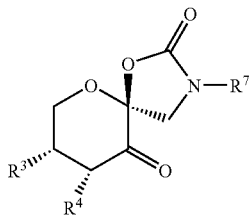

or stereoisomers thereof, where $R^3$, $R^4$ and $R^7$ are those defined herein. And most preferably, the enantiomerically enriched spiro-bicyclic compound is of the formula:

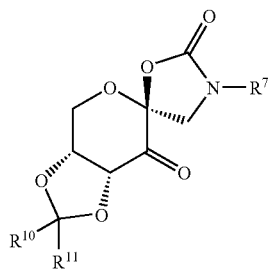

IV or a stereoisomer thereof, wherein $R^7$ is that defined herein; and each of $R^{10}$ and $R^{11}$ is independently selected from the group consisting of hydrogen, alkyl, aralkyl and aryl.

In one particular embodiment, the carbohydrate, e.g., starting material, is glucose, preferably (D)- or (L)-glucose.

In one embodiment, the amine is diaralkyl amine. In such an embodiment, the method can further include the steps of removing aralkyl groups from the amino nitrogen by contacting the dihydroxy-protected amino dihydroxy carbohydrate with hydrogen in the presence of a hydrogenation catalyst under conditions sufficient to produce a dihydroxy-protected free-amino carbohydrate prior to said heterocyclic moiety forming step (c).

Yet another aspect of the present invention provides a method for producing a fused-bicyclic compound of the formula:

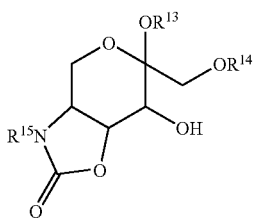

V wherein $R^{13}$ and $R^{14}$ are hydroxy protecting groups or $R^{13}$ and $R^{14}$ together with the carbon atoms to which they are attached to form an optionally substituted heterocyclyl; and $R^{15}$ is same as $R^7$ defined herein;

said method comprising
(a) contacting a trihydroxy-protected olefin compound of the formula:

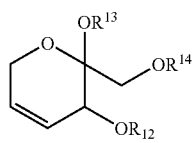

VI where
$R^{13}$ and $R^{14}$ are hydroxy protecting groups or $R^{13}$ and $R^{14}$ together with the carbon atoms to which they are attached to form an optionally substituted heterocyclyl; and $R^{12}$ is a hydroxy protecting group, with a hydroxy aminating agent under conditions sufficient to produce an amino hydroxy compound of the formula:

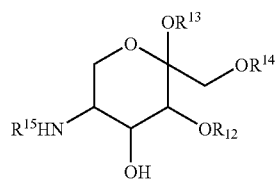

VII where
$R^{12}$, $R^{13}$, $R^{14}$ and $R^{15}$ are those defined herein;
(b) forming a heterocyclic moiety by contacting the amino hydroxy compound with an activated carbonate under conditions sufficient to produce a fused bicyclic compound of the formula:

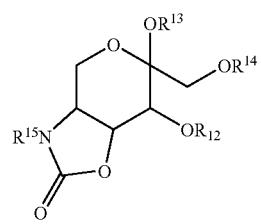

VIII where
$R^{12}$, $R^{13}$, $R^{14}$ and $R^{15}$ are those defined herein;
(c) selectively removing the $R^{12}$ hydroxy protecting group by contacting the fused bicyclic compound with a hydroxy protecting group removing agent under conditions sufficient to produce a monohydroxy fused bicyclic compound of the formula:

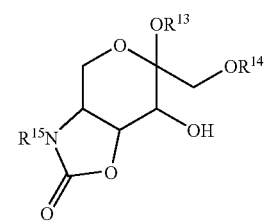

IX where
$R^{13}$, $R^{14}$ and $R^{15}$ are those defined above;
and
(d) oxidizing the free hydroxy group by contacting the monohydroxy fused bicyclic compound with an oxidizing agent under conditions sufficient to produce the fused-bicyclic compound of Formula V.

In this embodiment, $R^{15}$ can be converted to a desired substituent prior to or after the heterocyclyl moiety forming step (b) or after the oxidizing step (d). For example, when $R^{15}$ of compound of Formula VII is tosyl, the method can further comprise converting $R^{15}$ of compound of Formula VII to hydrogen, alkyl, aryl, —$(R^8)_n$—C(=O)—$R^9$, or other nitrogen protecting group, prior to said heterocyclic moiety forming step (b), said converting step comprising:

(i) removing the tosyl group of compound of Formula VII by contacting the compound of Formula VII with a tosyl removing agent under conditions sufficient to provide a compound of Formula VII comprising a free amine group, where $R^{15}$ is hydrogen; and (ii) optionally substituting the free amine group by contacting the compound of Formula VII comprising a free amine group with a compound of the formula $R^7$—X under conditions sufficient to produce a compound of Formula VII, wherein $R^7$ and $R^{15}$ are identical and is selected from the group consisting of alkyl, aryl, —$(R^8)_n$—C(=O)—$R^9$, or other nitrogen protecting group, where n, $R^8$ and $R^9$ are those defined herein; and X is a leaving group.

Alternatively, when $R^{15}$ of compound of Formula V is tosyl, the method can further comprise converting $R^{15}$ of compound of Formula V to hydrogen, alkyl, aryl, —$(R^8)_n$—C(=O)—$R^9$, or other nitrogen protecting group, after said oxidizing step (d), said converting step comprising:

(i) removing the tosyl group of compound of Formula V by contacting the compound of Formula V with a tosyl removing agent under conditions sufficient to provide a compound of Formula V comprising a free amine group, where $R^{15}$ is hydrogen; and (ii) optionally substituting the free amine group by contacting the compound of Formula V comprising a free amine group with a compound of the formula $R^7$—X under conditions sufficient to produce a compound of Formula V, wherein $R^7$ and $R^{15}$ are identical and is selected from the group consisting of alkyl, aryl, —$(R^8)_n$—C(=O)—$R^9$, or other nitrogen protecting group, where n, $R^8$ and $R^9$ are those defined herein; and X is a leaving group.

Preferably, the trihydroxy-protected olefin compound is produced from a carbohydrate. In one embodiment of the present invention, the trihydroxy-protected olefin compound producing step comprises:

(i) selectively protecting hydroxy groups of the carbohydrate with at least two different hydroxy protecting groups by contacting the carbohydrate with a first hydroxy protecting agent under conditions sufficient to produce a first carbohydrate comprising a first hydroxy protecting group and contacting the first carbohydrate with a second hydroxy protecting agent under conditions sufficient to produce a second carbohydrate comprising a first and a second hydroxy protecting groups, wherein the first and the second hydroxy protecting groups can be selectively removed;

(ii) removing at least a portion of the first hydroxy protecting group by contacting the second carbohydrate with a first hydroxy protecting group removing agent under conditions sufficient to produce a di-free hydroxy carbohydrate; and (iii) forming an olefinic bond by contacting the di-free hydroxy carbohydrate with a dihydroxy eliminating agent under conditions sufficient to produce the trihydroxy-protected olefin compound.

DETAILED DESCRIPTION OF THE INVENTION

Figure 1:
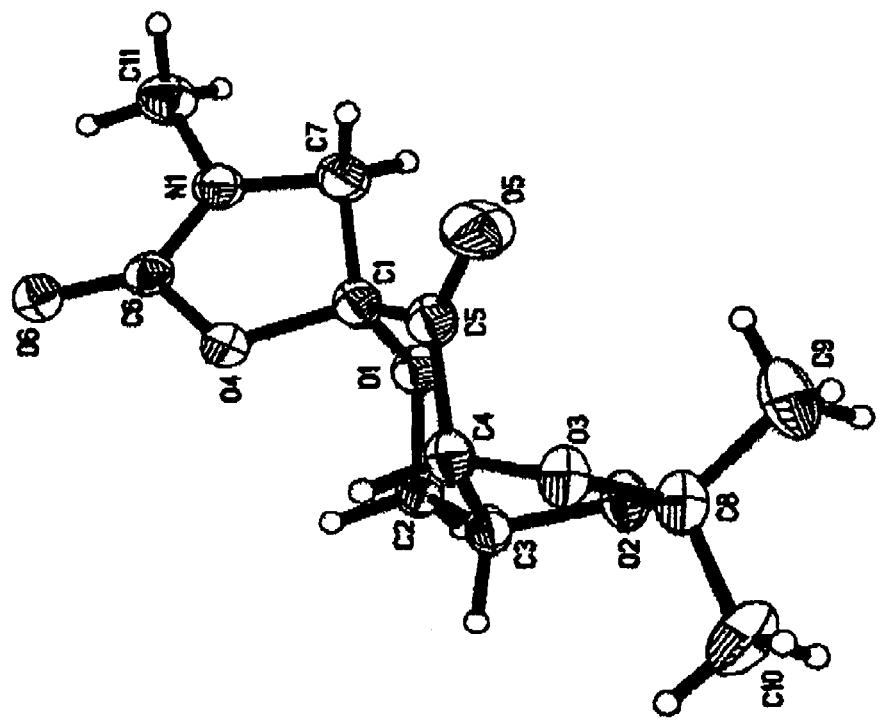
FIG. 1 is ORTEP view of X-ray structure of ketones IVa (left) and IVb (right)
Figure 1:
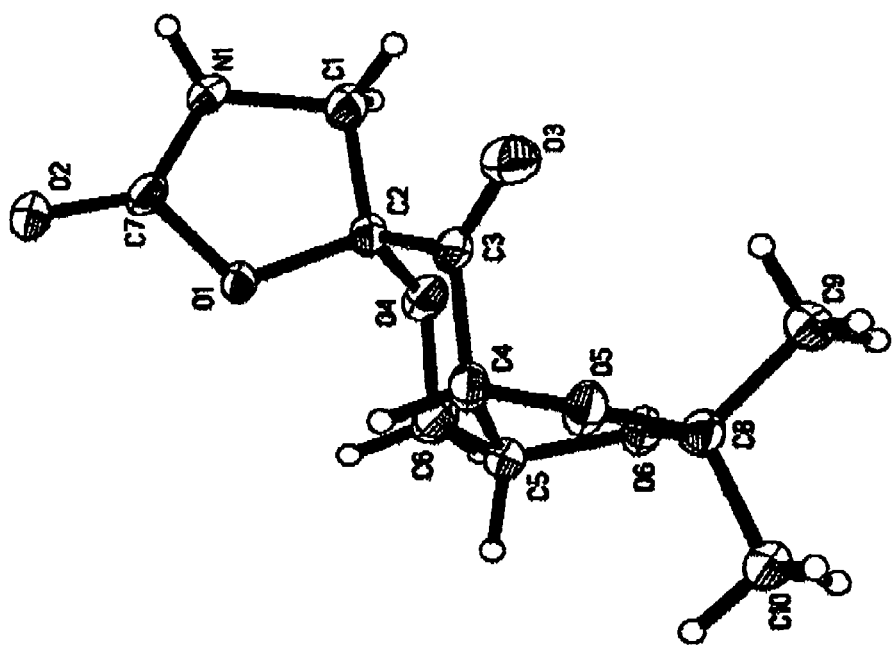
Figure 2:
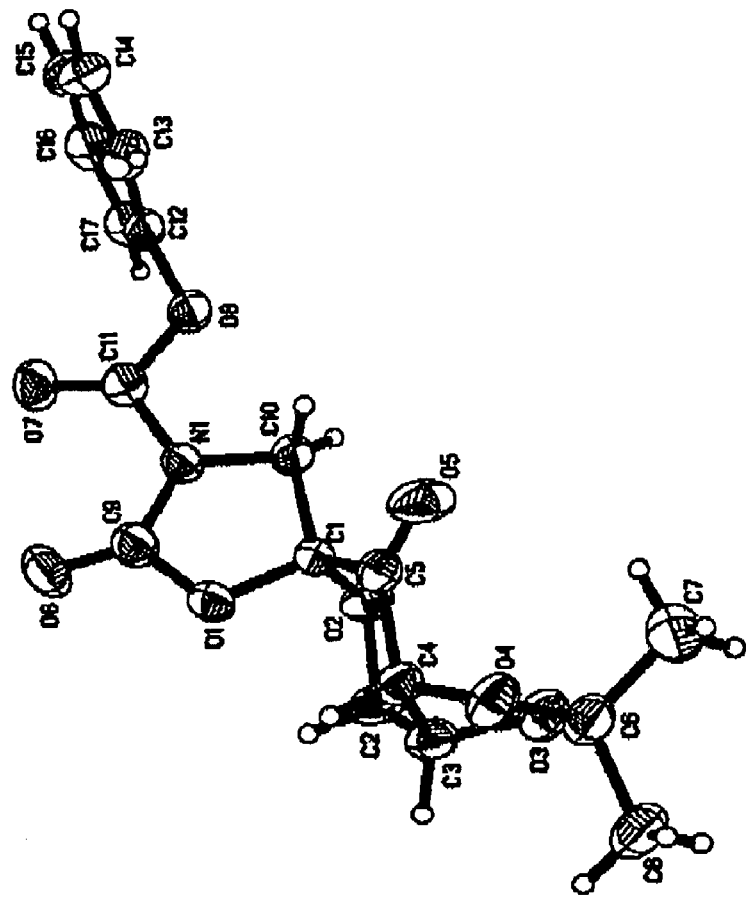
FIG. 2 is ORTEP view of X-ray structure of ketones IVd (left) and IVe (right).
Figure 2:
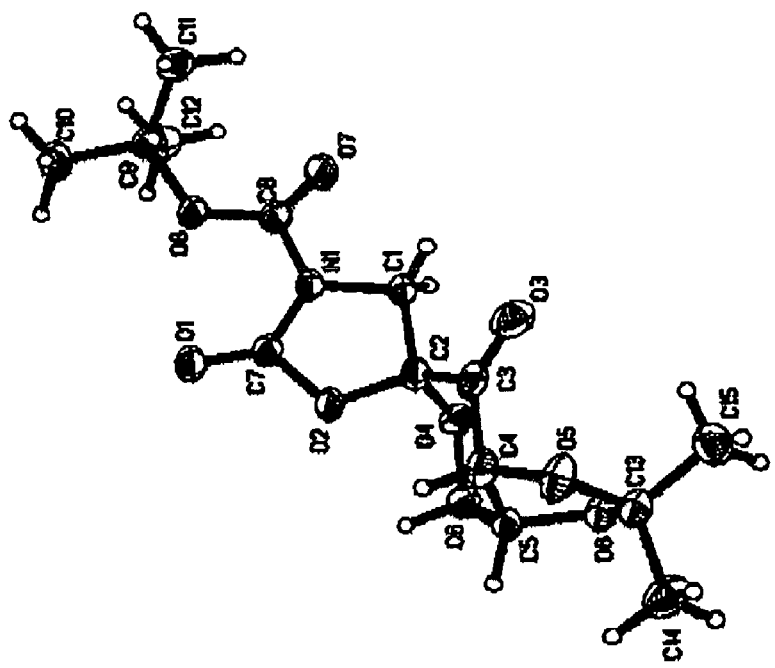

"Alkyl" refers to a linear saturated monovalent hydrocarbon moiety of one to ten carbon atoms or a branched saturated monovalent hydrocarbon moiety of three to ten carbon atoms. In addition, the alkyl group can be substituted with one or more halides, alkoxides, hydroxides or carbonyl groups. Exemplary alkyl groups include methyl, ethyl, propyl, 2-propyl, n-butyl, iso-butyl, tert-butyl, pentyl, trifluoromethyl, and the like.

"Aralkyl" refers to a moiety of the formula —$R^a R^b$ where $R^a$ is an alkylene group and $R^b$ is an aryl group as defined herein.

"Aryl" refers to a monovalent monocyclic or bicyclic aromatic hydrocarbon moiety of 6 to 10 ring atoms which is optionally substituted with one or more substituents, preferably one, two, or three substituents. Suitable substituents of aryl group include alkyl, halo, nitro, cyano, cycloalkyl, hydroxy, alkoxy, —$NR^a R^b$ (where $R^a$ is hydrogen or alkyl and $R^b$ is hydrogen, alkyl or a nitrogen protecting group), and the like.

"Carbohydrate" refers to natural or unnatural hydrocarbon moiety comprising six carbon atoms, a carbonyl carbon (or equivalents thereof, e.g., a carbon atom comprising an acetal or a ketal functionality) and a plurality of free hydroxy groups, preferably three or more free hydroxy groups, and more preferably five free hydroxy groups.

"Free hydroxy group" refers to a non-protected hydroxy group, i.e., a moiety of the formula —OH.

"Fused heterocyclyl" refers to a fused moiety consisting of a heterocyclic ring having two carbon atoms in common with the ring to which it is attached to. The fused moiety is formed when two hydrogen atoms from two different carbon atoms of the ring are replaced with a heterocyclyl group as defined herein.

"Heteroaralkyl" means a moiety of the formula —$R^a R^b$ where $R^a$ is an alkylene group and $R^b$ is a heteroaryl group as defined herein.

"Heteroaryl" means a monovalent monocyclic or bicyclic aromatic radical of 5 to 12 ring atoms containing one, two, or three ring heteroatoms selected from N, O, or S, the remaining ring atoms being C. The heteroaryl ring can optionally be substituted independently with one or more substituents, preferably one or two substituents.

"Heterocyclyl" refers to a saturated or unsaturated non-aromatic cyclic moiety of 3 to 8 ring atoms in which one or more, preferably at least two, ring atoms are heteroatoms selected from N, or O, the remaining ring atoms being C, where one or two ring C atoms may optionally be substituted with a carbonyl oxygen (i.e., =O). As such, a heterocyclyl includes acetonides that are formed by protection of 1,2-diol or 1,3-diol with an aldehyde or a ketone. The heterocyclyl ring may be optionally substituted independently with one, two, three, or four substituents selected from alkyl, haloalkyl, heteroalkyl, halide, hydroxy, alkoxy, amino, monoalkylamino, and dialkylamino. More specifically the term heterocyclyl includes, but is not limited to, 1,3-dioxolanyl, 2-oxazolidinonyl, and the derivatives thereof.

"Leaving group" has the meaning conventionally associated with it in synthetic organic chemistry, i.e., an atom or a group capable of being displaced by a nucleophile and includes halides (such as chloride, bromide, and iodide), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Monohydroxy carbohydrate" refers to a natural or unnatural carbohydrate comprising one free hydroxy group. Similarly, dihydroxy carbohydrate, trihydroxy carbohydrate, and tetrahydroxy carbohydrate refer to natural or unnatural carbohydrate comprising two, three and four free hydroxy groups, respectively.

"Nitrogen atom containing heterocyclyl" refers to heterocyclyl as defined herein where at least one of the ring atom is nitrogen.

"N-membered heterocyclyl" refers to a heterocyclyl as defined herein which comprises n number of atoms within the heterocyclyl ring system.

"Non-ring forming hydroxy protecting group" refers to a hydroxy protecting group that does not form a ring system when used to protect 1,2-diol or 1,3-diol group.

"Protecting group" refers to a grouping of atoms that when attached to a reactive group in a molecule masks, reduces or prevents that reactivity. Examples of protecting groups can be found in *Protective Groups in Organic Synthesis,* 3rd edition, T. W. Greene and P. G. M. Wuts, John Wiley & Sons, New York, 1999, and Harrison and Harrison et al., *Compendium of Synthetic Organic Methods*, Vols. 1–8 (John Wiley and Sons, 1971–1996), all of which are incorporated herein by reference in their entirety. Representative amide protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, carbamates, and the like.

"Spiro-heterocyclyl" refers to a spiro moiety consisting of a heterocyclic ring having only one carbon atom in common with the ring to which it is attached to. The spiro moiety is formed when two hydrogen atoms from the same carbon atom of the ring are replaced with a heterocyclyl group as defined herein.

As used herein, the terms "treating", "contacting" or "reacting", when referring to a chemical reaction, are used interchangeably and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

One aspect of the present invention provides a compound of the formula:

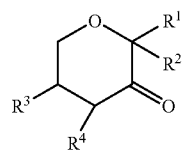

I and methods for producing and using the same, where one of $R^1$ and $R^2$ is —$OR^a$ and the other is -alkylene-$OR^b$, where each of $R^a$ and $R^b$ is independently a non-ring forming hydroxy protecting group, or $R^1$ and $R^2$ together with the carbon atoms to which they are attached to form an optionally substituted heterocyclyl; and each of $R^3$ and $R^4$ is independently hydrogen or —$OR^c$, where $R^c$ is a non-ring forming hydroxy protecting group, or $R^3$ and $R^4$ together with the carbon atoms to which they are attached to form an optionally substituted heterocyclyl, provided at least one of $R^1$ and $R^2$ together with the carbon atoms to which they are attached to or $R^3$ and $R^4$ together with the carbon atoms to which they are attached to form an optionally substituted nitrogen atom containing heterocyclyl. Preferably, the relative stereochemistry of $R^3$ and $R^4$ is a cis-configuration.

Preferably, the heterocyclyl moiety is an optionally substituted 5-membered heterocyclyl. More preferably, the heterocyclyl is selected from the group consisting of an optionally substituted 2-oxazolidinon-5-yl and an optionally substituted 1,3-dioxolan-4-yl.

In one particular embodiment of the present invention, $R^1$ and $R^2$ together with the carbon atoms to which they are attached to form an optionally substituted nitrogen atom containing heterocyclyl. Preferably in this embodiment, the compound of Formula I is of the formula:

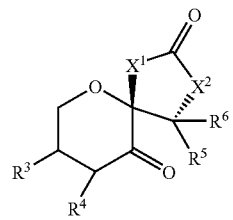

X where $R^3$ and $R^4$ are those defined above, preferably $R^3$ and $R^4$ together with the carbon atoms to which they are attached to form an optionally subsituted heterocycyl; one of $X^1$ and $X^2$ is O and the other is $NR^7$, preferably $X^1$ is O and $X^2$ is $NR^7$, where $R^7$ is selected from the group consisting of hydrogen, alkyl, aryl, —$(R^8)_n$—C(=O)—$R^9$, and other nitrogen protecting group, where n is 0 or 1, $R^8$ is alkylene, preferably methylene, and $R^9$ is hydroxy, alkyl, alkoxy, —$NR^aR^b$ (where $R^a$ and $R^b$ is independently hydrogen or alkyl), aryl and aryloxy; and each of $R^5$ and $R^6$ is independently selected from the group consisting of hydrogen, and alkyl, preferably hydrogen. Preferred $R^7$ is —$(R^8)_n$—C(=O)—$R^9$, where n=0. More preferably in this embodiment, the compound of Formula I is of the formula:

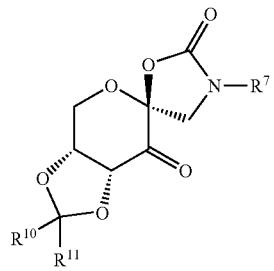

IV or a stereoisomer thereof, where $R^7$ is that defined herein; and each of $R^{10}$ and $R^{11}$ is independently selected from the group consisting of hydrogen, alkyl, aralkyl and aryl.

In another embodiment of the present invention, $R^3$ and $R^4$ together with the carbon atoms to which they are attached to form an optionally substituted nitrogen atom containing heterocyclyl. Preferably in this embodiment, the compound of Formula I is of the formula:

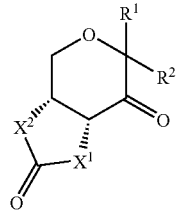

XI where $R^1$, $R^2$, $X^1$ and $X^2$ are those defined herein. Preferably in this embodiment, $R^1$ and $R^2$ together with the carbon atoms to which they are attached to form an optionally substituted heterocyclyl. More preferably in this embodiment, the compound of Formula I is of the formula:

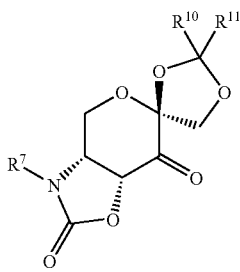

XII where $R^7$, $R^{10}$ and $R^{11}$ are those defined herein.

Representative Compounds of Formula I include, but are not limited to, the compounds listed in Table 1 below:

TABLE 1

Representative Compounds of Formula I.

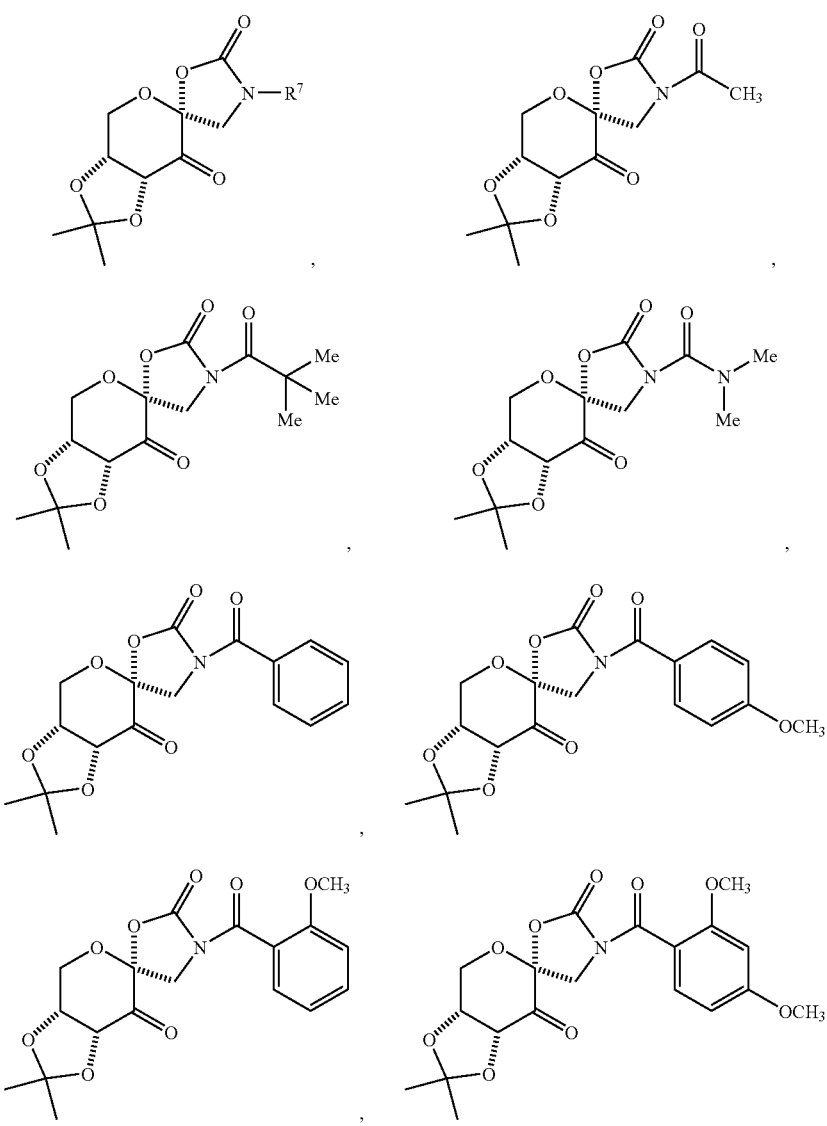

TABLE 1-continued
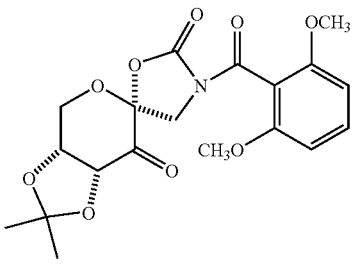 , 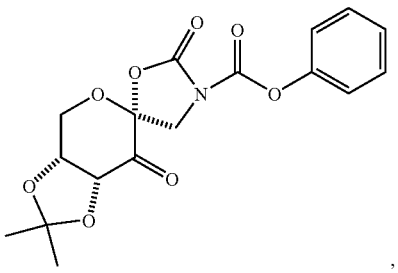 ,
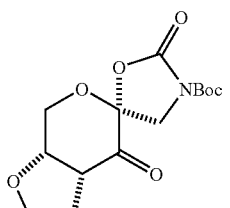 , 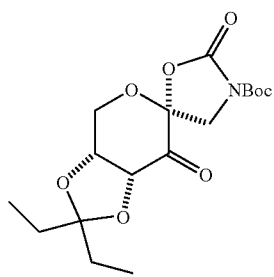 ,
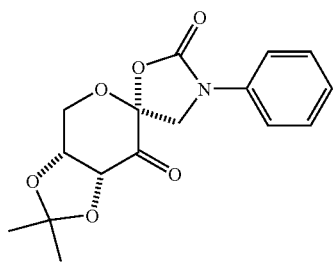 , 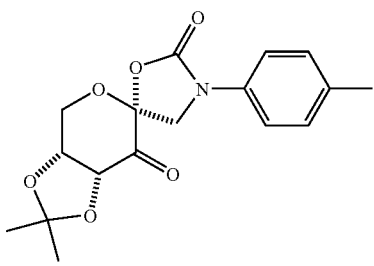 ,
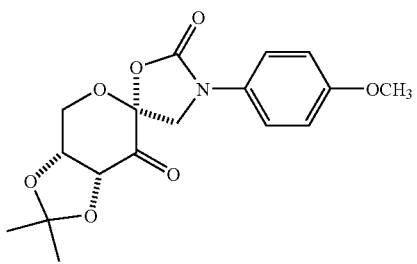 , 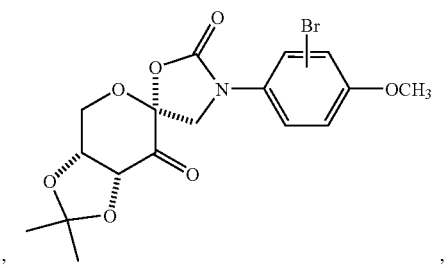 ,
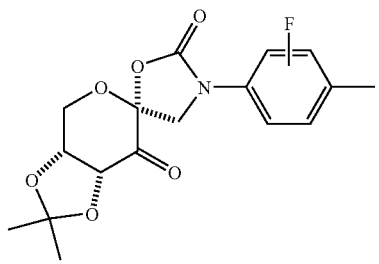 , 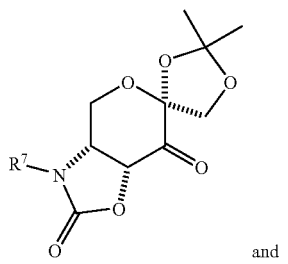 and

TABLE 1-continued

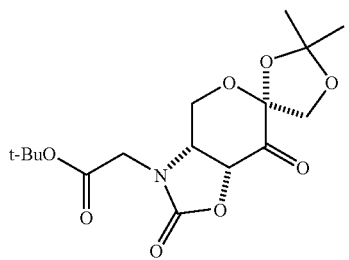

, where R[7] is hydrogen, methyl, benzyl or Boc-protecting group.

As generally shown above, compounds of the present invention replace the fused ketal moiety of 1 with an oxazolidinone moiety or the spiro ketal moiety of 1 with an oxazolidinone moiety.

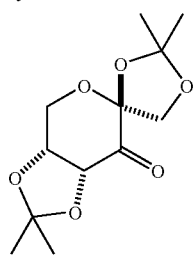

1

Synthesis of Compounds of Formula I

Compounds of Formula I can be synthesized by a variety of methods and using any appropriate starting material. For example, chiral cyclic ketones of Formula I can be prepared from a carbohydrate. Reasons for selecting a carbohydrate as the starting material include: (a) carbohydrates are chiral and readily available; (b) they are highly substituted with oxygen groups, which provide good reactivity, as the inductive effect of oxygen activates the ketone catalyst; and (c) carbohydrate-derived ketones have a relatively rigid conformations due to the anomeric effect, which is desirable for selectivity. In one particular embodiment, Compounds of Formula I are synthesized from glucose or fructose, preferably from (D))- or (L)-glucose or (D)- or (L)-fructose.

Synthesis of representative compounds of Formula I will now be described in reference to using a carbohydrate or a derivative thereof as the starting material. However, it should be appreciated that one skilled in the art can readily use other suitable compounds as the starting material given the teachings provided herein. Two particular embodiments for preparing representative compounds of Formula I are illustrated in Schems 1 and 2. These schemes are provided for the sole purpose of illustrating the practice of the present invention and are not intended to constitute limitations on the scope thereof.

Scheme 1

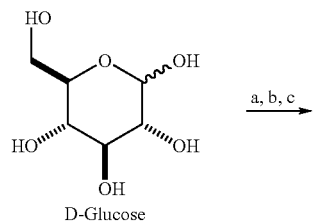

D-Glucose

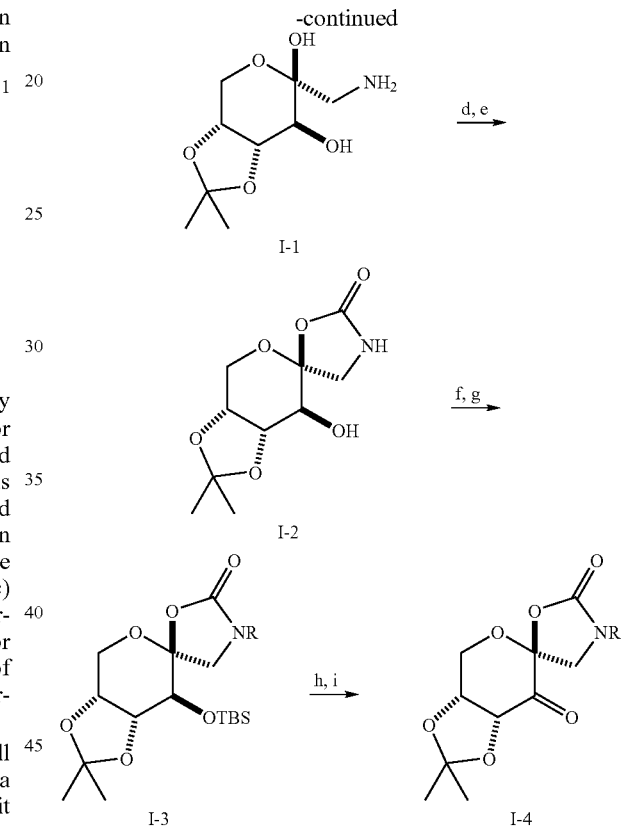

a. Bn$_2$NH, AcOH, EtOH, reflux, 3 h, 85%. b. (MeO)$_3$CH, CH$_2$COCH$_3$, HCl, 0° C., 2 h, 72%. c. H$_2$, 10% Pd/C, EtOH, rt, overnight, 88%. d: 4-MeOPhOCOCl, pyridine, CH$_2$Cl$_2$, 0° C., 5 h, 86%. e: (CH$_3$)$_3$COK, CH$_3$CN, rt, 0.5 h, 90%. f: TBSCl, imidazole, CH$_3$CN, rt, 24 h, 70%. g: RX, base. h: Et$_3$N•HF, THF. i: PDC, 3Å MS, AcOH, CH$_2$Cl$_2$.

Scheme 1 shows one method of producing a compound of Formula IV, where R[10] and R[11] are methyl. In this embodiment a carbohydrate, such as (D)-glucose, is converted to an N-glycoside. Amadori rearrangement of the N-glycoside in the presence of an acid, followed by protection of cis-diol and removal of the amino-protecting group then afforded the dihydroxy-protected amino dihydroxy carbohydrate I-1. Typically, the N-glycoside is produced using a di-substituted amine, preferably one in which the substituents can be subsequently removed, which allows one to easily prepare a wide variety of compounds of Formula IV. Alternatively, one can use a mono-substituted amine which provides the desired compound directly. Amadori rearrangement converts an N-glycosides of aldoses to N-glycosides of the corresponding ketoses. Reaction conditions for Amadori rearrangement are well known to one skilled in the art and generally involve an alcoholic solvent, such as ethanol, propanol and butanol. Conveniently, synthesis of N-glycoside and Amadori rearrangement can be carried out in one step. While a wide range of reaction temperature can used for this transformation, e.g., from about 20° C. to about 100° C., generally the reaction is carried out under the solvent refluxing conditions to produce an amino tetrahydroxy carbohydrate. Suitable acids for Amadori rearrangement include, but are not limited to, carboxylic acids, such as acetic acid; and other non-nucleophilic acids.

The hydroxy groups of the amino tetrahydroxy carbohydrate is then selectively protected as a ketal by using an orthoester, a ketone or an aldehyde in the presence of an acid catalyst. Protection of 1,2-diols as a ketal or an acetal are well known to one skilled in the art. See for example, *Protective Groups in Organic Synthesis*, 3rd edition, T. W. Greene and P. G. M. Wuts, John Wiley & Sons, New York, 1999, which is incorporated herein by reference in its entirety.

The amine is deprotected to yield a primary amine moiety. As discussed in detail below, the use of deprotectable amine allows preparation of a variety of compounds of Formula IIA by simple alkylation of the amine functional group.

Alternatively, by using a substituted amine, in particular an aryl or an alkyl amine, in the Amadori rearrangement, one can obtain the compound of Formula IV having a desired amine substituent as illustrated below, where R is an alkyl, or preferably an aryl group:

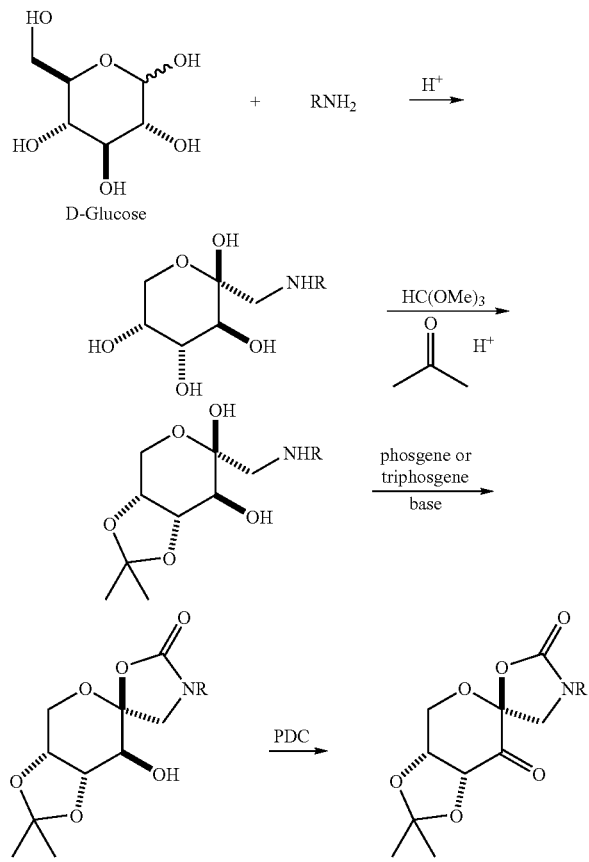

The dihydroxy-protected amino dihydroxy carbohydrate I-1 is then reacted with an activated carbonate to produce a spiro-bicyclic compound of Formula I-2. Typically, the spiro-bicyclic compound forming reaction includes a non-nucleophilic base such as a tertiary amine, pyridine, a bicarbonate or a carbonate. The reaction is conveniently conducted in an inert organic solvent at temperature 20° C. or below, preferably at 0° C. or below.

Generally the activated carbonate comprises a carbonate derivative comprising two functional groups selected from the group consisting of a halide, alkoxide, aryloxide, alkylthio, carboxylate (e.g., R—C(=O)—O—), derivatives thereof, and mixtures thereof. Exemplary activated carbonates include phosgene, triphosgene, a haloformate (i.e., X—C(=O)—OR, where X is a halide and R is alkyl, aryl or aralkyl), and bis-imidazole carbonyl. When the activated carbonate comprises an ester moiety, the reaction typically further requires addition of a relatively strong base that is non-nucleophilic, including tertiary amine, such as triethyl amine, and tert-butoxide. Typically, the reaction is conducted in an aprotic solvent such as acetonitrile and dichloromethane. The reaction temperature is generally at about 0° C. or above, preferably from about 0° C. to room temperature.

The free hydroxy group of a hydroxy spiro-bicyclic compound of Formula I-2 is then protected by treating with a hydroxy protecting group, e.g., silyl chloride, under conditions conventionally known to one skilled in the art. This protection of the free hydroxy group allows a selective substitution reaction (e.g., alkylation) on the carbamate nitrogen atom, thereby allowing a convergent and a rapid synthesis of a variety of compounds of Formula I. Typically, the substitution reaction is conducted in the presence of a base to neutralize the acid that is often generated in the reaction. The substitution reaction is conveniently carried out generally at room temperature or above. Alternatively, by using an appropriately substituted amine in Amadori rearrangement, one can avoid a separate alkylation or substitution reaction of the carbamate nitrogen atom.

The protected hydroxy group is then removed by contacting the hydroxy protected spiro-bicyclic compound of Formula I-3 with a hydroxy protecting group removing agent under conditions sufficient to produce a hydroxy spiro-bicyclic compound. Suitable reaction conditions for removing the corresponding hydroxy protection group are well known to one skilled in the art.

The hydroxy group is then oxidized to a carbonyl group by contacting the hydroxy spiro-bicyclic compound with an oxidizing agent to produce a spiro-bicyclic compound of Formula I-4. Any conventional oxidizing agents are suitable in this reaction. Exemplary oxidizing agents can be found on a variety of lieterature sources including *March's Advanced Organic Chemistry*, 5th ed., Smith and March, Wiley Interscience Publication, New York, 2001, and *Comprehensive Organic Transformations*, 2nd ed., Larock, John Wiley & Sons, Inc., New York, 1999, which are incorporated herein by reference in their entirety.

Scheme 2 shows a method of producing a compound of Formula XII, where $R^{10}$ and $R^{11}$ are methyl.

Scheme 2

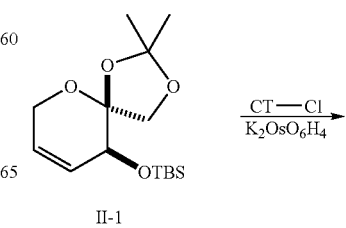

II-1

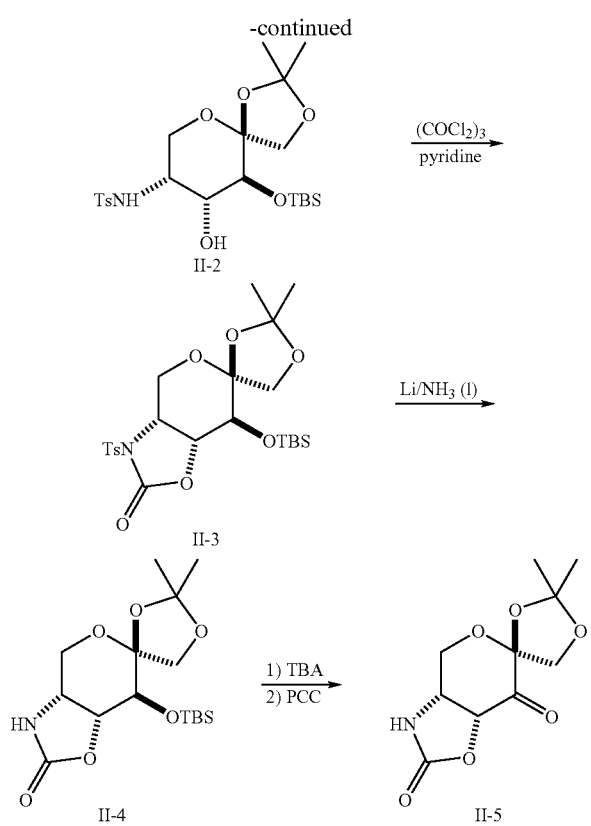

In this embodiment hydroxy amination of a trihydroxy-protected olefin, such as compound of Formula II-1, with a hydroxy aminating agent produces an amino hydroxy compound of Formula II-2. Suitable hydroxy aminating agents include a mixture of chloramine-T trihydrate and $K_2OsO_6H_4$; and other $X-NH-R^{16}$ compounds where X is a leaving group such as halide and $R^{16}$ is a carbonyl group (e.g., —C(=O)—OR$^{17}$, where $R^{17}$ is alkoxy, alkyl, aryloxy, or aryl). Typically this reaction is conducted in a mixture of an organic solvent and water, such as aqueous acetonitrile. The reaction is generally conducted at room temperture overnight. However, typically a higher reaction temperature results in a shorter reaction time, whereas a lower reaction temperature results in a longer reaction time.

The amino hydroxy compound of Formula II-2 is then reacted with an activated carbonate to produce a fused bicyclic compound of Formula II-3. Typically, the fused bicyclic moiety forming reaction includes a non-nucleophilic base such as a tertiary amine, pyridine, a bicarbonate or a carbonate. The reaction is conveniently conducted in an inert organic solvent at temperature 20° C. or below, preferably at 0° C. or below.

When the hydroxy amination reaction is conducted using a mixture of chloramine-T trihydrate and $K_2OsO_6H_4$, the resulting product contains a protected amino group, i.e., tosylated amino group. This protecting group can be removed by treating the fused bicyclic compound of Formula II-3 with lithium in liquid ammonia resulting in a free amino fused bicyclic compound of Formula II-4. The nitrogen atom of the carbamate can then be further functionalized as described above to provide a wide variety of compounds of Formula XII. Alternatively, the nitrogen atom of the carbamate can be functionalized after the oxidation of a hydroxy group as described below.

Selective removal of the hydroxy protecting group from the free amino fused bicyclic compound of Formula II-4 then affords a free hydroxy group which can be oxidized using a conventional oxidizing agent to provide a ketone of Formula II-5. If the carbamate nitrogen atom is not substituted (i.e., comprises a hydrogen), this ketone can be subjected to a substitution reaction as described above in reference to Scheme 1 to afford a wide variety of compounds of Formula XII.

The trihydroxy-protected olefin, such as compound of Formula II-1, can be readily prepared from a variety of starting materials including carbohydrates, such as (D)- or (L)-fructose, depending on the desired stereochemistry of the trihydroxy-protected olefin. For example, as shown in Scheme 3, hydroxy groups of (D)-fructose are protected with two different protecting groups to afford protected (D)-fructose II-7. Using two different protecting groups allows selective manipulation of desired hydroxy groups. Moreover, because of difference in reactivity, even the ketals in compound of Formula II-7 can be selectively deprotected using DDQ to afford a dihydroxy compound of Formula II-8.

Scheme 3

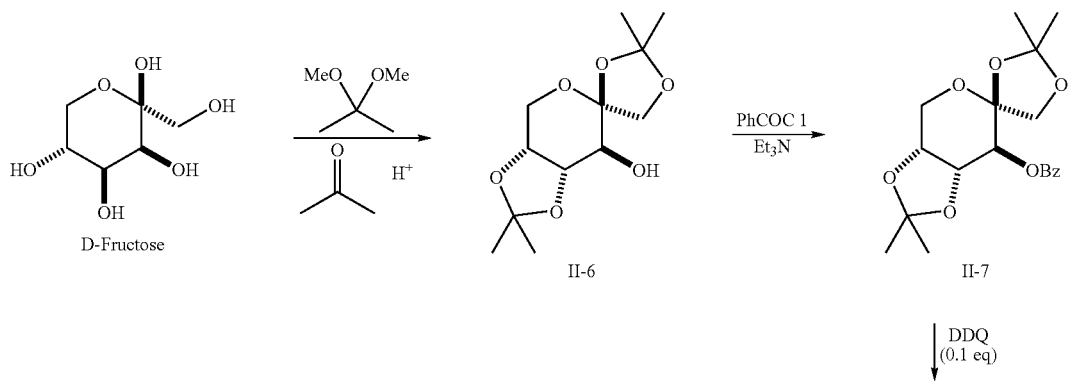

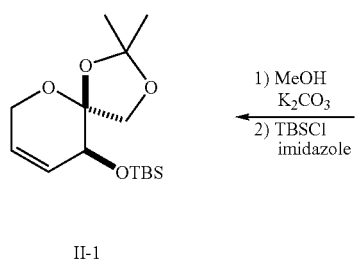 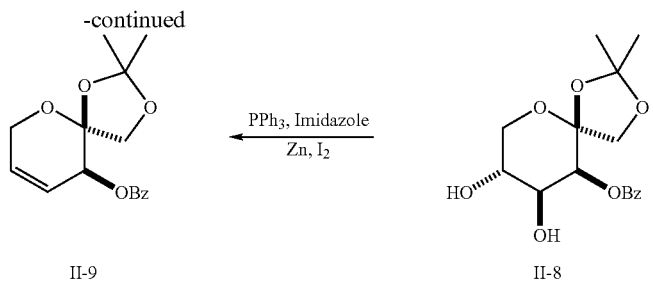

II-1      II-9      II-8

The resulting cis-dihydroxy groups in compound of Formula II-8 can be eliminated using a dihydroxy eliminating agent to afford compound of Formula II-9, which comprises a double bond. Suitable dihydroxy eliminating agents are well known to one skilled in the art and includes, a mixture of triphenyl phosphine, imidazole, zinc and iodine; and other suitable reagents known to one skilled in the art.

It should be appreciated that while the hydroxy groups in Schemes 1, 2 and 3 are protected using a 1,2-diol protecting agent, one can easily protect these hydroxy groups using a separate non-cyclic ring forming hydroxy protecting agent. Preferably the protecting groups for hydroxy groups are selected from the group consisting of silyl ethers, ethers, acetals, ketals, esters, ortho esters, sulfonates, phosphates and mixtures thereof. The protecting groups for two or more hydroxy groups of the carbohydrate or its derivative can be interconnected as shown in Schemes 1, 2 and 3 above. For example, an acetonide or an isopropylidene group protecting 4,5-hydroxy groups of fructose can be considered to be "two interconnected acetal protecting groups" since they protect two hydroxy groups on the carbohydrate, e.g., fructose and glucose.

It should also be appreciated that the carbohydrate can be monosaccharide or polysaccharide. Exemplary carbohydrates include glucose, fructose, maltose, lactose, mannose, sorbose, ribose, xylose, rhamnose, galactose, talose, arabinose, gulose, sucrose, cellobiose, cellulose, maltonic acid, heparin, chondroitin sulfate, amylose and amylopectin. Preferably, the carbohydrate is selected from the group consisting of fructose, sorbose arabinose, mannose and glucose. More preferably, the carbohydrate is selected from the group consisting of D)-glucose, (L)-glucose, (D)-fructose and (L)-fructose.

The oxidation of a hydroxy group of a carbohydrate to form a carbonyl group is well known to one skilled in the art. For example, pyridinium chlorochromate (PCC), pyridinium dichromate (PDC), Swern oxidation condition or other oxidizing conditions can be used to oxidize a hydroxy group of a carbohydrate or its derivative to a ketone compound of the present invention. Such oxidizing reagents are well known to one skilled in the art.

Utility

Epoxides are used in many industrial processes as chiral building blocks for the synthesis of enantiomerically pure complex molecules such as polymers, surfactants, pesticides, insecticides, insect hormones, insect repellants, pheromones, food flavoring, and drugs. The stereochemistry of a molecule is important in many of the properties of the molecule. For example, it is well known that physiological properties of drugs having one or more chiral centers, i.e., stereochemical centers, depend on the stereochemistry of a drug's chiral center. In addition, properties of a polymer containing a chiral monomeric unit depend on the enantiomeric purity of the monomer. Thus, it is advantageous to be able to control the stereochemistry of a chemical reaction. Since an epoxide serve as an intermediate or a starting material for many chemical compounds, it is especially desirable to be able to control the stereochemistry of the epoxide formation.

Compound of the present invention are useful in asymmetrically epoxidizing olefins. A chiral center (i.e., stereochemical center, or stereogenic center) is, of course, an atom to which four different groups are attached; however, the ultimate criterion of a chiral center is nonsuperimposability on the mirror image. Facially selective, stereoselective, enantioselective or asymmetric synthetic reactions are those in which one of a set of stereoisomers is formed exclusively or predominantly.

Preferably, one stereoisomer of the epoxide is produced in at least about 50 percent excess over the other stereoisomer, more preferably in at least about 80 percent excess, still more preferably in at least about 90 percent excess, and most preferably in at least about 95 percent excess. As used in this invention, an "olefin" refers to a compound having an alkene functionality, i.e., a double bond between two carbon atoms. An olefin can have more than one double bond. If more than one double bond is present on the olefin, the double bonds can be conjugated or non-conjugated. The olefin can be monosubstituted, di-substituted, tri-substituted or fully substituted. By substituted, it is meant that the olefinic carbon atom is attached to an atom other than hydrogen atom. For example, the olefinic carbon can be substituted with a halogen atom, silicon atom, another carbon atom, oxygen atom, sulfur atom and/or a metal atom such as tin. Preferably, the olefin is terminal or cis olefin. The di-substituted olefin can be geminal, cis-, or trans-substituted olefin. Generally for olefins having at least three substituent groups, trans-olefin designation refers to the trans relationship between the larger substituents attached to the two different olefinic carbon atoms, whereas cis designation refers to the cis relation between the larger substituents. In addition to cis- and trans-notation an "E" or "Z" notation can used to denote the relative priority of the substituent groups. E- and Z-notations denoting the stereoisomers of alkenes are well known to one of ordinary skill in the art.

Without being bound by a theory, it is believed that contacting an oxidizing agent with a ketone produces a dioxirane. Although some dioxiranes may be isolated under certain conditions, in general they are generated and used in situ by contacting (i.e., reacting) a ketone with an oxidizing agent. It is generally believed that it is this dioxirane which is generated in situ that is responsible for the formation of an epoxide from the olefin. Moreover, dioxiranes generated in situ from chiral ketones have been shown to be remarkably promising oxidation reagents for the asymmetric epoxidation of olefins. As disclosed in commonly assigned PCT Patent Application No. PCT/US97/18310, filed on Oct. 8, 1997, which is incorporated herein by reference in its entirety, present inventors have found that a carbohydrate (e.g., fructose or glucose) derived ketones are particularly effective epoxidation catalysts, in that it gives high enantiomeric excess (i.e., ee's) for a variety of olefins including trans- and trisubstituted olefins (eq. 1).

(eq. 1)

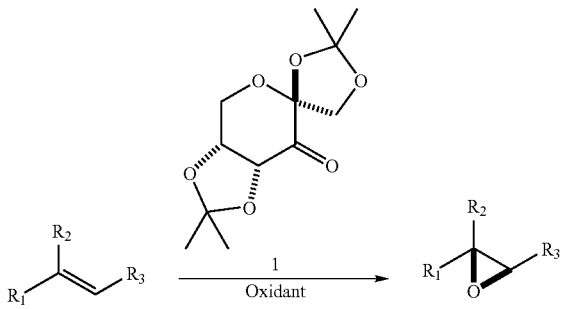

The present inventors have found that the Compounds of Formula I are also useful in epoxidizing olefins. In particular, Compounds of Formula I are particularly useful in epoxidizing cis-, preferably di-substituted cis-, and terminal olefins with high enantioselectivity.

The methods of the present invention regenerate the ketone (i.e., Compound of Formula I); therefore, the ketone can be used in a catalytic amount. The average number of epoxidation of olefins produced by a ketone molecule is known as a catalytic turn-over number, or simply a turn-over number. Preferably the ketones of the present invention have a turn-over number of at least about 3, more preferably at least about 10 and most preferably at least about 50. Moreover, since the ketones have such a high turn-over number, the amount of the ketones required to epoxidize a given amount of olefin can be less than the stoichiometric amount (i.e., one equivalent) of the olefin. Preferably no more than about 0.3 equivalents of the ketone is used to epoxidize olefins, more preferably no more than about 0.05 equivalents, and most preferably no more than about 0.01 equivalents.

As stated above, compounds of Formula I can be used in an amount less than the stoichiometric amount relative to the amount of the olefin. It should be appreciated that in situ generation of dioxirane from a ketone generally requires the oxidizing agent to be more reactive towards the ketone than the olefin to avoid competing oxidation of olefin by the oxidizing agent. However, when the reactivity of the oxidizing agent towards the olefin is similar or greater than its reactivity towards the ketone, one can use a large excess amount of ketone relative to the amount of olefin to increase the reaction rate between the oxidizing agent and the ketone relative to the reaction rate between the oxidizing agent and the olefin. In these cases, preferably the amount of ketone used is at least about 3 times more than the amount olefin, more preferably at least about 5 times, and most preferably at least about 10 times.

Any oxidizing agent capable of providing dioxiranes from a corresponding ketone can be used in the present invention. However, for economic reasons a relatively inexpensive oxidizing agents such as organic peracids, hydrogen peroxide, sodium hypochlorite, potassium peroxomonosulfate, sodium perborate and hypofluoride (HOF) are preferred. Preferably, the oxidizing agent is potassium peroxomonosulfate. Non-organic oxidizing agents (i.e, a compound that does not contain any carbon atom) are particularly preferred as these oxidizing agents and their reaction products can be easily removed from the reaction mixture by a simple aqueous extraction. The amount of oxidizing agent used in the present invention depends on a variety of factors including the reactivity of the ketone, olefin, and the decomposition rate of the oxidizing agent. Preferably, the amount of an oxidizing agent used is at least about 1 times the amount of the ketone, more preferably at least about 9 times, and most preferably at least about 100 times. In another embodiment of the present invention, the amount of oxidizing agent used is less than about 10 times the amount of olefin, more preferably less than about 3 times the amount of olefin, and most preferably about 1–2 times the amount of olefin.

In some cases, the reaction time affects both the yield of the epoxide as well as the enantiomeric excess of the epoxide product. Thus, while in some cases a longer reaction period provides higher yield of the epoxide, the enantiomeric excess begins decrease after certain period of time. Therefore, obtaining a maximum yield of the epoxide while maintaining a sufficient level of enantiomeric excess requires a compromise between the two diametrically opposed results. Preferably, the reaction time is from about 0.1 h to about 24 h, more preferably from about 0.1 h to about 8 h, and most preferably from about 0.1 h to about 5 h.

Depending on the oxidizing agent used and the reaction conditions, in some cases the pH of the reaction mixture is also an important factor for the epoxidation with dioxiranes generated in situ. In such instances, the pH of the reaction mixture is preferably maintained at from about pH 5 to about pH 14, more preferably from about pH 7 to about pH 12, and most preferably from about pH 8 to about pH 11. The pH of the reaction solution can be conveniently achieved by adding a sufficient amount of base (or a buffer solution) to maintain the pH at the desired level. The base can be added separately, it can be added to the solution containing the ketone, or it can be added to the solution containing the oxidizing agent. Alternatively, a solid mixture of the base and oxidizing agent can be added to the reaction mixture. Preferably the base is selected from the group consisting of hydroxides, carbonates, bicarbonates, borates and phosphates. More preferably the base is selected from the group consisting of potassium carbonate, potassium bicarbonate, lithium carbonate, lithium bicarbonate, sodium carbonate, sodium bicarbonate, calcium carbonate, sodium borate, sodium phosphate, potassium phosphate, lithium hydroxide, sodium hydroxide, potassium hydroxide, magnesium hydroxide and calcium hydroxide. Most preferably the base is selected from the group consisting of potassium carbonate, potassium bicarbonate, sodium bicarbonate, sodium carbonate, sodium hydroxide, sodium borate, sodium phosphate, potassium phosphate and potassium hydroxide. Alternatively, the desire pH of the reaction can be more easily maintained by using a buffer solution.

In some cases, the yield of epoxide and/or enantioselectivity of the reaction is affected by the solvent system used. Typically, any suitable organic solvent can be used for the present invention. Exemplary solvents include, nitriles such as acetonitrile and propionitrile, dimethoxymethane (DMM), dimethoxyethane (DME), ethers such as tetrahydrofuran (THF) and diethyl ether ($Et_2O$), dichloromethane, chloroform, ethyl acetate, hexane, benzene, toluene, xylenes, dioxane, dimethyl formamide (DMF), pentane, alcohols including, but not limited to, methanol, ethanol and i-propyl alcohol, and mixtures thereof. Alternatively, a mixture of organic solvent and an aqueous solution is used as a reaction solution.

Percentage of enantiomeric excess (% ee), which is a measure of enantioselectivity, is equal to % of one enantiomer (e.g. stereoisomer) minus % of the other enantiomer. Thus for example, if the reaction produces (R,R) and (S,S) epoxides in 99% and 1%, respectively, the enantiomeric excess percentage (% ee) will be 98%. Preferably, methods of the present invention provide asymmetric epoxidation of olefins in at least about 50% ee, more preferably at least about 80% ee, and most preferably at least about 90% ee. In another embodiment of the present invention, the yield of the epoxide from asymmetric epoxidation of an olefin is at least about 10%, more preferably at least about 50%, and most preferably at least about 80%.

The temperature of the reaction can also affect the yield of the reaction and/or enantioselectivity of the epoxide. Generally, a lower reaction temperature requires a longer reaction time but results in higher enantioselectivity. Preferably the reaction temperature is less than about 100° C., more preferably less than about 30° C., and most preferably about 0° C. or less.

Surprisingly and unexpectedly, present inventors have found that methods of the present invention are particularly useful in providing a high enantiomeric excess in epoxidation of cis-disubstituted olefins and terminal olefins (i.e., geminal di-substituted olefins or in particular monosubstituted terminal olefins).

Asymmetric epoxidation of olefins according to the present invention can be performed in a variety of different sequences. The addition sequence of the olefin, ketone, oxidizing agent, and base (if used) can be interchanged depending on the nature of each components. Typically, however, a solution comprising an oxidizing agent and a separate base solution or a solid oxidizing agent and a solid base are added to a solution comprising the ketone and the olefin. A reverse-addition technique can also be used depending upon the reactivity of each component. A reverse-addition is where the solution comprising the ketone is added to the solution comprising the oxidizing agent or to a solid oxidizing agent. Preferably, the initial concentration of the olefin is from about 0.001 mole/liter (M) to about 10 M, more preferably from about 0.02 M to about 1 M.

Another aspect of the present invention, in some cases, is the ease of separation between the epoxide and the ketone. Some epoxides readily dissolve and remain in relatively non-polar organic solvents such as hexane, pentane, and mixtures thereof, whereas the ketone remains in aqueous solution. Typically the reaction mixture is diluted with an extraction solvent to separate the epoxide from the ketone. Additionally, aqueous solution can also be added to the reaction mixture to further facilitate removal of the ketone from the organic layer. After separating the two layers, the extraction solvent layer comprising the epoxide can further be washed with an aqueous solution to further remove the ketone that may be present in the extraction solvent layer. This washing can be repeated until substantially all of the ketone is removed from the extraction solvent layer. Conversely, the aqueous layer can be further washed with the extraction solvent to further obtain the epoxide that may be present in the aqueous layer. Again, this extraction can be repeated until substantially all the epoxide has been obtained. The epoxide which is separated from the ketone can further be purified by any of the current separation methods such as chromatography, distillation, and crystallization.

The asymmetric epoxidation methods of the present invention are environmentally friendly. Water can be used as a co-solvent and unlike other current asymmetric epoxidation no toxic metals are involved. Therefore, no special disposal method is required, which significantly reduces the overall cost of the present invention.

Additional objects, advantages, and novel features of this invention will become apparent to those skilled in the art upon examination of the following examples thereof, which are not intended to be limiting.

EXAMPLES

General Methods

Oxone was purchased from Aldrich (it has been found that the oxidation activity of the purchased Oxone occasionally varies with different batches). All glassware used for the epoxidation was carefully washed to be free of any trace metals which catalyze the decomposition of Oxone. Elemental analyses were performed by M-H—W Laboratories, Phoenix, Ariz.

Example 1

This example illustrates a method for synthesizing a variety of chiral ketones of Formaul XII of the present invention starting from a readily available D-fructose.

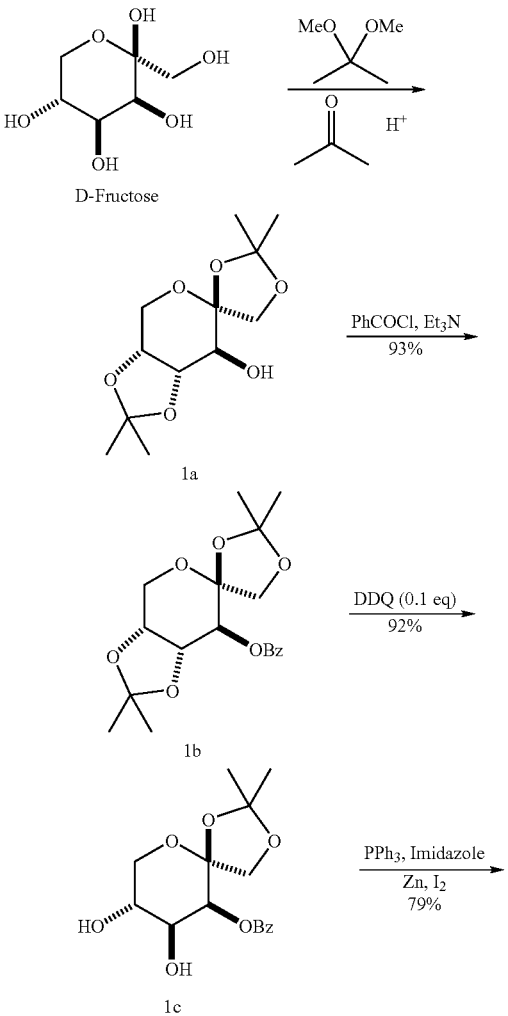

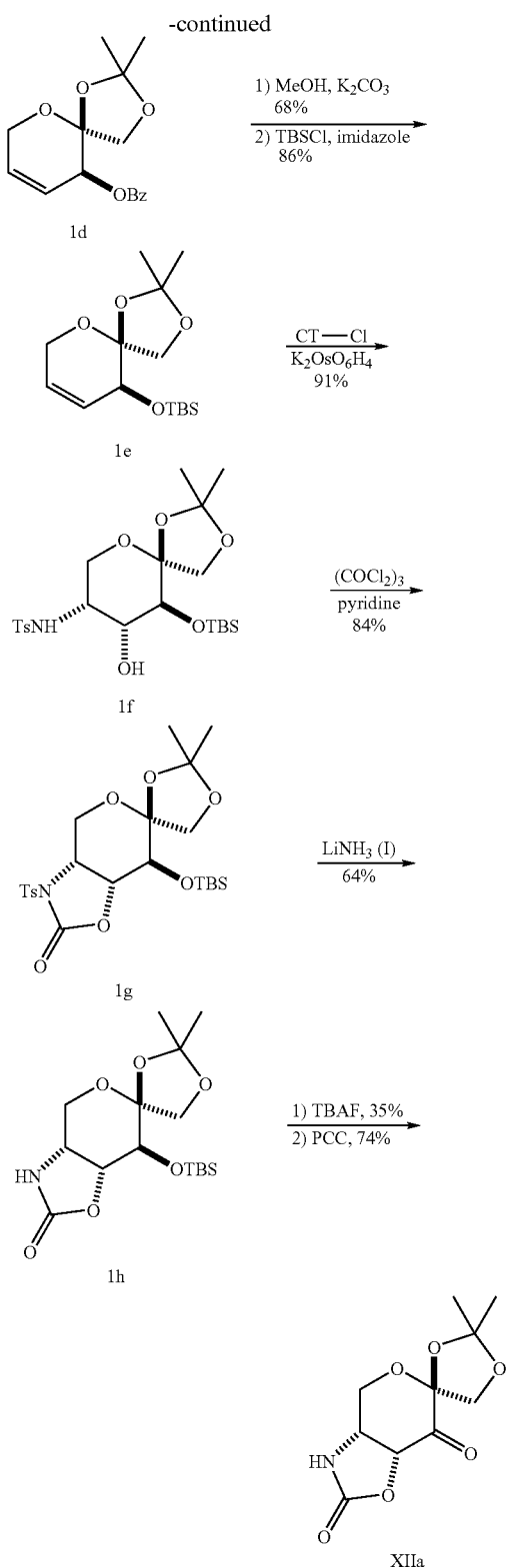

at rt until no starting material was left as judged by TLC, the reaction mixture was poured into water, extracted with Et₂O, washed with brine, dried (Na₂SO₄), filtered, concentrated, and purified by flash chromatography to give compound 1b (3.39 g, 93%).

To a solution of compound 1b (0.364 g, 1 mmol) in CH₃CN/H₂O (3.4 mL, 9/1) was added DDQ (0.0227 g, 0.1 mmol). Upon stirring at rt for 24 h, the reaction mixture was concentrated and purified by flash chromatography to give diol 1c (0.297 g, 92%).

To a refluxing mixture of diol 1c (2.5 g, 7.72 mmol), PPh₂ (7.69 g, 29.32 mmol), imidazole (3.78 g, 55.56 mmol) and zinc (0.031 g) in toluene (37 mL) was added I₂ (3.92 g, 15.43 mmol) over 45 min. After the reaction mixture was stirred at refluxing for another 1 h, another batch of zinc (0.031 g) was added. Upon stirring for additional 3.5 h, the reaction mixture was cooled down, filtered, concentrated, and purified by flash chromatography to give compound 1d (1.77 g, 79%).

To a solution of compound 1d (24.56 g, 84.69 mmol) in methanol (423 mL) was added K₂CO₃ (23.41 g, 169 mmol). Upon stirring at rt for 12 h, the reaction mixture was filtered, concentrated, and purified by flash chromatography to give the alcohol (10.78 g, 68%).

To a solution of the above alcohol (23.52 g, 126 mmol) in DMF (130 mL) were added imidazole.(17.22 g, 253 mmol) and TBDMSCl (28.58 g, 190 mmol) at rt. Upon stirring for 24 h., the reaction mixture was quenched with water, extracted with EtOAc, washed with brine, dried (Na₂SO₄), filtered, concentrated, and purified by flash chromatography to give compound 1e (32.69 g, 86%).

To a solution of compound 1e (2.16 g, 7.2 mmol) in CH₃CN/H₂O (14 mL, 1/1) were added chloramine-T trihydrate (2.44 g, 8.64 mmol) and K₂OsO₆H₄ (0.018 g, 0.036 mmol). After the mixture was stirred at rt overnight, Na₂SO₃ and EtOAc were added. Upon stirring for an additional 1 h, the layers were separated. The organic layer was dried (Na₂SO₄), filtered, concentrated, and purified by flash chromatography to give compound 1f (3.09 g, 91%).

To a solution of if (0.50 g, 1.062 mmol) and pyridine (0.84 g, 10.62 mmol) in CH₂Cl₂ (5 mL) at 0° C. was added triphosgene (0.315 g, 1.062 mmol). Upon stirring at 0° C. for 4 h, the reaction mixture was quenched with water, extracted with EtOAc, dried (Na₂SO₄), filtered, concentrated, and purified by flash chromatography to give compound 1g (0.442 g, 84%).

To a solution of sulfonamide 1g (26.57 g, 51.79 mmol) in THF (52 mL) and liquid ammonia (450 mL) at −78° C. was added Li (3.60 g, 518.0 mmol). Upon stirring at −78° C. overnight, the reaction mixture was quenched with solid NH₄Cl and warmed to evaporate NH₃. The resulting mixture was diluted with MeOH, filtered, concentrated, and purified by flash chromatography to give compound 1h (11.91 g, 64%).

To a solution of compound 1h (0.8 g, 2.23 mmol) in THF (20 mL) was added TBAF (2.23 mL, 2.23 mmol, 1.0 M in THF) at rt under N₂. The mixture was stirred until no starting material was left as judged by TLC. Upon concentration, the mixture was purified by flash chromatography to give the alcohol (0.19 g, 35%).

To a mixture of the above alcohol (0.19 g, 0.776 mmol) and powdered 3 Å MS (0.72 g) in CH₂Cl₂ (3.5 mL) was added PCC (0.384 g, 1.781 mmol) portionwise over 15 min. Upon stirring at rt under N₂ for 3 h, the reaction mixture was filtered through celite and washed with Et₂O. The filtrate was concentrated and purified by flash chromatography to give ketone XIIa (0.14 g, 74%).

Preparation of Ketone XIIa

To a solution of alcohol 1a (2.6 g, 10 mmol) (Wang, Z -X.; Tu, Y.; Frohn, M.; Zhang, J -R.; Shi, Y. *J. Am. Chem. Soc.* 1997, 119, 11224) in CH₂Cl₂ (15 mL) were added Et₃N (5 mL, 30 mmol) and PhCOCl (1.7 g, 12 mmol). Upon stirring

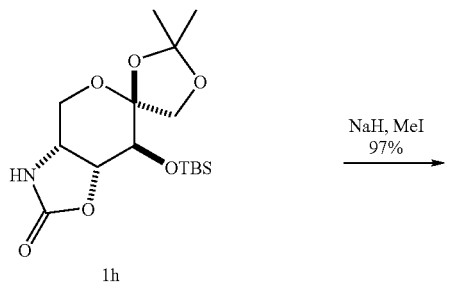
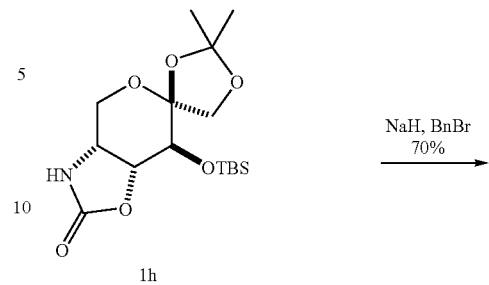
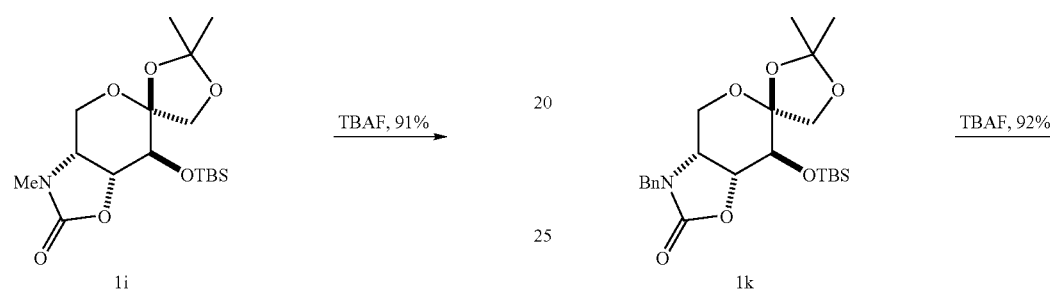
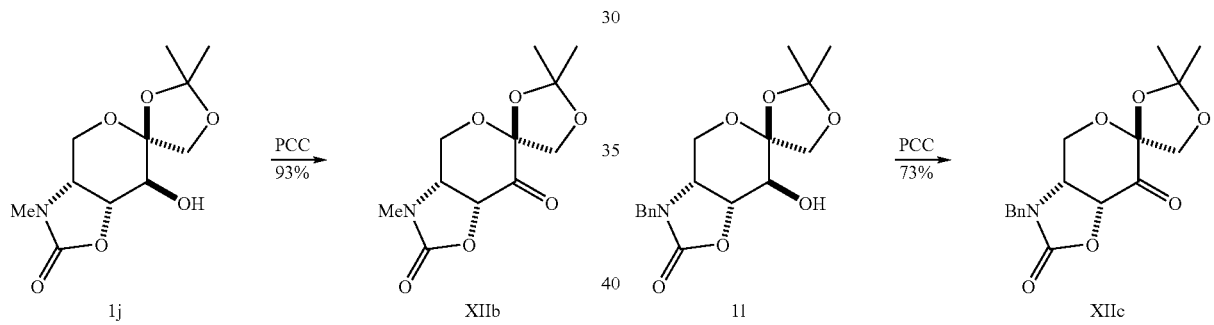

Preparation of Ketone XIIb

To a solution of compound 1h (0.064 g, 0.178 mmol) in THF (2 mL) was added NaH (0.009 g, 0.214 mmol) at 0° C. under $N_2$. After the reaction mixture was stirred at 0° C. for 0.5 h, MeI (0.05 g, 0.356 mmol) was added. Upon stirring for another 2 h at rt., the reaction was quenched with water, extracted with EtOAc, washed with brine, dried ($Na_2SO_4$), filtered, concentrated, purified by flash chromatography to give compound 1i (0.064 g, 97%).

To a solution of compound 1i (0.315 g, 0.845 mmol) in THF (10 mL) was added TBAF (0.85 mL, 0.85 mmol, 1.0M in THF) at rt under $N_2$. Upon stirring until no starting material was left, the reaction mixture was concentrated and purified by flash chromatography to give alcohol 1j (0.199 g, 91%).

To a mixture of alcohol 1j (0.199 g, 0.77 mmol) and powdered 3 Å MS (0.72 g) in $CH_2Cl_2$ (3.8 mL) was added PCC (0.385 g, 1.79 mmol) portionwise over 15 min. Upon stirring at rt under $N_2$ for 3 h, the reaction mixture was filtered through celite and washed with $Et_2O$. The filtrate was concentrated and purified by flash chromatography to give ketone XIIb (0.183 g, 93%).

Preparation of Ketone XIIc

To a solution of compound 1h (0.718 g, 2.0 mmol) in THF (10 mL) was added NaH (0.12 g, 3.0 mmol) at 0° C. under $N_2$. After the reaction mixture was stirred at 0° C. for 0.5 h, BnBr (0.513 g, 3 mmol) was added. Upon stirring at rt for another 2 h, the reaction mixture was quenched with water, extracted with EtOAc, washed with brine, dried ($Na_2SO_4$), filtered, concentrated, and purified by flash chromatography to give compound 1k (0.631 g, 70%).

To a solution of compound 1k (0.598 g, 1.333 mmol) in THF (15 mL) was added TBAF (1.4 mL, 1.4 mmol, 1.0 M in THF) at rt under $N_2$. Upon stirring until no starting material was left (by TLC), the reaction mixture was concentrated and purified by flash chromatography to give alcohol 1l (0.409 g, 92%).

To a mixture of alcohol 1l (0.409 g, 1.22 mmol) and powdered 3 Å MS (1.12 g) in $CH_2Cl_2$ (5.3 mL) was added PCC (0.605 g, 2.807 mmol) portionwise over 15 min. Upon stirring under $N_2$ for 3 h, the reaction mixture was filtered through celite and washed with $Et_2O$. The filtrate was concentrated and purified by flash chromatography to give ketone XIIc (0.298 g, 73%).

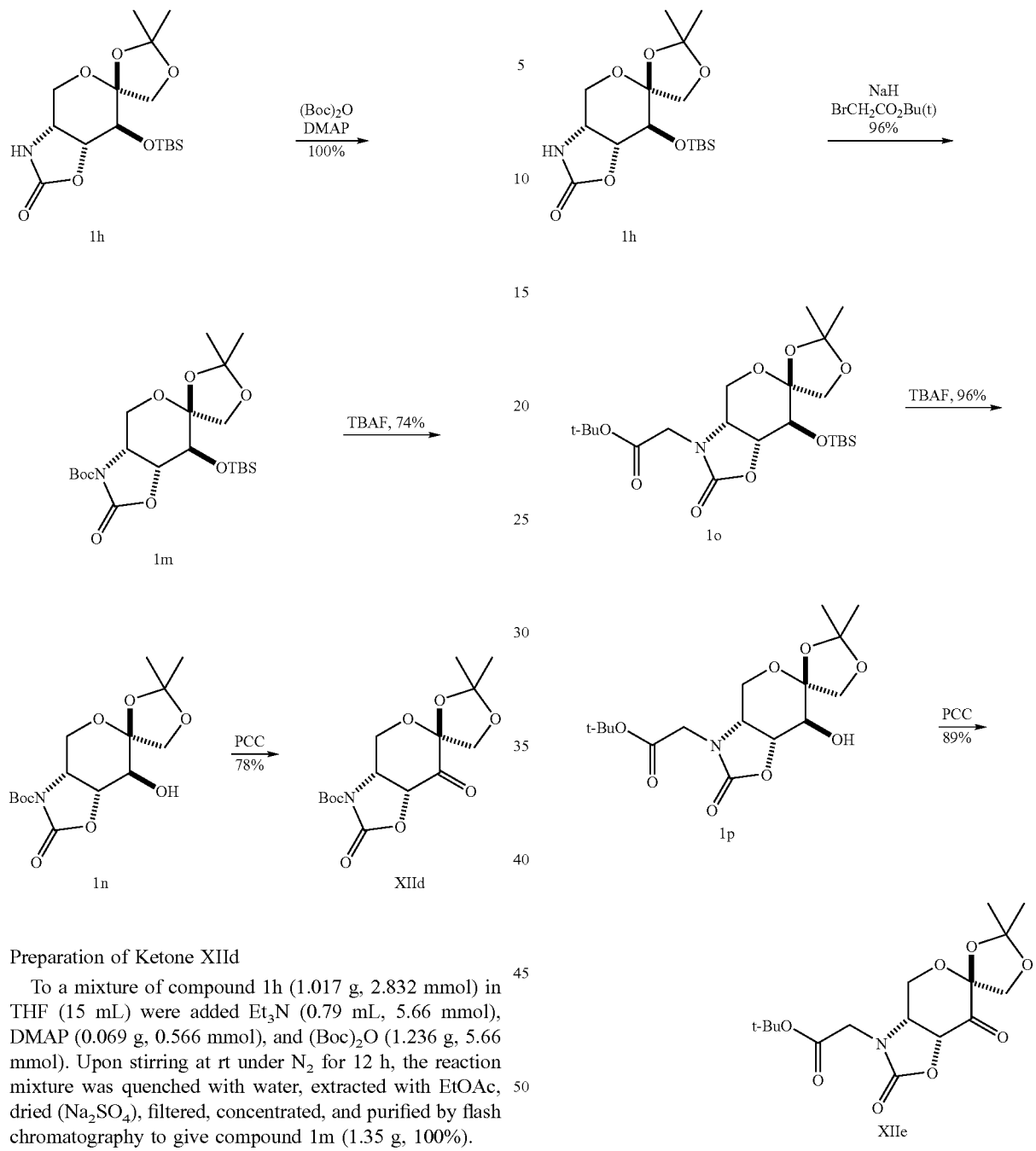

Preparation of Ketone XIId

To a mixture of compound 1h (1.017 g, 2.832 mmol) in THF (15 mL) were added Et₃N (0.79 mL, 5.66 mmol), DMAP (0.069 g, 0.566 mmol), and (Boc)₂O (1.236 g, 5.66 mmol). Upon stirring at rt under N₂ for 12 h, the reaction mixture was quenched with water, extracted with EtOAc, dried (Na₂SO₄), filtered, concentrated, and purified by flash chromatography to give compound 1m (1.35 g, 100%).

To a solution of compound 1m (1.143 g, 2.49 mmol) in THF (20 mL) was added TBAF (2.5 mL, 2.5 mmol, 1.0 M in THF) at rt under N₂. Upon stirring until no starting material was left as judged by TLC, the reaction mixture was concentrated and purified by flash chromatography to give alcohol 1n (0.634 g, 74%).

To a mixture of compound 1n (0.584 g, 1.694 mmol) and powdered 3 Å MS (1.6 g) in CH₂Cl₂ (7.3 mL) was added PCC (0.84 g, 3.90 mmol) portionwise over 15 min. Upon stirring at rt under N₂ for 3 h, the reaction mixture was filtered through celite and washed with Et₂O. The filtrate was concentrated and purified by flash chromatography to give ketone XIId (0.453 g, 78%).

Preparation of Ketone XIIe

To a solution of compound 1h (1.0 g, 2.786 mmol) in THF (20 mL) was added NaH (0.134 g, 3.3 mmol) at 0° C. under N₂. After the reaction mixture was stirred at 0° C. for 0.5 h, BrCH₂CO₂Bu(t) (0.652 g, 3.3 mmol) was added. Upon stirring for additional 12 h, the reaction mixture was quenched with water, extracted with EtOAc, dried (Na₂SO₄), filtered, concentrated, and purified by flash chromatography to give compound 1o (1.26 g, 96%).

To a solution of compound 1o (1.2 g, 2.54 mmol) in THF (25 mL) was added TBAF (2.55 mL, 2.55 mmol, 1.0 M in THF). Upon stirring at rt until no starting material was left as judged by TLC, the reaction mixture was quenched with water, extracted with EtOAc, dried (Na$_2$SO$_4$), filtered, concentrated, and purified by flash chromatography to give alcohol 1p (0.876 g, 96%).

To a solution of alcohol 1p (0.85 g, 2.37 mmol) in CH$_2$Cl$_2$ (10 mL) were added 3 Å MS (2.2 g) and PCC (1.2 g, 5.57 mmol). Upon stirring at rt for 12 h, the reaction mixture was passed through a short silica gel column. The filtrate was concentrated and purified by flash chromatography to give ketone XIIe (0.755 g, 89%).

Example 2

This example illustrates a method for synthesizing a variety of compounds of Formula IV.

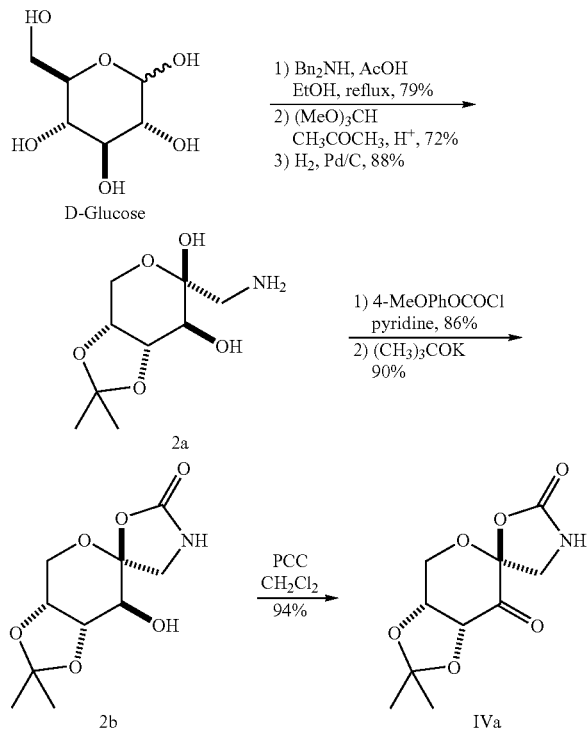

Preparation of Aminodiol 2a

To a suspension of D-glucose (36.0 g, 200.0 mmol) and Bn$_2$NH (39.5 g, 200.0 mmol) in absolute EtOH (200 mL) was added AcOH (12.0 g, 200.0 mmol). Upon refluxing for 3 h, the reaction mixture was cooled and filtered with suction. The resulting filter cake was washed with EtOH to colorless and dried in a desiccator over calcium chloride to give 1-dibenzylamino-1-deoxy-D-fructose as a white solid (57.0 g, 79%).

To a suspension of 1-dibenzylamino-1-deoxy-D-fructose (2.5 g, 6.96 mmol), trimethyl orthoformate (2.0 mL, 18.3 mmol) in acetone (80 mL) at 0° C. was added conc: HCl (0.6 mL). Upon stirring at 0° C. for 2 h, the reaction mixture was neutralized with NH$_4$OH, filtered, concentrated, and purified by flash chromatography to give the dibenzylaminodiol as a syrup (2.01 g, 72%): $[\alpha]^{20}{}_D$=−87.9 (c, 0.655, CHCl$_3$); IR (KBr) 3446 cm$^{-1}$; $^1$H NMR δ7.42–7.24 (m, 10H), 4.22–3.91 (m, 6H), 3.52–3.48 (m, 2H), 3.30 (d, J=7.5 Hz, 1H), 3.08 (d, J=13.6 Hz, 1H), 2.71 (d, J=13.6 Hz, 1H), 1.53 (s, 3H), 1.36 (s, 3H); $^{13}$C NMR δ138.2, 129.2, 128.4, 127.3, 109.0, 96.4, 77.5, 73.7, 72.1, 59.1, 58.8, 56.6, 28.2, 26.3. Anal. Calcd for C$_{23}$H$_{29}$NO$_5$: C, 69.15; H, 7.32; N, 3.51. Found: C, 69.38; H, 7.28; N, 3.49.

A solution of dibenzylaminodiol (15.0 g, 37.41 mmol) in ethanol (250 mL) was purged with N$_2$, and 10% Pd/C (2.5 g) was added. Upon stirring under H$_2$ at room temperature overnight, the reaction mixture was filtered through a short silica gel column and concentrated. The resulting residue was recrystallized from CH$_2$Cl$_2$-hexane in a freezer to give aminodiol 2a as a white crystal (7.25 g, 88%): mp 100–103° C.; $[\alpha]^{20}{}_D$=−158.1 (c 0.21, CHCl$_3$); IR (KBr) 3470, 3361, 1216 cm$^{-1}$; $^1$H NMR δ4.24–4.12 (m, 3H), 3.94 (d, J=13.5 Hz, 1H), 3.47 (d, J=6.9 Hz, 1H), 2.95 (d, J=11.7 Hz, 1H), 2.89 (d, J=11.7 Hz, 1H), 1.55 (s, 3H), 1.38 (s, 3H); $^{13}$C NMR δ109.2, 96.2, 77.7, 73.9, 72.5, 59.4, 46.3, 28.4, 26.4. Anal. Calcd for C$_9$H$_{17}$NO$_5$: C, 49.31; H, 7.82; N, 6.39. Found: C, 49.32; H, 7.60; N, 6.20.

Preparation of Alcohol 2b

To a solution of 2a (17.15 g, 78.31 mmol) and pyridine (100 mL) in CH$_2$Cl$_2$ (350 mL) was added dropwise 4-methoxyphenyl chloroformate (16.07 g, 86.14 mmol) at 0° C. Upon stirring at 0° C. for 5 h, the reaction mixture was quenched with water, extracted with EtOAc, dried (Na$_2$SO$_4$), filtered, concentrated, and purified by flash chromatography to give the carbamate as a colorless oil (24.71 g, 86%): $[\alpha]^{20}{}_D$=−93.71 (c 0.53, CHCl$_3$); IR (KBr) 3356, 1719, 1205 cm$^{-1}$; $^1$H NMR δ7.02 (m, 2H), 6.87 (m, 2H), 5.65 (dd, J=7.2, 6.0 Hz, 1H,), 4.23–4.16 (m, 3H), 3.99 (d, J=12.9 Hz, 1H), 3.79 (s, 3H), 3.62 (d, J=6.0 Hz, 1H), 3.56 (dd, J=14.7, 7.2 Hz, 1H), 3.40 (dd, J=14.7, 6.0 Hz, 1H), 1.55 (s, 3H), 1.38 (s, 3H); $^{13}$C NMR δ157.1, 144.2, 122.4, 114.4, 109.2, 96.7, 76.2, 73.3, 70.9, 60.0, 55.7, 47.3, 28.2, 26.1.

To a solution of the carbamate (10.4 g, 28.01 mmol) in CH$_3$CN (125 mL) was added (CH$_3$)$_3$COK (0.38 g, 3.39 mmol). Upon stirring at room temperature for 0.5 h, the reaction mixture was concentrated and purified by flash chromatography to give alcohol 2b as a white solid (6.15 g, 90%): mp 171–173° C.; $[\alpha]^{20}{}_D$=−146.25 (c 0.12, CHCl$_3$); IR (KBr) 3346, 1760, 1077 cm$^{-1}$; $^1$H NMR (CD$_3$OD) δ4.37–4.34 (m, 1H), 4.27–4.21 (m, 2H), 4.10 (d, J=13.8 Hz, 1H), 3.83 (d, J=9.9 Hz, 1H), 3.64 (d, J=7.8 Hz, 1H), 3.36 (d, J=9.9 Hz, 1H), 1.53 (s, 3H), 1.40 (s, 3H); $^{13}$C NMR (CD$_3$OD) δ160.7, 111.2, 107.1, 78.6, 75.5, 73.0, 63.3, 50.1, 29.3, 27.3. Anal. Calcd for C$_{10}$H$_{15}$NO$_6$: C, 48.98; H, 6.17; N, 5.71.

Found: C, 49.12; H, 6.15; N, 5.67.

Preparation of Ketone IVa

To a mixture of alcohol 2b (1.07 g, 4.37 mmol) and powdered 3 Å MS (4.0 g) in CH$_2$Cl$_2$ (19 mL) was added PCC (2.16 g, 10.02 mmol) portionwise over 15 min. Upon stirring under N$_2$ for 3 h, the reaction mixture was filtered through celite and washed with Et$_2$O. The filtrate was concentrated and purified by flash chromatography to give the ketone IVa as a white solid (0.997 g, 94%): mp 144.5–145.5° C.; $[\alpha]^{20}{}_D$=−118.0 (c 0.27, CHCl$_3$); IR (KBr) 3378, 3319, 1759, 1731 cm$^{-1}$; $^1$H NMR (CDCl$_3$) δ6.51 (s, 1H), 4.84 (d, J=5.4 Hz, 1H), 4.66–4.52 (m, 2H), 4.32 (d, J=10.7 Hz, 1H), 4.23 (d, J=13.5 Hz, 1H), 3.38 (d, J=10.7 Hz, 1H), 1.46 (s, 3H), 1.42 (s, 3H); $^{13}$C NMR (CDCl$_3$) δ195.2, 156.0, 111.0, 102.7, 77.5, 75.5, 61.0, 45.3, 27.2, 26.1. HRMS Calcd C$_{10}$H$_{14}$NO$_6$ (M$^+$+1): 244.0821.

Found: 244.0824. Anal. Calcd for C$_{10}$H$_{13}$NO$_6$.0.7H$_2$O: C, 46.95; H, 5.67; N, 5.48.

Found: C, 47.16; H, 5.86; N, 5.43.

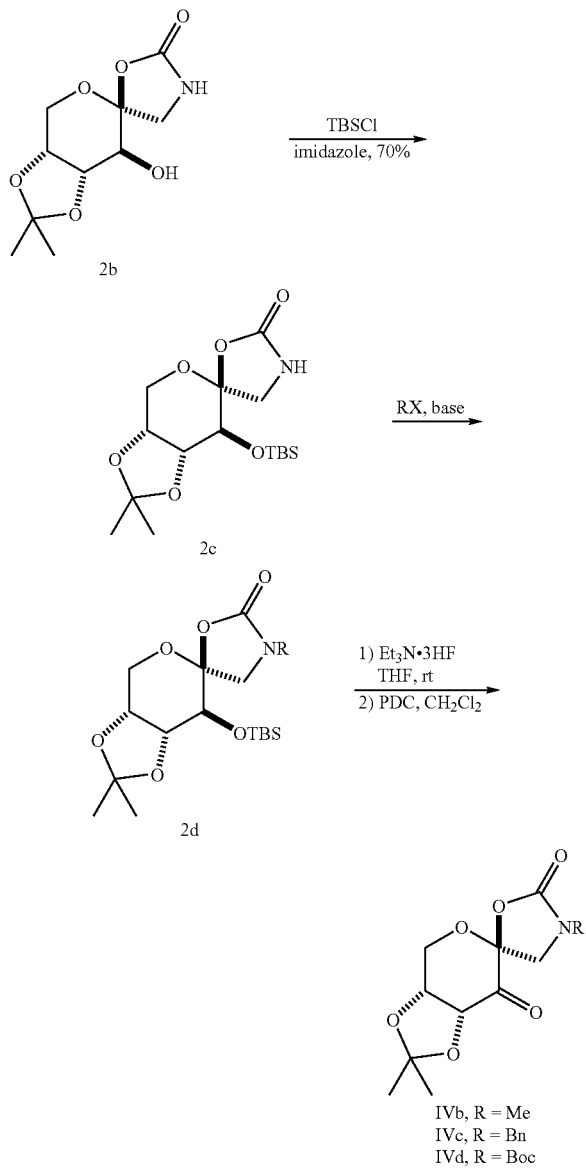

2b

2c

2d

IVb, R = Me
IVc, R = Bn
IVd, R = Boc

Preparation of TBS Ether 2c

To a solution of alcohol 2b (10.4 g, 42.45 mmol) in CH$_3$CN (300 mL) were added imidazole (4.33 g, 63.67 mmol) and TBSCl (6.72 g, 44.57 mmol). Upon stirring at room temperature for 24 h, the reaction mixture was quenched with water, extracted with EtOAc, dried (Na$_2$SO$_4$), filtered, concentrated, and purified by flash chromatography to give TBS ether 2c as a white solid (10.66 g, 70%): mp 153–155° C.; [α]$^{20}_D$=−92.92 (c 0.12, CHCl$_3$); IR (KBr) 3286, 1770 cm$^{-1}$; $^1$H NMR δ5.87 (s, 1H), 4.31–4.18 (m, 3H), 4.08 (d, J=12.9 Hz, 1H), 3.68 (d, J=9.3 Hz, 1H), 3.65 (d, J=6.6 Hz, 1H), 3.39 (dd, J=9.3, 1.0 Hz, 1H), 1.53 (s, 3H), 1.36 (s, 3H), 0.87 (s, 9H), 0.17 (s, 3H, Me), 0.098 (s, 3H); $^{13}$C NMR δ157.8, 109.3, 104.9, 77.0, 73.5, 73.3, 61.9, 48.9, 28.4, 26.4, 25.9, 18.2, −3.7, −5.2. Anal. Calcd for C$_{16}$H$_{29}$NO$_6$Si: C, 53.46; H, 8.13; N, 3.90. Found: C, 53.58; H, 7.89; N, 4.03.

Preparation of Ketone IVb

To a solution of TBS ether 2c (2.0 g, 5.57 mmol) in THF (20 mL) was added NaH (0.267 g, 6.685 mmol) at 0° C. under N$_2$. Upon stirring for 0.5 h, MeI (1.58 g, 11.14 mmol) was added. After being stirred for 12 h, the reaction mixture was quenched with water, extracted with EtOAc, dried (Na$_2$SO$_4$), filtered, concentrated, and purified by chromatography to give 2d (R=Me) as a white solid (2.04 g, 98%): mp 107–108° C.; [α]$^{20}_D$=−62.5 (c 0.20, CHCl$_3$); IR (KBr) 1773 cm$^{-1}$; $^1$H NMR δ4.37–4.18 (m, 3H), 4.09 (d, J=13.2 Hz, 1H), 3.65 (d, J=6.3 Hz, 1H), 3.61 (d, J=9.3 Hz, 1H), 3.34 (d, J=9.3 Hz, 1H), 2.87 (s, 3H), 1.54 (s, 3H), 1.37 (s, 3H), 0.86 (s, 9H), 0.18 (s, 3H), 0.10 (s, 3H); $^{13}$C NMR δ156.4, 109.4, 101.5, 77.1, 73.6, 73.4, 61.9, 54.8, 30.6, 28.5, 26.5, 25.8, 18.2, −3.7, −5.2. Anal. Calcd for C$_{17}$H$_{31}$NO$_6$Si: C, 54.66; H, 8.37; N, 3.75. Found: C, 54.72; H, 8.26; N, 3.70.

To a solution of TBS ether 2d (R=Me) (2.04 g, 5.47 mmol) in THF (20 mL) was added TBAF (1.0 M in THF) (5.5 mL, 5.5 mmol). Upon stirring at room temperature to the completion as judged by TLC, the reaction mixture was quenched with water, extracted with EtOAc, dried (Na$_2$SO$_4$), filtered, concentrated, and purified by flash chromatography to give the alcohol as a white solid (1.42 g, 99%). mp 144–146° C.; [α]$^{20}_D$=−158.8 (c 0.08, CHCl$_3$); IR (KBr) 3422, 1747 cm$^{-1}$; $^1$H NMR δ4.31–4.23 (m, 3H), 4.10 (d, J=12.9 Hz, 1H), 3.82 (d, J=9.6 Hz, 1H), 3.71–3.65 (m, 1H), 3.36 (d, J=9.6 Hz, 1H), 2.99–2.93 (m, 1H), 2.90 (s, 3H), 1.55 (s, 3H), 1.39 (s, 3H); $^{13}$C-NMR δ156.3, 110.0, 101.4, 76.7, 73.4, 71.8, 61.8, 54.6, 30.8, 28.3, 26.2. Anal. Calcd for C$_{11}$H$_{17}$NO$_6$: C, 50.96; H, 6.61; N, 5.40. Found: C, 50.77; H, 6.40; N, 5.30.

To a solution of the above alcohol (0.145 g, 0.56 mmol) in CH$_2$Cl$_2$ (5 mL) were added PDC (0.32 g, 0.84 mmol), 3 Å MS (0.5 g), and AcOH (1 drop). Upon stirring at room temperature for 6 h, EtOAc was added. The resulting mixture was passed through a short silica gel plug, concentrated, and purified by flash chromatography to give ketone IVb (0.144 g, 99%): [α]$^{20}_D$=−50.7 (c 0.22, CHCl$_3$); IR (KBr) 3402, 1749 cm$^{-1}$; $^1$H NMR δ4.79 (d, J=5.7 Hz, 1H), 4.60–4.50 (m, 2H), 4.23 (d, J=10.2 Hz, 1H), 4.18 (d, J=13.5 Hz, 1H), 3.27 (d, J=10.5 Hz, 1H), 2.91 (s, 3H), 1.42 (s, 3H), 1.38 (s, 3H); $^{13}$C NMR δ195.2, 154.2, 111.0, 96.6, 77.5, 75.5, 60.9, 50.9, 30.8, 27.2, 26.1. HRMS calcd for C$_{11}$H$_{16}$NO$_6$(M$^+$+1): 258.0978. Found: 258.0979.

Preparation of Ketone IVc

TBS ether 2d (R=Bn) was prepared from 5(2.0 g, 5.57 mmol) in a way similar to 2d (R=Me): white solid (2.49 g, 99%); mp 101–103° C.; [α]$^{20}_D$=−64.8 (c 0.16, CHCl$_3$); IR (KBr) 1769 cm$^{-1}$; $^1$H NMR δ7.46–7.23 (m, 5H), 4.49 (d, J=15.0 Hz, 1H), 4.35 (d, J=15.0 Hz, 1H), 4.31–4.18 (m, 3H), 4.06 (d, J=13.5 Hz, 1H), 3.61 (d, J=6.6 Hz, 1H), 3.52 (d, J=9.3 Hz, 1H), 3.20 (d, J=9.3 Hz, 1H), 1.50 (s, 3H), 1.35 (s, 3H), 7.09 (s, 9H), 0.14 (s, 3H), −0.00 (s, 3H); $^{13}$C NMR δ156.4, 135.4, 129.1, 128.4, 128.2, 109.4, 102.0, 77.2, 73.4, 73.2, 61.7, 52.1, 48.2, 28.4, 26.4, 25.9, 18.1, −3.7, −5.2; Anal. Calcd for C$_{23}$H$_{35}$NO$_6$Si: C, 61.44; H, 7.85; N, 3.12. Found: C, 61.30; H, 7.70; N, 3.09.

TBS ether 2d (R=Bn) (2.49 g, 5.55 mmol) was desilylated in a way similar to 2d (R=Me) to give the alcohol as a white solid (1.79 g, 96%): mp 171–172° C.; [α]$^{20}_D$=−171.4 (c 0.08, CHCl$_3$); IR (KBr) 3402, 1751 cm$^{-1}$; $^1$H NMR δ7.40–7.23 (m, 5H), 4.46 (s, 2H), 4.33–4.21 (m, 3H), 4.10 (d, J=12.9 Hz, 1H), 3.67 (d, J=9.6 Hz, 1H), 3.68–3.61 (m, 1H), 3.25 (d, J=9.6 Hz, 1H), 1.50 (s, 3H), 1.37 (s, 3H). Anal. Calcd for C$_{17}$H$_{21}$NO$_6$: C, 60.89; H, 6.31; N, 4.18. Found: C, 60.90; H, 6.13; N4.14.

The above alcohol (0.041 g, 0.122 mmol) was oxidized with PDC to give ketone IVc as a white solid (0.038 g, 93%): mp 176–178° C.; $[\alpha]^{20}_D$=−85.7 (c 0.15, CHCl$_3$); IR (KBr) 3394, 1756 cm$^{-1}$; $^1$H NMR δ7.36–7.13 (m, 5H), 4.74 (d, J=5.7 Hz, 1H), 4.57–4.30 (m, 4H), 4.12 (d, J=13.2 Hz, 1H), 4.05 (d, J=10.2 Hz, 1H), 3.10 (d, J=10.2 Hz, 1H), 1.34 (s, 3H), 1.33 (s, 3H); $^{13}$C NMR δ195.1, 154.2, 134.6, 129.0, 128.3, 128.0, 111.0, 100.0, 77.5, 75.5, 61.0, 48.5, 48.2, 27.2, 26.1. Anal. Calcd for C$_{17}$H$_{19}$NO$_6$.0.4H$_2$O: C, 59.96; H, 5.82; N 4.12. Found: C, 59.78; H, 5.89; N 4.16.

Preparation of Ketone IVd

To a solution of TBS ether 2c (2.0 g, 5.57 mmol) in THF (20 mL) were added Et$_3$N (2.82 g, 27.86 mmol), DMAP (0.136 g, 1.11 mmol), and (Boc)$_2$O (2.43 g, 11.14 mmol). Upon stirring at room temperature for 24 h, the reaction mixture was quenched with water, extracted with EtOAc, dried (Na$_2$SO$_4$), filtered, concentrated, and purified by flash chromatography to give TBS ether 2d (R=Boc) as a white solid (2.53 g, 99%/O): mp 114–115 ° C.; $[\alpha]^{20}_D$=−67.7 (c 0.118, CHCl$_3$); IR (KBr) 1828, 1808, 1727 cm$^{-1}$; $^1$H NMR δ4.27–4.08 (m, 4H), 3.94 (d, J=10.8 Hz, 1H), 3.68 (d, J=10.8 Hz, 1H), 3.65 (d, J=6.9 Hz, 1H), 1.52 (s, 3H), 1.50 (s, 9H), 0.84 (s, 9H), 0.17 (s, 3H), 0.11 (s, 3H); $^{13}$C NMR δ150.3, 148.8, 109.4, 101.1, 84.0, 76.8, 73.8, 73.1, 62.3, 51.8, 28.4, 28.1, 26.4, 25.8, 18.1, −3.7, −5.3; Anal. Calcd for C$_{23}$H$_{37}$NO$_8$Si: C, 54.88; H, 8.11; N, 3.05. Found: C, 54.77; H, 7.98; N, 3.05.

To a solution of TBS ether 2d (R=Boc) (6.43 g, 14.0 mmol) in THF (100 mL) was added Et$_3$N.3HF (22.6 g, 140.0 mmol). Upon stirring at room temperature to the completion as judged by TLC (about 4 days), the reaction mixture was quenched with water, extracted with EtOAc, dried (Na2SO$_4$), filtered, concentrated, and purified by flash chromatography to give the alcohol as a white solid (4.47 g, 93%): mp 120.0–121.5° C.; $[\alpha]^{20}_D$=−113.9(c 0.33, CHCl$_3$); IR (KBr) 3481, 1812, 1733, 1718, 1222, 1162cm$^{-1}$; $^1$H NMR δ4.26–4.23 (m, 3H), 4.13 (d, J=11.2 Hz, 1H), 4.12 (d, J=12.8 Hz, 1H), 3.75 (d, J=11.2 Hz, 1H), 3.76–3.70 (m, 1H), 2.74 (d, J=6.8 Hz, 1H, OH), 1.53 (s, 3H), 1.52 (s, 9H), 1.37 (s, 3H); $^{13}$C NMR δ150.5, 148.9, 109.9, 101.0, 84.3, 76.4, 73.1, 71.2, 62.0, 51.4, 28.2, 28.1, 26.2.

The above alcohol (1.9 g, 5.51 mmol) was oxidized with PDC to give ketone IVd as a white solid (1.52 g, 80%): mp 139–140° C.; $[\alpha]^{20}_D$=−47.9 (c 0.83, CHCl$_3$); IR (KBr) 3446 (hydrate), 1823, 1756,1731 cm$^{-1}$; $^1$H NMR δ4.79 (d, J=5.6 Hz, 1H), 4.61 (dd, J=5.6, 1.8 Hz, 1H), 4.56 (d, J=11.6 Hz, 1H), 4.51 (dd, J=13.6, 1.8 Hz, 1H), 4.23 (d, J=13.6 Hz, 1H), 3.71 (d, J=11.6 Hz, 1H), 1.53 (s, 9H), 1.45 (s, 3H), 1.41 (s, 3H); $^{13}$C NMR δ194.9, 149.0, 148.6, 111.3, 98.9, 85.0, 77.4, 75.5, 61.3, 48.4, 28.0, 27.2, 26.0; Anal. Calcd for C$_{15}$H$_{21}$NO$_8$: C, 52.47; H, 6.17; N, 4.08. Found: C, 52.32; H, 5.94; N, 3.97.

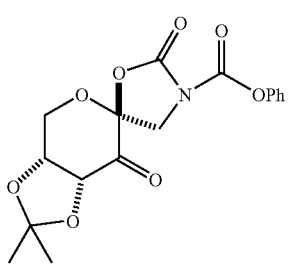

IVe

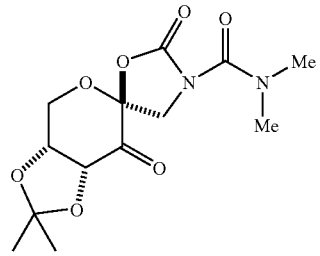

IVf

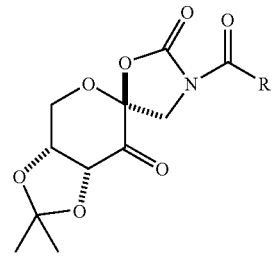

IVg R = CH$_3$
IVh R = t-Bu

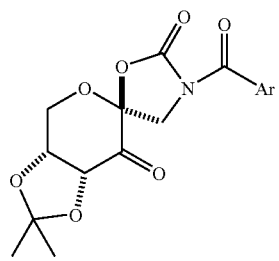

IVi Ar = Ph
IVj Ar = 4-MeO—Ph
IVk Ar = 2-MeO—Ph
IVl Ar = 2,4-(MeO)$_2$—Ph
IVm Ar = 2,6-(MeO)$_2$—Ph

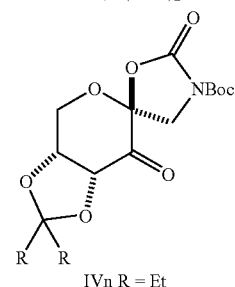

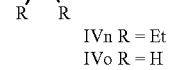

IVn R = Et
IVo R = H

Preparation of Ketone IVe

To a solution of TBS ether 2c (0.718 g, 2.0 mmol) in THF (20 mL) were added Et$_3$N (1.0 g, 10.0 mmol), DMAP (0.024 g, 0.2 mmol), and PhOCOCl (0.47 g, 3.0 mmol) at 0° C. under N$_2$. Upon stirring to the completion as judged by TLC (about 2 h), the reaction mixture was quenched with water, extracted with EtOAc, dried (Na$_2$SO$_4$), filtered, concentrated, and purified by flash chromatography to give compound 2d (where R is —C(=O)OPh) as a white solid (0.95 g, 99%): mp 123–125° C.; $[\alpha]^{20}_D$=−47.6(c 1.19, CHCl$_3$); IR (KBr) 1839, 1806, 1743 cm$^{-1}$; $^1$H NMR δ7.47–7.41 (m, 2H), 7.33–7.29 (m, 1H), 7.20–7.17 (m, 2H), 4.37–4.19 (m, 4H), 4.19 (d, J=11.0 Hz, 1H), 3.95 (d, J=11.0 Hz, 1H), 3.77

(d, J=6.9 Hz, 1H), 1.59 (s, 3H), 1.43 (s, 3H), 0.94 (s, 9H), 0.25 (s, 3H), 0.19 (s, 3H); $^{13}$C NMR δ150.0, 149.8, 149.0, 129.7, 126.6, 121.4, 109.6, 101.9, 76.8, 73.9, 73.0, 62.6, 52.1, 28.5, 26.5, 25.9, 18.2, −3.9, −5.2.

TBS ether 2d (where R is —C(=O)OPh) (0.63 g, 1.32 mmol) was desilylated with Et$_3$N.3HF (1.06 g, 6.58 mmol) in a way similar to 2d (where R is Boc) to give the alcohol as a white solid (0.372 g, 78%) (about 3 days): mp 185–186° C.; $[α]^{20}{}_D$=−101.8° (c 1.02, CHCl$_3$); IR (KBr) 3474, 1829, 1744 cm$^{-1}$; $^1$H NMR δ7.39–7.32 (m, 2H), 7.26–7.19 (m, 1H), 7.17–7.12 (m, 2H), 4.32–4.11 (m, 5H), 3.92 (d,J=10.8 Hz, 1H), 3.76 (m, 1H), 2.99 (s, 1H), 1.51 (s, 3H), 1.36 (s, 3H); $^{13}$C NMR δ150.0, 149.0, 129.6, 126.6, 121.4, 110.1, 101.7, 76.3, 73.0, 71.4, 62.4, 51.7, 28.3, 26.3. Anal. Calcd for C$_{17}$H$_{19}$NO$_8$: C, 55.89; H, 5.24; N, 3.83. Found: C, 56.03; H, 5.40; N, 3.95.

The above alcohol (0.255 g, 0.70 mmol) was oxidized with PDC to give ketone IVe as a white solid (0.25 g, 96%): mp: 190–191° C.; $[α]^{20}{}_D$=−55.0° (c 0.93, CHCl$_3$); IR (KBr) 1843, 1759, 1720 cm$^{-1}$; $^1$H NMR δ7.45–7.38 (m, 2H), 7.32–7.26 (m, 1H), 7.22–7.18 (m, 2H), 4.83 (d, J=5.4 Hz, 1H), 4.78 (d, J=11.5 Hz, 1H), 4.65 (m, 1H), 4.55 (dd, J=13.7, 2.1 Hz, 1H), 4.29 (d, J=13.7 Hz, 1H), 3.95 (d, J=11.5 Hz, 1H), 1.48 (s, 3H), 1.44 (s, 3H); $^{13}$C NMR δ194.5, 149.9, 148.4, 129.7, 126.8, 121.3, 111.5, 99.5, 77.3, 75.4, 61.7, 48.8, 27.3, 26.2. Anal. Calcd for C$_{17}$H$_{17}$NO$_8$: C, 56.20; H, 4.72; N, 3.86. Found: C, 56.12; H, 4.73; N, 3.82.

Preparation of Ketone IVf

To a solution of 2c (0.718 g, 2.0 mmol) in THF (20 mL) was added Et$_3$N (2.02 g, 20.0 mmol), DMAP (0.024 g, 0.2 mmol), and Me$_2$NCOCl (0.43 g, 4.0 mmol) at 0° C. under N$_2$. Upon stirring to the completion as judged by TLC (about 12 h), the reaction mixture was quenched with water, extracted with EtOAc, dried (Na2SO$_4$), filtered, concentrated, and purified by flash chromatography to give compound 2d (where R is —C(=O)NMe$_2$) as a white solid (0.83 g, 96%): mp 129–131° C.; $[α]^{20}{}_D$=−85.0° (c 0.81, CHCl$_3$); IR (KBr) 1782, 1688 cm$^{-1}$; $^1$H NMR δ4.26–4.05 (m, 5H), 3.71–3.68 (m, 2H), 2.99 (s, 6H), 1.52 (s, 3H), 1.35 (s, 3H), 0.86 (s, 9H), 0.16 (s, 3H), 0.11 (s, 3H); $^{13}$C NMR δ152.8, 152.1, 109.4, 102.7, 76.8, 73.0, 72.8, 62.0, 51.7, 28.2, 26.3, 25.9, 18.2, −3.8, −5.1.

TBS ether 2d (where R is —C(=O)NMe$_2$) (0.617 g, 1.435 mmol) was desilylated with Et$_3$N.3HF (2.31 g, 14.35 mmol) in a way similar to 2d (where R is Boc) to give the alcohol as a white solid (0.346 g, 76%) (about 3 days): mp 167–169° C.; $[α]^{20}{}_D$=−102.3° (c 0.87, CHCl$_3$); IR (KBr) 3428, 1783, 1683 cm$^{-1}$; $^1$H NMR δ4.31 (d, J=10.4 Hz, 1H), 4.28–4.23 (m, 3H), 4.12 (d, J=13.5 Hz, 1H), 3.78 (m, 1H), 3.66 (d, J=10.4 Hz, 1H), 3.20 (bs, 1H), 3.01 (s, 6H), 1.54 (s, 3H), 1.38 (s, 3H); $^{13}$C NMR δ153.0, 152.0, 109.9, 102.6, 76.2, 73.0, 71.2, 62.2, 51.7, 28.2, 26.2.

The above alcohol (0.217 g, 0.687 mmol) was oxidized with PDC to give ketone IVf as a white solid (0.204 g, 95%): mp 115–117° C.; $[α]^{20}{}_D$=−72.3 (c 1.11, CHCl$_3$); IR (KBr) 3409, 1789, 1760, 1688 cm$^{-1}$; $^1$H NMR δ4.80 (d, J=5.4, 1H), 4.65–3.94 (m, 4H), 3.70 (d, J=11.1 Hz, 1H), 3.03 (s, 6H), 1.47 (s, 3H), 1.41 (s, 3H). Anal. Calcd for C$_{13}$H$_{18}$N$_2$O$_7$.0.4H$_2$O: C, 48.56; H, 5.85; N, 8.72. Found: C, 48.85; H, 5.97; N8.46.

Preparation of Ketone 2g

To a solution of 2c (0.718 g, 2.0 mmol) in THF (20 mL) were added Et$_3$N (1.0 g, 10.0 mmol), DMAP (0.024 g, 0.2 mmol), and CH$_3$COCl (0.236 g, 3.0 mmol) at 0° C. under N$_2$. Upon stirring to the completion as judged by TLC (about 12 h), the reaction mixture was quenched with water, extracted with EtOAc, dried (Na$_2$SO$_4$), filtered, concentrated, and purified by flash chromatography to give compound 2d (where R is —C(=O)CH$_3$) as a white solid (0.727 g, 91%): mp 76–78° C.; $[α]^{20}{}_D$=−64.0 (c 0.97, CHCl$_3$); IR (KBr) 1794, 1709 cm$^{-1}$; $^1$H NMR δ4.28–4.13 (m, 4H), 3.99 (d, J=11.5 Hz, 1H), 3.76 (d, J=11.5 Hz, 1H), 3.69 (d, J=6.9 Hz, 1H), 2.50 (s, 3H), 1.55 (s, 3H), 1.38 (s, 3H), 0.83 (s, 9H), 0.19 (s, 3H), 0.10 (s, 3H); $^{13}$C NMR δ169.9, 151.9, 109.6, 102.2, 76.8, 73.9, 73.0, 62.6, 51.2, 28.5, 26.5, 25.8, 23.7, 18.1, −3.6, −5.2. Anal. Calcd for C$_{18}$H$_{31}$NO$_7$Si: C, 53.84; H, 7.78; N, 3.49. Found: C, 54.03; H, 7.74; N, 3.41.

TBS ether 2d (where R is —C(=O)CH$_3$) (0.65 g, 1.62 mmol) was desilylated with Et$_3$N.3HF (0.523 g, 3.24 mmol) in a way similar to 2d (where R is Boc) to give the alcohol as a colorless oil (0.267 g, 57%) (about 5 days): $[α]^{20}{}_D$=−143.2 (c 0.9, CHCl$_3$); IR (KBr) 3447, 1793, 1709 cm$^{-1}$; $^1$H NMR δ4.28–4.17 (m, 4H), 4.15 (d, J=11.7 Hz, 1H), 3.82 (d, J=11.7 Hz, 1H), 3.75 (d, J=5.7 Hz, 1H), 3.21 (s, 1H), 2.51 (s, 3H), 1.54 (s, 3H), 1.38 (s, 3H); $^{13}$C NMR δ170.2, 151.9, 110.1, 101.9, 76.4, 73.1, 71.4, 62.3, 50.6, 28.3, 26.3, 23.8. Anal. Calcd for C$_{12}$H$_{17}$NO$_7$: C, 50.17; H, 5.96; N, 4.88. Found: C, 50.09; H, 5.70; N, 4.77.

The above alcohol (0.18 g, 0.627 mmol) was oxidized with PDC to give ketone IVg as a colorless oil (0.177 g, 99%): $[α]^{20}{}_D$=−56.8 (c 2.77, CH$_3$CN); IR (KBr) 3427 (hydrate), 1798, 1711 cm$^{-1}$; Ketone: $^1$H NMR (CD$_3$CN) δ4.85 (d, J=6.0 Hz, 1H), 4.43–4.15 (m, 3H), 3.71 (d, J=12.3 Hz, 1H), 3.61 (d, J=12.3 Hz, 1H), 2.40 (s, 3H), 1.47 (s, 3H), 1.40 (s, 3H); $^{13}$C NMR (CD$_3$CN) δ196.3, 170.5, 152.4, 111.7, 103.1, 78.2, 76.1, 62.8, 48.9, 27.2, 26.0, 23.7; Hydrate: $^1$H NMR (CD$_3$CN) δ4.67 (d, J=5.1 Hz, 1H), 4.43–4.15 (m, 4H), 3.81 (d, J=12.7 Hz, 1H), 2.40 (s, 3H), 1.36 (s, 3H), 1.33 (s, 3H); $^{13}$C NMR (CD$_3$CN) δ170.5, 151.5, 110.5, 100.4, 92.0, 76.6, 73.8, 64.5, 51.6, 26.5, 24.8, 23.8. HRMS calcd for C$_{12}$H$_{18}$NO$_8$ (M.H$_2$0 +1): 304.1032. Found: 304.1026.

Preparation of Ketone IVh

To a solution of 2c (0.718 g, 2.0 mmol) in CH$_2$Cl$_2$ (20 mL) were added Et$_3$N (1.0 g, 10.0 mmol), DMAP (0.024 g, 0.2 mmol), and Me$_3$CCOCl (0.326 g, 3.0 mmol) at 0° C. under N$_2$. Upon stirring to the completion as judged by TLC (about 12 h), the reaction mixture was quenched with water, extracted with EtOAc, dried (Na$_2$SO$_4$), filtered, concentrated, and purified by flash chromatography to give compound 2d (where R is —C(=O)C(CH$_3$)$_3$) as a white solid (0.884 g, 99%): mp 145–148° C.; $[α]^{20}{}_D$=−59.2 (c 1.35, CHCl$_3$); IR (KBr) 1789, 1687 cm$^{-1}$; $^1$H NMR (CDCl$_3$) δ4.30–4.11 (m, 4H), 4.04 (d, J=11.9 Hz, 1H), 3.79 (d, J=11.9 Hz, 1H), 3.67 (d, J=6.9 Hz, 1H), 1.54 (s, 3H), 1.37 (s, 3H), 1.36 (s, 9H), 0.83 (s, 9H), 0.18 (s, 3H), 0.10 (s, 3H); $^{13}$C NMR δ177.9, 150.4, 109.6, 101.6, 76.9, 73.6, 73.1, 62.2, 53.4, 41.6, 28.5, 26.5, 26.4, 25.9, 18.2, −3.6, −5.2. Anal. Calcd for C$_{21}$H$_{37}$NO$_7$Si: C, 56.86; H, 8.41; N, 3.16. Found: C, 57.00; H, 8.35; N, 3.23.

TBS ether 2d (where R is —C(=O)C(CH$_3$)$_3$) (0.75 g, 1.69 mmol) was desilylated with Et$_3$N.3HF (0.546 g, 3.39 mmol) in a way similar to 2d (where R is Boc) to give the alcohol as a colorless oil (0.506 g, 91%) (about 5 days): $[α]^{20}{}_D$=−64.2 (c 1.15, CHCl$_3$); IR (KBr) 3458, 1793, 1691 cm$^{-1}$; $^1$H NMR δ4.28–4.12 (m, 5H), 3.84 (d, J=11.7 Hz, 1H), 3.74 (d, J=5.7 Hz, 1H), 3.06 (bs, 1H), 1.54 (s, 3H), 1.38 (s, 3H), 1.37 (s, 9H); $^{13}$C NMR δ178.2, 150.5, 110.1, 101.4, 76.4, 73.1, 71.4, 62.1, 53.1, 41.6, 28.3, 26.4, 26.2. Anal. Calcd for C$_{15}$H$_{23}$NO$_7$: C, 54.70; H, 7.04; N, 4.25. Found: C, 54.70; H, 7.11; N, 4.14.

The above alcohol (0.40 g, 1.22 mmol) was oxidized with PDC to give ketone IVh as a white solid (0.372 g, 94%): mp 156–157° C.; $[\alpha]^{20}_D$=–40.4 (c 1.95, CHCl$_3$); IR (KBr) 3468 (hydrate), 1799, 1758, 1697 cm$^{-1}$; $^1$H NMR δ4.78 (d, J=5.4 Hz, 1H), 4.62 (dd, J=5.4, 1.8 Hz, 1H), 4.58 (d, J=12.6 Hz, 1H), 4.48 (dd, J=13.5, 1.8 Hz, 1H), 4.23 (d, J=13.5 Hz, 1H), 3.82 (d, J=12.6 Hz, 1H), 1.47 (s, 3H), 1.41 (s, 3H), 1.37 (s, 9H); $^{13}$C NMR δ194.8, 177.7, 149.0, 111.5, 99.5, 77.7, 75.4, 61.6, 50.3, 41.7, 27.3, 26.3, 26.2. Anal. Calcd for C$_{15}$H$_{21}$NO$_7$: C, 55.04; H, 6.47; N, 4.28. Found: C, 55.22; H, 6.31; N, 4.32.

Preparation of Ketone IVi

To a solution of 2c (0.718 g, 2.0 mmol) in THF (20 mL) were added Et$_3$N (1.0 g, 10.0 mmol), DMAP (0.024 g, 0.2 mmol), and PhCOCl (0.422 g, 3.0 mmol) at 0 ° C. under N$_2$. Upon stirring to the completion as judged by TLC (about 12 h), the reaction mixture was quenched with water, extracted with EtOAc, dried (Na$_2$SO$_4$), filtered, concentrated, and purified by flash chromatography to give compound 2d (where R is —C(═O)CPh) as a white solid (0.867g, 94%): mp 93–95° C.; $[\alpha]^{20}_D$=–84.7 (c 1.22, CHCl$_3$); IR (KBr) 1796, 1685 cm$^{-1}$; $^1$H NMR δ7.68–7.44 (m, 5H), 4.35–4.19 (m, 5H), 4.00 (d, J=11.4 Hz, 1H), 3.81 (d, J=6.6 Hz, 1H), 1.61 (s, 3H), 1.42 (s, 3H), 0.93 (s, 9H), 0.25 (s, 3H), 0.19 (s, 3H); $^{13}$C NMR δ169.0, 151.2, 132.8, 132.3, 130.2, 129.2, 129, 127.9, 109. 6,102. 2,76.8, 73.6, 73.1, 62.5, 51.7, 28.4, 26.4, 26.0, 18.3, –3.6, –5.1.

TBS ether 2d (where R is —C(═O)CPh) (0.64 g, 1.382 mmol) was desilylated with Et$_3$N.3HF (0.569 g, 3.529 mmol) in a way similar to 2d (where R is Boc) to give the alcohol as a white solid (0.448 g, 93%/0) (about 3 days): mp 120–123° C.; $[\alpha]^{20}_D$=–134.1 (c 1.09, CHCl$_3$); IR (KBr) 3444, 1794, 1685 cm$^{-1}$; $^1$H NMR δ7.67–7.41 (m, 5H), 4.43–4.17 (m, 5H), 3.97 (d, J=11.7 Hz, 1H), 3.81 (d, J=6.6 Hz, 1H), 3.06 (bs, 1H), 1.56 (s, 3H), 1.40 (s, 3H); $^{13}$C NMR δ169.3, 151.4, 132.5, 129.1, 128, 110.1, 102.1, 76.3, 73.0, 71.4, 62.4, 51.5, 28.3, 26.2. Anal. Calcd for C$_{17}$H$_{19}$NO$_7$: C, 58.45; H, 5.48; N, 4.01. Found: C, 58.38; H, 5.46; N, 3.95.

The above alcohol (0.326 g, 0.935 mmol) was oxidized with PDC to give ketone IVi as a white solid (0.307 g, 95%/): mp 66–68° C.; $[\alpha]^{20}_D$=–91.2 (c 1.06, CHCl$_3$); IR (KBr) 3452 (hydrate), 1799, 1687 cm$^{-1}$; $^1$H NMR δ7.69–7.43 (m, 5H), 4.81 (d, J=6.3 Hz, 1H), 4.78 (d, J=12.5 Hz, 1H), 4.65 (m, 1H), 4.51 (dd, J=13.8, 2.1 Hz, 1H), 4.29 (d, J=13.8 Hz, 1H), 3.98 (d, J=12.5 Hz, 1H), 1.51 (s, 3H), 1.44 (s, 3H); $^{13}$C NMR δ194.7, 168.8, 150.0, 132.8, 132.2, 129.2, 128.1, 111.6, 99.9, 77.2, 75.4, 61.9, 48.9, 27.3, 26.2. Anal. Calcd for C$_{17}$H$_{17}$NO$_7$: C, 58.79; H, 4.93; N, 4.03. Found: C, 58.78; H, 5.12; N, 4.00.

Preparation of Ketone IVj

To a solution of 2c (0.718 g, 2.0 mmol) in THF (20 mL) were added Et$_3$N (2.6 mL, 20.0 mmol), DMAP (0.024 g, 0.2 mmol), and 4-methoxybenzoyl chloride (0.41 g, 2.4 mmol) at 0° C. under N$_2$. Upon stirring to the completion as judged by TLC (about 12 h), the reaction mixture was quenched with water, extracted with EtOAc, dried (Na$_2$SO$_4$), filtered, concentrated, and purified by flash chromatography to give compound 2d (where R is —C(═O)C[(4-OMe)Ph]) as a white solid (0.98 g, 99%): mp 139.0–140.5° C.; $[\alpha]^{20}_D$=–75.5 (c 1.78, CHCl$_3$); IR (KBr) 1794, 1680, 1607 cm$^{-1}$; $^1$H NMR δ7.69–7.64 (m, 2H), 6.93–6.89 (m, 2H), 4.32–4.15 (m, 4H), 4.22 (d, J=11.4 Hz, 1H), 3.95 (d, J=11.4 Hz, 1H), 3.86 (s, 3H), 3.76 (d, J=6.6 Hz, 1H), 1.56 (s, 3H), 1.38 (s, 3H), 0.87 (s, 9H), 0.20 (s, 3H), 0.14 (s, 3H); $^{13}$C NMR δ168.3, 163.1, 151.6, 131.8, 124.6, 113.3, 109.6, 102.1, 76.9, 73.5, 73.1, 62.4, 55.6, 51.9, 28.5, 26.5, 26.0, 18.3, –3.6, –5.0.

TBS ether 2d (where R is —C(═O)C[(4-OMe)Ph]) (0.746 g, 1.512 mmol) was desilylated with Et$_3$N.3HF (1.22 g, 7.56 mmol) in a way similar to 2d (where R is Boc) to give the alcohol as a white solid (0.489 g, 85%) (about 3 days): mp 66–68° C.; $[\alpha]^{20}_D$=–140.3 (c, 0.94, CHCl$_3$); IR (KBr) 3447, 1793, 1680, 1606 cm$^{-1}$; $^1$H NMR δ7.71–7.66 (m, 2H), 6.94–6.89 (m, 2H), 4.41–4.17 (m, 5H), 3.95 (m, 1H), 3.86 (s, 3H), 3.82 (d, J=6.0 Hz, 1H), 1.56 (s, 3H), 1.40 (s, 3H); $^{13}$C NMR δ167.5, 156.9, 150.7, 132.6, 128.8, 123.6, 120.6, 111.0, 110.1, 101.8, 76.3, 73.0., 71.6, 62.4, 56.0, 51.2, 28.3, 26.2. Anal. Calcd for C$_{18}$H$_{21}$NO$_8$: C, 56.99; H, 5.58; N, 3.69. Found: C, 56.76; H 5.74; N, 3.65.

The above alcohol (0.461 g, 1.216 mmol) was oxidized with PDC to give ketone IVj as a white solid (0.429 g, 94%): mp 63–65° C.; $[\alpha]^{20}_D$=–89.1 (c 0.96, CHCl$_3$); IR (KBr) 1799, 1758, 1684, 1606 cm$^{-1}$; $^1$H NMR δ7.72–7.69 (m, 2H), 6.96–6.92 (m, 2H), 4.81 (d, J=5.4 Hz, 1H), 4.78 (d, J=12.3 Hz, 1H), 4.65 (m, 1H), 4.52 (dd, J=2.1 Hz, 1H), 4.29 (d, J=13.5 Hz, 1H), 3.95 (d, J=12.3 Hz, 1H), 3.87 (s, 3H), 1.51 (s, 3H), 1.44 (s, 3H); $^{13}$C NMR δ194.7, 168.0, 163.5, 150.4, 132.0, 126.8, 124.0, 118.0, 113.5, 77.3, 75.5, 61.9, 55.7, 49.1, 27.3, 26.2. Anal. Calcd for C$_{18}$H$_{19}$NO$_8$: C, 57.29; H, 5.08; N, 3.71.
Found: C, 57.17; H, 5.24; N, 3.61.

Preparation of Ketone IVk

To a solution of 2c (0.718 g, 2.0 mmol) in THF (20 mL) were added Et$_3$N (2.6 mL, 20.0 mmol), DMAP (0.024 g, 0.2 mmol), and 2-methoxylbenzoyl chloride (0.41 g, 2.4 mmol) at 0° C. under N$_2$. Upon stirring to the completion as judged by TLC (about 12 h), the reaction mixture was quenched with water, extracted with EtOAc, dried (Na$_2$SO$_4$), filtered, concentrated, and purified by flash chromatography to give compound 2d (where R is —C(═O)C[(2-OMe)Ph]) as a white solid (0.9 g, 91%): mp 114–116° C.; $[\alpha]^{20}_D$=–92.0 (c 1.12, CHCl$_3$); IR (KBr) 1802, 1685, 1603 cm$^{-1}$; $^1$H NMR δ7.42 (m, 1H), 7.25 (m, 1H), 7.00 (m, 1H), 6.91 (d, J=8.4 Hz, 1H), 4.29–4.12 (m, 5H), 3.96 (d, J=11.7 Hz, 1H), 3.81 (s, 3H), 3.75 (d, J=6.6 Hz, 1H), 1.56 (s, 3H), 1.38 (s, 3H), 0.89 (s, 9H), 0.19 (s, 3H), 0.15 (s, 3H); $^{13}$C NMR δ167.4, 156.9, 150.5, 132.2, 128.4, 124, 120.5, 111, 109.6, 101.9, 76.8, 73.3, 73.1, 62.3, 55.9, 51.1, 28.4, 26.4, 26, 18.3, –3.6, –5.1.

TBS ether 2d (where R is —C(═O)C[(2-OMe)Ph]) (0.696 g, 1.411 mmol) was desilylated with Et$_3$N.3HF (1.14 g, 7.05 mmol) in a way similar to 2d (where R is Boc) to give the alcohol as a white solid (0.501 g, 94%) (about 3 days): mp 68–71° C.; $[\alpha]^{20}_D$=–119.7 (c 1.01, CHCl$_3$); IR (KBr) δ3453, 1801, 1684, 1603 cm$^{-1}$; $^1$H NMR δ7.48–7.42 (m, 1H), 7.34 (dd, J=7.8, 1.8 Hz, 1H), 7.01 (t, J=7.8 Hz, 1H), 6.92 (d, J=7.8 Hz, 4.33 (d, J=11.7 Hz, 1H), 4.29–4.15 (m, 4H), 3.99 (d, J=11.7 Hz, 1H), 3.81 (s, 3H), 3.84–3.79 (m, 1H), 1.56 (s, 3H), 1.39 (s, 3H); $^{13}$C NMR δ167.5, 156.9, 150.7, 132.6, 128.8, 123.6, 120.6, 111.0, 110.1, 101.8, 76.3, 73.0, 71.6, 62.4, 56.0, 51.2, 28.3, 26.2.

The above alcohol (0.403 g, 1.063 mmol) was oxidized with PDC to give ketone IVk as a white solid (0.391 g, 97%): mp 160–161° C.; $[\alpha]^{20}_D$=–75.0 (c 1.09, CHCl$_3$); IR (KBr) 3487 (hydrate), 1806, 1758, 1689, 1603 cm$^{-1}$; $^1$H NMR δ7.50–7.44 (m, 1H), 7.35 (dd, J=7.4, 1.4 Hz, 1H), 7.05–7.00 (m, 1H), 6.93 (d, J=8.4 Hz, 1H), 4.80 (d, J=5.4 Hz, 1H), 4.74 (d, J=12.3 Hz, 1H) 4.63 (m, 1H), 4.49 (dd, J=13.8, 2.1 Hz, 1H), 4.27 (d, J=13.8 Hz, 1H), 3.99 (d, J=12.3 Hz, 1H), 3.83 (s, 3H), 1.50 (s, 3H), 1.43 (s, 3H); $^{13}$C NMR δ194.7, 167.1, 156.9, 149.2, 132.7, 128.9, 123.1, 120.6, 111.5, 110.9, 99.7, 77.2, 75.4, 61.8, 55.9, 48.4, 27.2, 26.1. Anal. Calcd for $C_{18}H_{19}NO_8$: C, 57.29; H, 5.08; N, 3.71. Found: C, 57.17; H, 5.18; N, 3.83.

Preparation of Ketone IVL

To a solution of 2c (0.718 g, 2.0 mmol) in THF (10 mL) were added $Et_3N$ (1.01 g, 10.0 mmol), DMAP (0.024 g, 0.2 mmol), and 2,4-dimethoxybenzoyl chloride (0.482 g, 2.4 mmol) at 0° C. under $N_2$. Upon stirring to the completion as judged by TLC (about 5 h), the reaction mixture was quenched with water, extracted with EtOAc, dried ($Na_2SO_4$), filtered, concentrated, and purified by flash chromatography to give compound 2d (where R is —C(=O)C[2,4-$(OMe)_2$Ph]) as a white solid (0.973 g, 93%): mp 69–70° C.; $[\alpha]^{20}_D$=−73.8 (c 1.30, $CHCl_3$); IR (KBr) 1799, 1680, 1609 $cm^{-1}$; $^1H$ NMR δ7.32–7.29 (m, 1H), 6.54 (dd, J=8.4, 2.1 Hz, 1H), 6.48 (d, J=1.8 Hz, 1H), 4.34–4.17 (m, 5H), 3.98 (d, J=11.4 Hz, 1H), 3.87 (s, 3H), 3.83 (s, 3H), 3.78 (d, J=6.6 Hz, 1H), 1.60 (s, 3H), 1.42 (s, 3H), 0.92 )s, 9H), 0.23 (s, 3H), 0.19 (s, 3H); $^{13}C$ NMR δ167.0, 163.4, 159.0, 130.5, 116.5, 109.6, 104.7, 101.8, 98.5, 76.9, 73.3, 73.2, 62.3, 55.9, 55.7, 51.3, 28.5, 26.5, 26.0, 18.3, −3.6, −5.1.

TBS ether 2d (where R is —C(=O)C[2,4-$(OMe)_2$Ph]) (0.93 g, 1.78 mmol) was desilylated with Et3N.3HF (1.43 g, 8.89 mmol) in a way similar to 2d (where R is Boc) to give the alcohol as a white solid (0.67 g, 92%) (about 3 days): mp 70–72° C.; $[\alpha]^{20}_D$=−114.0 (c 1.00, $CHCl_3$); IR (KBr) 3447, 1797, 1676, 1609 $cm^{-1}$; $^1H$ NMR δ7.36 (d, J=8.4 Hz, 1H), 6.52 (dd, J=8.4, 2.4 Hz, 1H), 6.44 (d, J=2.4 Hz, 1H), 4.32 (d, J=11.7 Hz, 1H), 4.28–4.12 (m, 4H), 3.94 (d, J=11.7 Hz, 1H), 3.84 (s, 3H), 3.79 (m, 1H), 3.77 (s, 3H), 1.55 (s, 3H), 1.39 (s, 3H); $^{13}C$ NMR δ167.2, 163.6, 159.0, 150.9, 131.0, 116.0, 109.9, 104.8, 101.9, 98.4, 76.2, 73.0, 71.3, 62.2, 55.9, 55.6, 51.2, 28.2, 26.2.

The above alcohol (0.518 g, 1.267 mmol) was oxidized with PDC to give ketone IVl as a white solid (0.44 g, 85%): mp 74–76° C.; $[\alpha]^{20}_D$=−78.0 (c, 1.04, $CHCl_3$); IR (KBr) 1805, 1758, 1681, 1609 $cm^{-1}$; $^1H$ NMR δ7.36 (d, J=8.4 Hz, 1H), 6.53 (dd, J=8.4, 2.4 Hz, 1H), 6.44 (d, J=2.1 Hz, 1H), 4.80 (d, J=6.0 Hz, 1H), 4.72 (d, J=12.3 Hz, 1H), 4.63 (m, 1H), 4.49 (dd, J=13.5, 1.8 Hz, 1H), 4.27 (d, J=13.5 Hz, 1H), 3.97 (d, J=12.6 Hz, 1H), 3.84 (s, 3H), 3.80 (s, 3H), 1.50 (s, 3H), 1.43 (s, 3H); $^{13}C$ NMR δ194.8, 166.7, 163.9, 149.5, 131.2, 115.7, 111.6, 105.0, 99.8, 98.5, 77.3, 75.5, 61.9, 56.0, 55.7, 48.7, 27.3, 26.2.

Anal. Calcd for $C_{19}H_{21}NO_9$: C, 56.02; H, 5.20; N, 3.44. Found: C, 56.20; H, 5.34; N, 3.39.

Preparation of Ketone IVm

To a solution of 2c (0.718 g, 2.0 mmol) in THF (10 mL) were added $Et_3N$ (1.01 g, 10.0 mmol), DMAP (0.024 g, 0.2 mmol), and 2,6-dimethoxybenzoyl chloride (0.482 g, 2.4 mmol) at 0° C. under $N_2$. Upon stirring to the completion as judged by TLC (about 12 h), the reaction mixture was quenched with water, extracted with EtOAc, dried ($Na_2SO_4$), filtered, concentrated, and purified by flash chromatography to give compound 2d (where R is —C(=O)C[2,6-$(OMe)_2$Ph]) as a white solid (1.02 g, 97%): mp 63–67° C.; $[\alpha]^{20}_D$=−74.9 (c 1.07, $CHCl_3$); IR (KBr) 1800, 1698, 1598 $cm^{-1}$; $^1H$ NMR δ7.34 (t, J=8.4 Hz, 1H), 6.59 (d, J=8.4 Hz, 2H), 4.31–3.78 (m, 7H), 3.82 (s, 6H). 1.60 (s, 3H), 1.41 (s, 3H), 0.94 (s, 9H), 0.23 (s, 3H), 0.19 (s, 3H); $^{13}C$ NMR δ165.3, 157.1, 150.3, 131.5, 109.5, 103.8, 101.7, 76.9, 73.14, 73.1, 62.2, 56.1, 50.9, 28.4, 26.4, 26.0, 18.3, −3.7, −5.1.

TBS ether 2d (where R is —C(=O)C[2,6-$(OMe)_2$Ph]) (0.64 g, 1.22 mmol) was desilylated with Et3N.3HF (0.99 g, 6.12 mmol) in a way similar to 2d (where R is Boc) to give the alcohol as a white solid (0.498 g, 99%) (about 3 days): mp 75–78° C.; $[\alpha]^{20}_d$=−87.6 (c 1.02, $CHCl_3$); IR (KBr) 3447, 1799, 1694, 1597 $cm^{-1}$; $^1H$ NMR δ7.35 (t, J=8.4 Hz, 1H), 6.59 (d, J=8.4 Hz, 2H), 4.35–4.13 (m, 5H), 4.00 (d, J=11.7 Hz, 1H), 3.82 (m, 1H), 3.81 (s, 6H), 1.57 (s, 3H), 1.41 (s, 3H); $^{13}C$ NMR δ165.5, 157.2, 150.5, 131.7, 112.9, 109.9, 103.9, 101.8, 76.2, 73.0, 71.3, 62.3, 56.2, 50.8, 28.2, 26.2.

The above alcohol (0.308 g, 0.753 mmol) was oxidized with PDC to give ketone IVm as a white solid (0.268 g, 87%); mp 72–73° C.; $[\alpha]^{20}_D$=−60.6 (c, 1.12, $CHCl_3$); IR (KBr): 3481, 1805, 1758, 1698, 1597 $cm^{-1}$; $^1H$ NMR δ7.34 (t, J=8.4 Hz, 1H), 6.57 (d, J=8.4 Hz, 2H), 4.79 (d, J=5.4 Hz, 1H), 4.74 (d, J=12.3 Hz, 1H), 4.62 (m, 1H), 4.48 (dd, J=13.5, 2.1 Hz, 1H), 4.26 (d, J=13.5 Hz, 1H), 3.99 (d, J=12.3 Hz, 1H), 3.80 (s, 6H), 1.50 (s, 3H), 1.43 (s, 3H); $^{13}C$ NMR δ194.8, 157.3, 149.0, 143.8, 132.0, 112.5, 111.5, 103.9, 99.6, 77.3, 75.5, 61.8, 56.2, 48.1, 27.3, 26.2. Anal. Calcd for $C_{19}H_{21}NO_9$: C, 56.02; H, 5.20; N, 3.44. Found: C, 55.96; H, 5.26; N, 3.41.

Preparation of Ketone IVn

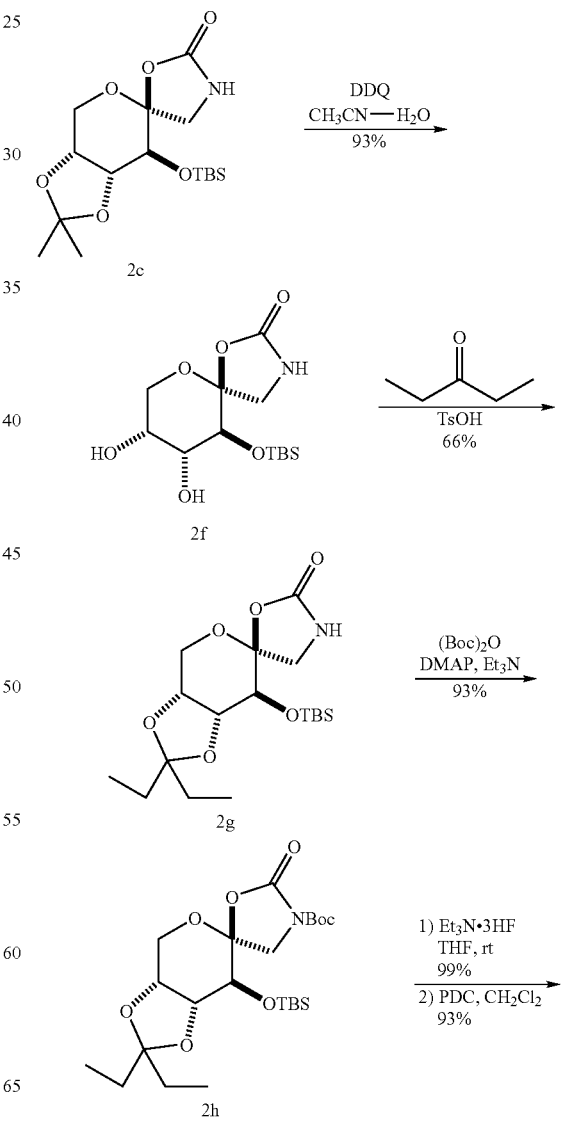

-continued

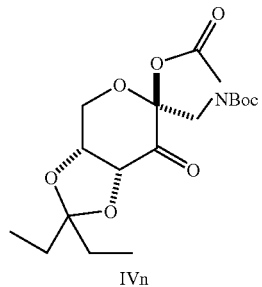

IVn

To a solution of 2c (2.48 g, 6.91 mmol) in CH$_3$CN—H$_2$O (9/1, v/v) (21 mL) was added DDQ (0.153 g, 0.691 mmol). Upon stirring at rt for 6 h, the reaction mixture was concentrated, redissolved in EtOAc, dried (Na$_2$SO$_4$), filtered, concentrated, and purified by flash chromatography to give diol 2f as a pink solid (2.053 g, 93%): mp 210–213° C.; IR (KBr) 3340, 1752 cm$^{-1}$; $^1$H NMR (CD$_3$CN) δ5.78 (s, 1H), 3.94 (d, J=12.9 Hz, 1H), 3.83 (m, 1H), 3.78–3.69 (m, 3H), 3.64 (d, J=10.5 Hz, 1H), 3.29–3.23 (m, 3H), 0.87 (s, 9H), 0.15 (s, 3H), 0.13 (s, 3H); $^{13}$C NMR (CD$_3$CN) δ157.9, 106.4, 73.1, 71.1, 70.1, 66.4, 49.7, 26.3, 19.0, −3.2, −5.1. Anal. Calcd for C$_{13}$H$_{25}$NO$_6$Si: C, 48.88; H, 7.89; N, 4.38. Found: C, 48.79; H, 7.65; N, 4.45.

To a solution of 2f (0.638 g, 2.0 mmol) in CH$_2$Cl$_2$ (5 mL) were added TsOH (0.038 g, 0.2 mmol) and petanone (0.516 g, 6.0 mmol). Upon stirring at rt to the completion as judged by TLC (about 24 h), the reaction mixture was diluted with EtOAc, washed with water and brine, dried (Na$_2$SO$_4$), filtered, concentrated, and purified by flash chromatography to give compound 2g as a white solid (0.51 g, 66%): mp 158.5–159.5° C.; [α]$^{20}_D$=−84.1 (c 1.68, CHCl$_3$); IR (KBr) 3333, 1770 cm$^{-1}$; $^1$H NMR δ6.06 (s, 1H), 4.28–4.04 (m, 4H), 3.68 (d, J=6.0 Hz, 1H), 3.67 (d, J=9.0 Hz, 1H), 3.40 (d, J=9.0 Hz, 1H), 1.82–1.66 (m, 2H), 1.62 (q, J=7.5 Hz, 2H), 0.97 (t, J=7.5 Hz, 3H), 0.89 (t, J=7.5 Hz, 3H), 0.88 (s, 9H), 0.19 (s, 3H), 0.10 (s, 3H); $^{13}$C NMR δ158.0, 113.6, 104.9, 76.8, 73.8, 72.9, 62.3, 49.1, 30.5, 28.4, 26.0, 18.3, 8.93, 8.87, −3.7, −5.2. Anal. Calcd for C$_{18}$H$_{33}$NO$_6$Si: C, 55.79; H, 8.58; N, 3.61. Found: C, 55.66; H, 8.49; N, 3.79.

Compound 2h was prepared in a way similar to 2d (where R is Boc): white solid (93%); mp 102–104° C.; [α]$^{20}_D$=−59.1 (c 1.16, CHCl$_3$); IR (KBr) 1807, 1724 cm$^{-1}$; $^1$H NMR δ4.30–4.18 (m, 3H), 4.08 (d, J=12.9 Hz, 1H), 3.94 (d, J=10.5 Hz, 1H), 3.69 (d, J=10.5 Hz, 1H), 3.68 (d, J=6.6 Hz, 1H), 1.82–1.65 (m, 2H), 1.62 (q, J=7.5 Hz, 2H), 1.52 (s, 9H), 0.98 (t, J=7.5 Hz, 3H), 0.89 (t, J=7.5 Hz, 3H), 0.86 (s, 9H), 0.19 (s, 3H), 0.12 (s, 3H); $^{13}$C NMR δ150.3, 148.9, 113.7, 101.1, 84.1, 76.7, 74.1, 72.7, 62.7, 52.0, 30.5, 28.4, 28.2, 25.9, 18.2, 8.9, −3.7, −5.3. Anal. Calcd for C$_{23}$H$_{41}$NO$_8$Si: C, 56.65; H, 8.47; N, 2.87.
Found: C, 56.62; H, 8.24; N, 2.87.

TBS ether 2h (0.596 g, 1.224 mmol) was desilylated with Et$_3$N.3HF (0.986 g, 6.12 mmol) in a way similar to 2d (where R is Boc) to give the alcohol as a colorless oil (0.451 g, 99%) (about 4 days): [α]$^{20}_D$=−92.1 (c 0.70, CHCl$_3$); IR (KBr) 3478, 1817, 1728 cm$^{-1}$; $^1$H NMR δ4.26–4.11 (m, 3H), 4.06 (d, J=10.8 Hz, 1H), 3.99 (d, J=13.2 Hz, 1H), 3.84 (s, 1H, OH), 3.68 (d, J=6.6 Hz, 1H), 3.63 (d, J=10.8 Hz, 1H), 1.64 (q, J=7.5 Hz, 2H), 1.54 (q, J=7.5 Hz, 2H), 1.42 (s, 9H), 0.86 (t, J=7.5 Hz, 3H), 0.80 (t, J=7.2 Hz, 3H); $^{13}$C NMR δ150.5, 148.7, 113.6, 101.1, 84.0, 75.8, 72.6, 70.9, 62.2, 51.5, 30.0, 28.5, 27.9, 8.6, 8.5. Anal. Calcd for C$_{17}$H$_{27}$NO$_8$: C, 54.68; H, 7.29; N, 3.75. Found: C, 54.48; H, 7.18; N, 3.91.

The above alcohol (0.39 g, 1.05 mmol) was oxidized with PDC to give ketone IVn as a colorless oil (0.361 g, 93%): [α]$^{20}_D$=−25.7 (c 2.37, CHCl$_3$): IR (KBr) 3454 (hydrate), 1833, 1754, 1732 cm$^{-1}$; $^1$H NMR δ4.73 (d, J=6.0 Hz, 1H), 4.63 (dd, J=6.0, 1.8 Hz, 1H), 4.51 (d, J=11.2 Hz, 1H), 4.46 (dd, J=13.8, 1.8 Hz, 1H), 4.23 (d, J=13.8 Hz, 1H), 3.70 (d, J=11.2 Hz, 1H), 1.70–1.59 (m, 4H), 1.53 (s, 9H), 0.94–0.87 (m, 6H); $^{13}$C NMR δ194.9, 148.8, 148.4, 115.5, 98.7, 84.9, 76.8, 75.0, 61.7, 48.8, 29.8, 29.1, 28.1, 8.7, 8.4. Anal. Calcd for C$_{17}$H$_{25}$NO$_8$: C, 54.98; H, 6.79; N, 3.77. Found: C, 55.06; H, 6.91; N, 3.71.

HRMS Calcd for C$_{17}$H$_{26}$NO$_8$ (M$^+$+1): 372.1658. Found: 372.1662

Preparation of Ketone IVo

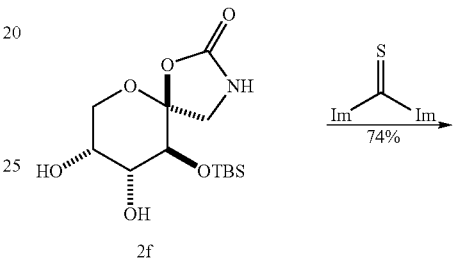

2f

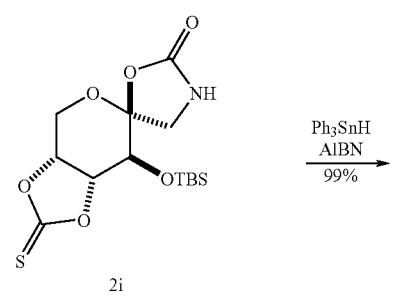

2i

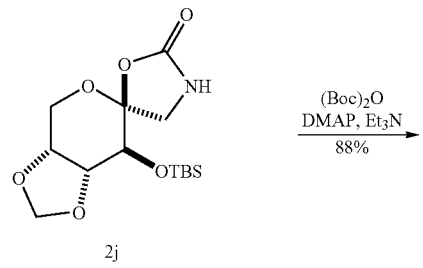

2j

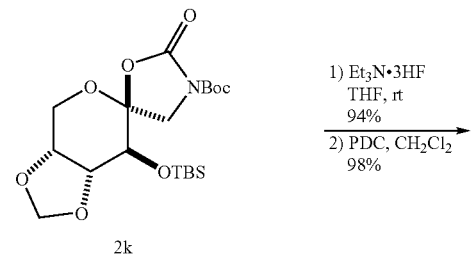

2k

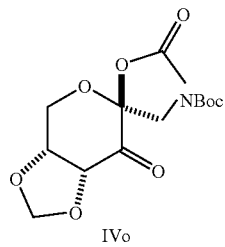

IVo

A mixture of thiocarbonyldiimidazole (1.12 g, 6.3 mmol) and diol 2f (1.826 g, 5.724 mmol) in toluene (30 mL) was heated at reflux for 1 h. Upon cooling, the reaction mixture was washed with water, the brine, dried (Na$_2$SO$_4$), filtered, concentrated, and purified by flash chromatography to give 2i as a white solid (1.523 g, 74%): mp 219–222° C.; [α]$^{20}$$_D$=−102.5 (c 0.49, CHCl$_3$); $^1$H NMR δ5.95 (s, 1H), 5.02–4.90 (m, 2H), 4.33 (s, 2H), 3.79 (d, J=6.0 Hz, 1H), 3.73 (d, J=9.6 Hz, 1H), 3.25 (d, J=9.6 Hz, 1H), 0.90 (s, 9H), 0.24 (s, 3H), 0.17 (s, 3H); $^{13}$C NMR δ190.1, 156.9, 103.6, 82.2, 79.5, 71.4, 60.2, 48.6, 25.8, 18.3, −3.9, −5.1. Anal. Calcd for 6SSi: C, 46.52; H, 6.41; N, 3.87. Found: C, 46.70; H, 6.39; N, 4.03.

Compound 2i (0.5 g, 1.385 mmol), Ph$_3$SnH (0.972 g, 2.77 mmol), and AIBN (0.014 g, 0.085 mmol) were dissolved in anhydrous toluene (35 mL). Upon stirring at reflux to the completion as judged by TLC, the reaction mixture was concentrated and purified by flash chromatography to give 2j as a white solid (0.457 g, 99%): mp 179–182° C.; [α]$^{20}$$_D$=−95.5 (c 1.17, CHCl$_3$); IR (KBr) 3295, 1767 cm$^{-1}$; $^1$H NMR δ6.27 (s, 1H), 5.18 (s, 1H), 5.00 (s, 1H), 4.31–4.25 (m, 2H), 4.16 (d, J=13.8 Hz, 1H), 4.01 (dd, J=5.4, 1.8 Hz, 1H), 3.69 (d, J=9.3 Hz, 1H), 3.60 (d, J=7.2 Hz, 1H), 3.39 (d, J=9.3 Hz, 1H), 0.87 (s, 9H), 0.17 (s, 3H), 0.09 (s, 3H); $^{13}$C NMR δ158.0, 104.9, 94.8, 76.3, 74.4, 71.5, 61.6, 48.8, 25.9, 18.3, −3.8, −5.2. Anal. Calcd for C$_{14}$H$_{25}$NO$_6$Si: C, 50.73; H, 7.60; N, 4.23. Found: C, 50.86; H, 7.56; N, 4.22.

Compound 2k was prepared in a way similar to 2d (where R is Boc): white solid (0.522 g, 88%); mp 119.0–120.5° C.; [α]$^{20}$$_D$=−65.0 (c 1.13, CHCl$_3$); IR (KBr) 1827, 1807, 1726 cm$^{-1}$; $^1$H NMR δ5.20 (s, 1H), 5.03 (s, 1H), 4.31–4.24 (m, 3H), 4.04 (m, 1H), 3.99 (d, J=10.8 Hz, 1H), 3.72 (d, J=10.8 Hz, 1H), 3.63 (d, J=7.2 Hz, 1H), 1.54 (s, 9H), 0.88 (s, 9H), 0.20 (s, 3H), 0.13 (s, 3H); $^{13}$C NMR δ150.2, 148.8, 101.1, 94.8, 84.2, 76.0, 74.2, 71.8, 62.0, 51.7, 28.2, 25.9, 18.2, −3.9, −5.4. Anal. Calcd for C$_{19}$H$_{35}$NO$_8$Si: C, 52.88; H, 7.71; N, 3.25. Found: C, 52.92; H, 7.60; N, 3.40.

TBS ether 2k (0.522 g, 1.21 mmol) was desilylated with Et$_3$N.3HF (0.975 g, 6.06 mmol) in a way similar to 2d (where R is Boc) to give the alcohol as a colorless oil (0.363 g, 94%) (about 4 days): [α]$^{20}$$_D$=−115.7 (c 1.28, CHCl$_3$); IR (KBr) 3468, 1812, 1726 cm$^{-1}$; $^1$H NMR δ5.21 (s, 1H), 4.99 (s, 1H), 4.32 (dd, J=7.5, 5.4 Hz, 1H), 4.24 (dd, J=13.5, 2.0 Hz, 1H), 4.18 (d, J=13.5 Hz, 1H), 4.14 (d, J=10.8 Hz, 1H), 4.04 (dd, J=5.7, 2.0 Hz, 1H), 3.72 (d, J=10.8 Hz, 1H), 3.65 (dd, J=7.5, 7.2 Hz, 1H), 3.41 (d, J=7.2 Hz, 1H), 1.51 (s, 9H); $^{13}$C NMR δ150.6, 148.9, 101.1, 95.0, 84.5, 75.7, 74.2, 69.5, 61.6, 51.3, 28.1. Anal. Calcd for C$_{13}$H$_{19}$NO$_8$: C, 49.21; H, 6.04; N, 4.41. Found: C, 49.26; 1, 5.96; N, 4.54.

The above alcohol (0.309 g, 0.974 mmol) was oxidized with PDC to give ketone IVo as a colorless oil (0.30 g, 98%): [α]$^{20}$$_D$=−35.6 (c 1.22, CHCl$_3$); IR (KBr) 3453, 1821, 1757, 1729 cm$^{-1}$; $^1$H NMR δ5.13 (s, 1H), 4.99 (s, 1H), 4.83 (d,J=5.4 Hz, 1H), 4.52–4.42 (m, 3H), 4.26 (d, J=13.5 Hz, 1H), 3.67 (d, J=11.7 Hz, 1H), 1.49 (s, 9H); $^{13}$C NMR δ193.6, 148.7, 148.3, 98.7, 95.8, 84.9, 78.4, 74.6, 61.1, 48.4, 28.0. Anal. Calcd for C$_{13}$H$_{17}$NO$_8$: C, 49.52; H, 5.43; N, 4.44. Found: C, 49.37; H, 5.60; N, 4.31. HRMS Calcd for C$_{13}$H$_{18}$NO$_8$(M$^+$+1): 316.1032. Found: 316.1040.

Preparation of Ketone IVp

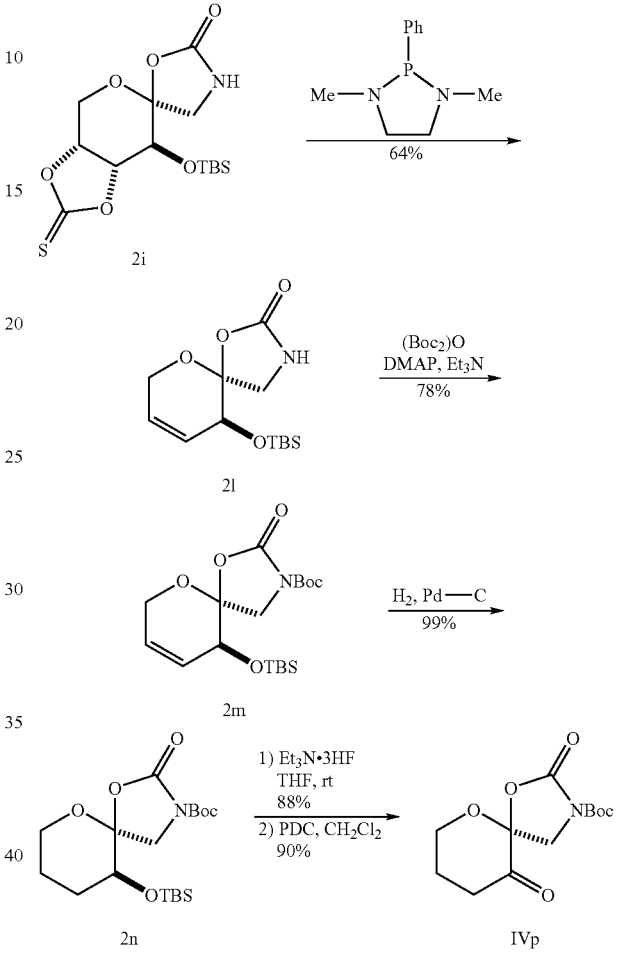

A suspension of thiocarbonate 2i (0.565 g, 1.566 mmol) in 1,3-dimethyl-2-phenyl-1,3,2-diazaphospholidine (0.911 g, 4.698 mmol) was stirred under N$_2$ at 40° C. for 20 h. Upon cooling, the mixture was purified by flash chromatography to give olefin 2l as a colorless oil (0.287 g, 64%): [α]$^{20}$$_D$=+9.63 (c 1.6, CHCl$_3$); IR (KBr) 3281, 1763 cm$^{-1}$; $^1$H NMR δ6.53 (s, 1H), 5.77 (d, J=10.5 Hz, 1H), 5.65 (d, J=10.5 Hz, 1H), 4.48 (dd, J=16.5, 1.2 Hz, 1H), 4.26 (s, 1H), 4.17 (dd, J=16.5, 1.2 Hz, 1H), 3.64 (d, J=9.6 Hz, 1H), 3.40 (d, J=9.6 Hz, 1H), 0.88 (s, 9H), 0.12 (s, 3H), 0.10 (s, 3H); $^{13}$C NMR δ158.5, 126.1, 125.5, 102.6, 67.5, 63.0, 49.3, 25.8, 18.1, −3.7, −4.6.

Compound 2m was prepared in a way similar to 2d (where R is Boc) colorless oil (78%); [α]$^{20}$$_D$=+19.0 (c 1.45, CHCl$_3$); IR (KBr) 1827, 1806, 1726 cm$^{-1}$; $^1$H NMR δ5.80–5.74 (m, 1H), 5.66–5.61 (m, 1H), 4.50–4.42 (m, 1H), 4.29–4.26 (m, 1H), 4.25–4.17 (m, 1H), 3.91 (d, J=10.5 Hz, 1H), 3.71 (d, J=10.5 Hz, 1H), 1.52 (s, 9H), 0.87 (s, 9H), 0.13 (s, 3H), 0.11 (s, 3H); $^{13}$C NMR δ150.5, 149.1, 125.7, 125.4, 98.8, 83.9, 67.8, 63.6, 52.2, 28.2, 25.8, 18.1, −3.6, −4.7.

A mixture 2m (0.303 g, 0.787 mmol) and 10% Pd—C (0.0303 g) in MeOH (10 mL) was stirred under H$_2$ for 24 h.

Upon filtration, the mixture was concentrated and purified by flash chromatography to give 2n as a colorless oil (0.301 g, 990): $[\alpha]^{20}_D$=−13.7 (c 1.31, CHCl$_3$); IR (KBr) 1824, 1799, 1727 cm$^{-1}$; $^1$H NMR δ3.90 (d, J=8.0 Hz, 1H), 3.93–3.86 (m, 1H), 3.72–3.68 (m, 1H), 3.61–3.57 (m, 1H), 3.57 (d, J=8.0 Hz, 1H), (m, 4H), 1.50 (s, 9H), 0.83 (s, 9H), 0.065 (s, 6H); $^{13}$C NMR δ8 150.9, 149.2, 101.4, 83.7, 71.6, 63.3, 52.3, 28.1, 28.0, 25.7, 24.4, 17.9, −3.5, −5.0. HRMS Calcd. for C$_{18}$H$_{34}$NO$_6$Si (M$^+$+1). 388.2155. Found: 388.2163.

TBS ether 2n (0.3 g, 0.775 mmol) was desilylated with Et$_3$N.3HF (0.625 g, 3.876 mmol) in a way similar to 2d (where R is Boc) to give the alcohol as a colorless oil (0.187 g, 88%) (about 4 days): $[\alpha]^{20}_D$=−71.2 (c 1.10, CHCl$_3$); IR (KBr) 3496, 1806, 1725 cm$^{-1}$; $^1$H NMR δ4.11 (d, J=8.1 Hz, 1H), 3.85 (td, J=8.4, 2.4 Hz, 1H), 3.70 (dd, J=8.4, 2.4 Hz, 1H), 3.63 (d, J=8.1 Hz, 1H), 3.52 (m, 1H), 2.59 (s, 1H), 2.06 (m, 1H), 1.82–1.71 (m, 3H), 1.50 (s, 9H); $^{13}$C NMR δ151.4, 149.1, 102.0, 84.1, 69.1, 62.9, 51.6, 28.15, 28.1, 24.7. HRMS Calcd. for C$_{12}$H$_{20}$NO$_6$ (M$^+$+1): 274.1291. Found: 274.1291.

The above alcohol (0.18 g, 0.659 mmol) was oxidized with PDC to give ketone IVp as a colorless oil (0.16 g, 90%): $[\alpha]^{20}_D$=+15.1 (c 1.24, CHCl$_3$); IR (KBr) 3475, 1827, 1736cm$^{-1}$; $^1$H NMR δ4.47(d, J=11.1 Hz, 1H),4.26(td, J=11.4, 3.6Hz, 1H), 3.89–3.83 (m, 1H), 3.49 (d, J=11.1 Hz, 1H), 2.86–2.75 (m, 1H), 2.61–2.55 (m, 1H), 2.27–2.08 (m, 2H), 1.45 (s, 9H); $^{13}$C NMR δ197.0, 149.1, 148.5, 99.0, 84.3, 62.7, 48.5, 35.8, 27.9, 27.0. HRMS Calcd. for C$_{12}$H$_{18}$NO$_6$ (M$^+$+1): 272.1134. Found: 272.1139.

Example 3

This example illustrates another method for synthesizing compounds of Formula IV where the substituent on the nitrogen atom is present in the starting amine compound used.

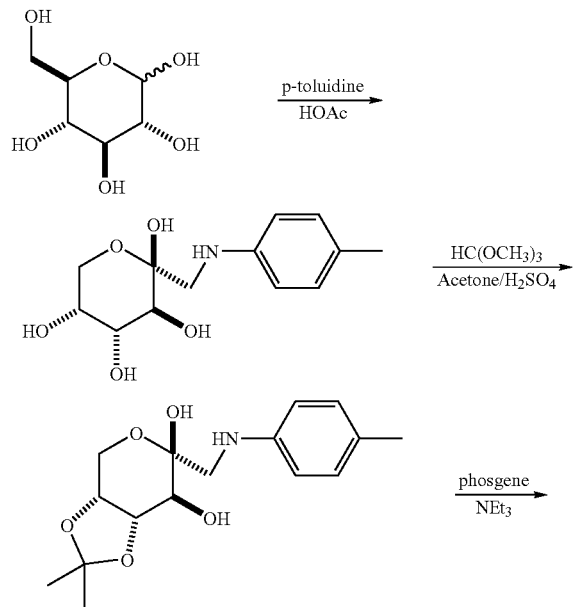

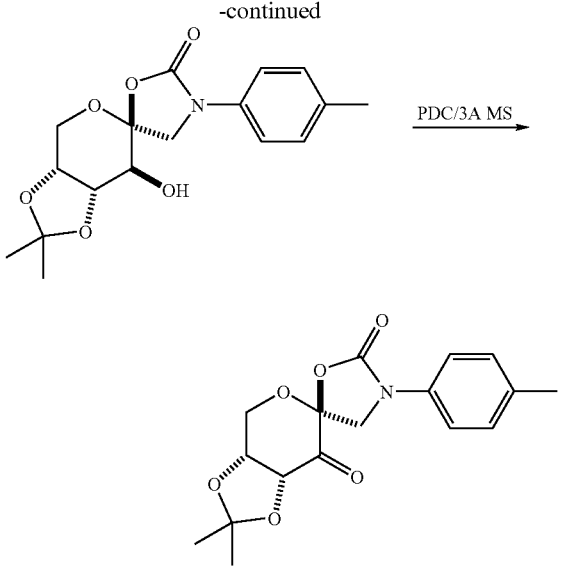

A mixture of D-Glucose (30.0 g, 0.167 mol), p-toluidine (24.0 g, 0.224 mol) and acetic acid (180 mg, 0.003 mol) in water (9 mL) was stirred at 100° C. for 1 hour. Then 300 mL of ethanol was added. The reaction mixture was put to freezer at −25° C. for 24 hours. The solid was filtered and washed with ether-ethanol (3/2, 150 mL) to give the product (26.4 g, 59% yield). mp. 152–153 C. $[\alpha]^{25}$=−23.0 (c 1.0, pyridine); $^1$H NMR δ6.87 (d, J=8.4 Hz, 2H), 6.55 (d, J=8.4 Hz, 2H), 5.50 (s, 1H), 4.89 (br, 1H), 4.45 (br, 2H), 3.85 (d, J=12.0 Hz, 1H), 3.68–3.40 (m, 4H), 3.00 (d, J=12.0 Hz, 1H), 2.20 (s, 3H); $^{13}$C NMR 146.9, 129.1, 124.2, 112.5, 98.2, 70.1, 69.3, 68.8, 63.4, 49.8, 20.2.

To a suspension of 1-p-toluidino-1-deoxy-D-fructose (19.37 g, 0.072 mol) and trimethyl orthoformate (16 mL, 0.146 mol) in acetone (1 L) at 0° C. was added H$_2$SO$_4$ (12 mL, 0.225 mol). The mixture was stirred at 0° C. for 2 hours, then quenched by NH$_3$.H$_2$O (~60 mL). The salt was filtered, the filtration was concentrated and residue was dissolved in dichloromethane, dried over Na$_2$SO$_4$, filtered and concentrated to about 50 mL. To this solution was added 150 mL of refluxing hexane. After standing at rt for 1 hour and 2 hours at −25° C., the solid was filtered and washed with cold hexane to give the product (19.44 g, 87% yield). mp. 39–41° C.; $[\alpha]^{25}$=−138 (c 0.5, CHCl$_3$); $^1$H NMR 7.01 (m, 2H), 6.71 (m, 2H), 4.23 (m, 2H), 4.17 (dd, J=13.5, 2.4 Hz, 1H), 4.00 (d, J=13.5 Hz, 1H), 3.61 (d, J=13.2 Hz, 1H), 3.59 (d, J=6.0 Hz, 1H), 3.21 (d, J=13.2 Hz, 1H), 2.25 (s, 3H), 1.56 (s, 3H), 1.39 (s, 3H); $^{13}$C NMR 145.6, 130.0, 128.7, 114.8, 109.4, 96.5, 77.4, 73.7, 72.1, 59.6, 50.8, 28.3, 26.4, 20.6; IR 3420 cm$^{-1}$.

To a solution of the above alcohol (7.72 g, 0.025 mol) and triethyl amine (10 mL, 0.072 mol) in dichloromethane at 0° C. was added dropwise phosgene in toluene (16.5 mL, 0.031 mol) over 30 min. The mixture was then stirred at 0° C. for 6 hours, quenched with 1 M NaOH (60 mL), and stirred for 5 min. The layers were separated, and the aqueous layer was extracted with dichloromethane. The combined organic phase was washed with 1 M HCl, saturated NaHCO$_3$, brine, dried, concentrated, dissolved in 100 mL of methanol. To this solution was added solid K$_2$CO$_3$ (3.45 g, 0.025 mol) and stirred at rt for 30 min. The solvent was removed under reduced pressure, the residue was dissolved CH$_2$Cl$_2$, washed with water, dried, concentrated to 30 mL. Then refluxing hexane (90 mL) was added. After standing at rt for 1 hour and 1 hour at −25° C., the solid was filtered and washed with cold hexane to give the product (7.0 g, 84% yield). mp: 170–172° C.; $[\alpha]^{25}=-93.0$ (c 0.43, CHCl$_3$); $^1$H NMR 7.37 (m, 2H), 7.20 (m, 2H), 4.3 (m, 4H), 4.2 (d, J=13.5 Hz, 1H), 3,78 (d, J=13.5 Hz, 1H), 3.10 (br, 1H), 2.32 (s, 3H), 1.57 (s, 3H), 1.40 (s, 3H); $^{13}$C NMR 152.7, 135.6, 134.3, 129.3, 118.2, 118.2, 110.0, 101.0, 76.6, 73.3, 71.6, 62.0, 53.4, 28.3, 26.3, 21.1; IR 3420 cm$^{-1}$.

To a solution of the above alcohol (6.70 g, 0.02 mol) in CH$_2$Cl$_2$ (100 mL) was added freshly grounded 3 Å molecular sieves (18.0 g), PDC (11.28 g, 0.03 mol) and 3 drops oof acetic acid. After stirred at rt overnight, the mixture was passed through a pad of celite, washed with ether, then passed through a short column of silica gel, washed with ether. The ether was concentrated and the residue was dissolved in 15 mL of CH$_2$Cl$_2$. Then refluxing hexane (60 mL) was added. After standing at rt for 3 hours and 2 hours in freezer, the solid part was filtered to give 4.20 g of the product. The filtrate was concentrated and purified on silica gel with hexane-ethyl acetate (1:1) to give additional 0.6 g of the product. The yield was 72%. mp. 149–150° C.; $[\alpha]^{25}=-41.4$ (c 0.34, CHCl$_3$); $^1$H NMR 7.39 (m, 2H), 7.18 (m, 2H), 4.87 (d, J=5.7 Hz, 1H), 4.73 (d, J=10.8 Hz, 1H), 4.63 (m, 2H), 4.25 (dd, J=14.4, 1.5 Hz, 1H), 3.74 (d, J=10.8 Hz, 1H), 2.33 (s, 3H), 1.48 (s, 3H), 1.43 (s, 3H); $^{13}$C NMR 195.0, 151.7, 134.8, 134.6, 129.7, 118.8, 111.1, 99.2, 77.6, 75.6, 61.0, 50.0, 27.3, 26.1, 21.0; IR 1772 cm$^{-1}$.

Example 4

This example illustrates the ability of Compounds of Formula I to asymmetrically epoxidize a variety of olefins.

Representative Asymmetric Epoxidation Procedure

To a solution of cis-β-methyl styrene (0.059 g, 0.5 mmol) and ketone IVd (0.026 g, 0.075 mmol) in DME-DMM (3:1, v/v) (7.5 mL) were added buffer (0.2 M K$_2$CO$_3$—AcOH in 4×10$^{-4}$ M aqueous EDTA, buffer pH=8.0) (5 mL) and Bu$_4$NHSO$_4$ (0.0075 g, 0.02 mmol) with stirring. After the mixture was cooled to about −10° C. (bath temperature) via a NaCl-ice bath, a solution of Oxone® (0.212 M in 4×10$^{-4}$ M aqueous EDTA, 4.2 mL) (0.548 g, 0.89 mmol) and K$_2$CO$_3$ (0.479 M in 4×10$^{-4}$ M aqueous EDTA, 4.2 mL) (0.278 g, 2.01 mmol) were added dropwise separately over a period of 3.5 h via a syringe pump. The reaction was then quenched with the addition of pentane and extracted with pentane. The combined organic layers were washed with brine, dried (Na$_2$SO$_4$), filtered, concentrated, and purified by flash chromatography (the silica gel was buffered with 1% Et$_3$N in pentane; pentane-ether (1/0 to 50/1 was used as eluent) to give cis-β-methylstyrene oxide as a colorless liquid (0.58 g, 87% yield, 91% ee).

Some of the epoxidation studies using ketones of Formulas IV and XII as catalysts are shown in Tables 2–6 below.

TABLE 2

Asymmetric Epoxidation of Olefins Catalyzed by Ketones of Formula XII

| Entry Substrate | Ketone (eq.) | Conv. (%) | Yield (%) | ee (%) |
|---|---|---|---|---|
|  | XIIa (0.05)<br>XIIb (0.05)<br>XIIc (0.05)<br>XIIe (0.05) | 86<br>99<br>99<br> | <br><br><br>99 | 72<br>83<br>82<br>88 |
|  | XIIa (0.05)<br>XIIb (0.05)<br>XIIc (0.05) | 27<br>71<br>95 | | 98<br>97<br>98 |
|  | XIIc (0.05)<br>XIIe (0.05) | | 85<br>89 | 87<br>88 |
|  | XIIb (0.05)<br>XIIc (0.05)<br>XIIe (0.05) | 84<br>82<br> | 69<br>61<br>99 | 88<br>88<br>93 |
|  | XIIe (0.05) | | 77 | 92 |
|  | XIIb (0.05)<br>XIIc (0.02)<br>XIIe (0.02) | 99<br>94<br> | <br><br>74 | 96<br>89<br>88 |
|  | XIIb (0.05)<br>XIIc (0.02)<br>XIIe (0.05) | 89<br>73<br> | 85<br><br>93 | 92<br>92<br>91 |

TABLE 3

Asymmetric Epoxidation of cis-olefins Catalyzed by Ketone IVd[a]

| Entry | Substrate | Yield (%)[b] | ee (%) | Configuration |
|---|---|---|---|---|
| 1[c] | 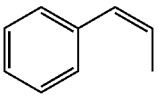 | 87 | 91[i] | (−)-(1R,2S)[n,15a,b] |
| 2[c] | 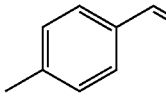 | 76[h] | 92[i] | (1R,2S)[o,15c] |

TABLE 3-continued
Asymmetric Epoxidation of cis-olefins Catalyzed by Ketone IVd[a]
| Entry | Substrate | Yield (%)[b] | ee (%) | Configuration |
|---|---|---|---|---|
| 3[c] | 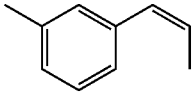 | 79[h] | 88[i] | (1R,2S)[o] |
| 4[c] | 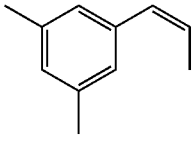 | 58[h] | 93[i] | ND |
| 5[c] | 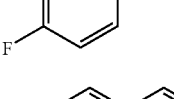 | 74[h] | 92[i] | (1R,2S)[o] |
| 6[d] | 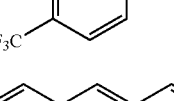 | 63[h] | 90[i] | (1R,2S)[o] |
| 7[c] | 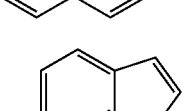 | 91 | 92[i] | (−)-(1R,2S)[p] |
| 8[e] | 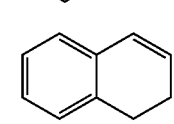 | 88 | 83[k] | (−)-(1R,2S)[n,15d] |
| 9[c] | 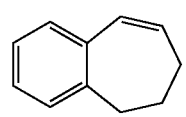 | 88 | 84[k] | (+)-(1R,2S)[n,15d,10d] |
| 10[e] | 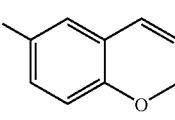 | 77 | 91[l] | (−)-(5R,6S)[n,15e,f] |
| 11[f] |  | 61 | 91[m] | (+)-(3R,4R)[n,15g,h] |
| 12[g] | 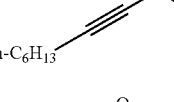 | 82 | 91[m] | (−)-(2S,3R)[q,10a,d] |
| 13[d] | 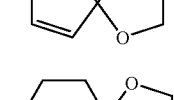 | 77 | 87[m] | (−)-(2S,3R)[q] |
| 14[d] | 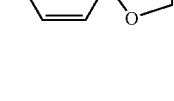 | 47 | 96[i] | (+) |
| 15[d] |  | 61 | 97[i] | (+)[15i] |

TABLE 3-continued

Asymmetric Epoxidation of cis-olefins Catalyzed by Ketone IVd[a]

| Entry | Substrate | Yield (%)[b] | ee (%) | Configuration |
|---|---|---|---|---|
| 16[d] | (dioxolane-fused cycloheptene) | 88 | 94[i] | (+) |

[a]All reactions were carried out with olefin (0.5 mmol), ketone (0.075–0.15 mmol), Oxone (0.89 mmol), and $K_2CO_3$ (2.01 mmol) in DME/DMM (3:1, v/v) (7.5 mL) and buffer (0.2 M $K_2CO_3$—AcOH, pH 8.0) (5 mL) at −10 or 0° C. The reactions were stopped after 3.5 h.
[b]The epoxides were purified by flash chromatography and gave satisfactory spectroscopic characterization.
[c]With 0.075 mmol ketone at −10° C.
[d]With 0.15 mmol ketone at 0° C.
[e]With 0.10 mmol ketone at −10° C.
[f]With 0.075 mmol ketone at 0° C.
[g]With 0.15 mmol ketone at −10° C.
[h]The olefin substrate contains a mixture of cis- and trans- isomers. The yield is for the mixture of cis- and trans-epoxides.
[i]Enantioselectivity was determined by chiral GC (Chiraldex G-TA).
[j]Enantioselectivity was determined by chiral HPLC (Chiralcel OJ).
[k]Enantioselectivity was determined by chiral HPLC (Chiralcel OB).
[l]Enantioselectivity was determined by chiral HPLC (Chiralpak AD).
[m]Enantioselectivity was determined by chiral HPLC (Chiralcel OD).
[n]The absolute configurations were determined by comparing the measured optical rotations with the reported ones.
[o]The epoxide was reduced to the benzylic alcohol with $LiAlH_4$, the absolute configuration was determined by comparing the measured optical rotation of the alcohol with the reported one.
[p]The epoxide was reduced to 1-(2-naphthyl)propanol with $LiAlH_4$, the absolute configuration was determined by comparing the measured optical rotation of the alcohol with the reported one.
[q]The epoxide was reduced with $LiAlH_4$ to the corresponding homopropargyl alcohol, the absolute configuration was determined by a correlation of the resulting alcohol with a prepared authentic sample by a different route.

TABLE 4

Asymmetric Epoxidation of Terminal Olefins Catalyzed by Ketone IVd[a]

| entry | substrate | yield (%)[b] | ee (%) | configuration[i] |
|---|---|---|---|---|
| 1[c] | styrene | 92 | 81[f] | (−)-(R)[17a] |
| 2[d] | 2-chlorostyrene | 61 | 81[f] | (−)-(R)[17a] |
| 3[d] | 3-chlorostyrene | 74 | 83[f] | (−)-(R)[17a] |
| 4[d] | 4-chlorostyrene | 90 | 85[f] | (−)-(R)[17a] |
| 5[d] | 2-fluorostyrene | 87 | 82[f] | (−)-[17b] |
| 6[d] | 3-fluorostyrene | 93 | 81[f] | (−)[17c] |
| 7[d] | 4-fluorostyrene | 94 | 81[f] | (−)-(R)[17d] |
| 8[e] | 3-nitrostyrene | 88 | 74[f] | (−)[4] |
| 9[e] | 2-vinylnaphthalene | 86 | 84[g] | (−)-(R)[17e] |
| 10[d] | vinylcyclohexane | 93 | 71[f] | ND[17f,g] |

TABLE 4-continued

Asymmetric Epoxidation of Terminal Olefins Catalyzed by Ketone IVd[a]

| entry | substrate | yield (%)[b] | ee (%) | configuration.[i] |
|---|---|---|---|---|
| 11[d] | (α-methylstyrene) | 88 | 30[h] | (+)-(S)[17a] |
| 12[d] | (2-phenyl-3-methyl-1-butene) | 87 | 58[f] | (+)[17h] |

[a]All reactions were carried out with olefin (0.5 mmol), ketone (0.075–0.15 mmol), Oxone (0.89 mmol), and $K_2CO_3$ (2.01 mmol) in DME/DMM (3:1, v/v) (7.5 mL) and buffer (0.2 M $K_2CO_3$—AcOH, pH 8.0) (5 mL) at −10 or 0° C. The reactions were stopped after 3.5 h.
[b]The epoxides were purified by flash chromatography and gave satisfactory spectroscopic characterization.
[c]With 0.075 mmol ketone at −10° C.
[d]With 0.15 mmol ketone at −10° C.
[e]With 0.15 mmol ketone at 0° C.
[f]Enantioselectivity was determined by chiral GC (Chiraldex G-TA).
[g]Enantioselectivity was determined by chiral HPLC (Chiralcel OJ).
[h]Enantioselectivity was determined by chiral HPLC (Chiralcel OD).
[i]The absolute configurations were determined by comparing the measured optical rotations with the reported ones.

TABLE 5

Asymmetric epoxidation of trans- and trisubstituted olefins catalyzed by ketone IVd[a]

| Entry | Substrate | Yield (%)[b] | ee (%) | Configuration |
|---|---|---|---|---|
| 1[c] | trans-stilbene | 65 | 94[e] | (+)-(R,R)[g,18,7c] |
| 2[d] | trans-β-methylstyrene | 91 | 77[f] | (+)-(R,R)[g,15a,7c] |
| 3[d] | 2-methyl-1-phenylpropene | 78 | 95[f] | (+)[7c] |
| 4[d] | 1-phenylcyclohexene | 68 | 42[f] | (−)-(S,S)[g,7c] |
| 5[d] | 4-phenyl-1,2-dihydronaphthalene | 55 | 80[e] | (+)[7c] |

[a]All reactions were carried out with olefin (0.5 mmol), ketone (0.075–0.15 mmol), Oxone (0.89 mmol), and $K_2CO_3$ (2.01 mmol) in DME/DMM (3:1, v/v) (7.5 mL) and buffer (0.2 M $K_2CO_3$—AcOH, pH 8.0) (5 mL) at −10 or 0° C. The reactions were stopped after 3.5 h.
[b]The epoxides were purified by flash chromatography and gave satisfactory spectroscopic characterization.
[c]With 0.15 mmol ketone at 0° C.
[d]With 0.075 mmol ketone at −10° C.
[e]Enantioselectivity was determined by chiral HPLC (Chiralcel OD).
[f]Enantioselectivity was determined by chiral GC (Chiraldex G-TA).
[g]The absolute configurations were determined by comparing the measured optical rotations with the reported ones.

TABLE 6

Asymmetric Epoxidation of Olefins Catalyzed by Ketones IVa–IVp and 17[a]

| entry | ketone | conv.(ee)[b] | conv.(ee)[c] | conv.(ee)[d] | conv.(ee)[e] | conv.(ee) |
|---|---|---|---|---|---|---|
| 1 | IVa | 100 (62) | 100 (59) | 100 (76) | 100 (79) | 100 (55) (R,R) |
| 2 | IVb | 100 (72) | 100 (79) | 100 (79) | 100 (92) | 100 (40) (R,R) |
| 3 | IVc | 100 (65) | 100 (70) | 100 (81) | 100 (90) | 100 (59) (R,R) |
| 4 | IVd | 100 (79) | 100 (87) | 100 (77) | 100 (94) | 100 (23) (S,S) |
| 5 | IVe | 100 (75) | 100 (89) | 100 (73) | 100 (94) | 100 (46) (S,S) |
| 6 | IVf | 88 (61) | 100 (59) | 97 (72) | 100 (69) | 100 (65) (R,R) |
| 7 | IVg | 87 (73) | 100 (87) | 100 (73) | 100 (95) | 100 (44) (S,S) |
| 8 | IVh | 99 (70) | 100 (78) | 100 (75) | 100 (89) | 100 (51) (R,R) |
| 9 | IVi | 94 (73) | 100 (86) | 85 (73) | 100 (95) | 100 (18) (S,S) |
| 10 | IVj | 100 (73) | 100 (87) | 100 (74) | 100 (93) | 100 (14) (S,S) |
| 11 | IVk | 100 (66) | 97 (78) | 100 (71) | 100 (90) | 100 (12) (R,R) |
| 12 | IVl | 100 (63) | 100 (74) | 100 (69) | 100 (88) | 100 (6) (R,R) |
| 13 | IVm | 100 (52) | 100 (47) | 100 (70) | 100 (54) | 100 (69) (R,R) |
| 14 | IVn | 100 (77) | 100 (80) | 100 (75) | 100 (91) | 100 (23) (S,S) |
| 15 | IVo | 100 (69) | 100 (79) | 100 (73) | 100 (93) | 100 (29) (S,S) |
| 16[f] | IVp | 100 (47) | 100 (39) | 100 (61) | 100 (78) | 100 (2) (R,R) |
| 17[g] | 17 | 49 (<1) | 91 (16)[h] | 83 (32) | 64 (3) | 66 (64) (R,R) |

[a]All reactions were carried out with olefin (1 equiv), ketone (0.15 equiv), $Bu_4NHSO_4$ (0.05 equiv), Oxone (1.6 equiv), and $K_2CO_3$ (4.2 equiv) in DME/DMM (3:1, v/v) and buffer (0.2 M $K_2CO_3$—AcOH, pH 8.0) at 0° C. The reactions were stopped after 3.5 h. Enantioselectivity was determined by chiral GC (Chiraldex G-TA). Compound 17 is of the formula:

TABLE 6-continued

Asymmetric Epoxidation of Olefins Catalyzed by Ketones IVa–IVp and 17[a]

| entry | ketone | Ph⟶ conv.(ee)[b] | Ph⟶Ph (cis) conv.(ee)[c] | Ph⟶Ph (trans) conv.(ee)[d] | Ph⟶Ph-Me conv.(ee)[e] | Ph-cyclohexenyl conv.(ee) |
|---|---|---|---|---|---|---|

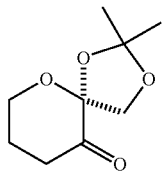

17

[b] The epoxide has the (R) configuration.
[c] The epoxide has the (1R,2S) configuration unless otherwise noted.
[d] The epoxide has the (R,R) configuration.
[e] The epoxide has the (R) configuration.
[f] 0.3 equiv ketone used.
[g] 1.0 equiv ketone used.
[h] The epoxide has the (1S,2R) configuration.

Representative physical characteristics of the epoxidation products are shown below:

(1R,2S)-cis-β-Methylstyrene oxide (Table 3, entry 1). Colorless oil; $[\alpha]^{20}_D$=−45.5 (c 0.67, CHCl$_3$).

(1R,2S)-1-(4-Methylphenyl)-1-propene oxide (Table 3, entry 2). Colorless oil; $^1$H NMR δ7.16 (m, 4H), 4.04 (d, J=4.2 Hz, 1H), 3.29–3.26 (m, 1H), 2.40 (s, 3H), 1.14 (D, J=5.1 Hz, 3H); $^{13}$C NMR δ128.8, 126.6, 57.7, 55.3, 21.4, 12.7.

(1R,2S)-1-(3-Methylphenyl)-1-propene oxide (Table 3, entry 3). Colorless oil; $^1$H NMR δ7.26–7.09 (m, 4H), 4.04 (d, J=4.2 Hz, 1H), 3.37–3.30 (m, 1H), 2.37 (s, 3H), 1.10 (D, J=5.7 Hz, 3H); $^{13}$C NMR δ137.7, 128.3, 128.0, 127.3, 123.7, 57.7, 55.3, 21.6, 12.8. HRMS Calcd. for C$_{10}$H$_{12}$O: 148.0888. Found: 148.0888.

(1R,2S)-1-(3,5-Dimethylphenyl)-1-propene oxide (Table 3, entry 4). Colorless oil; $^1$H NMR δ6.95–6.85 (m, 3H), 4.00 (d, J=4.2 Hz, 1H), 3.32 (qd, J=5.7, 4.2, 1H), 2.32 (s, 6H), 1.10 (d, J=5.7 Hz, 3H); $^{13}$C NMR δ129.2, 124.4, 57.7, 55.2, 21.5, 12.8. HRMS Calcd. for C$_{11}$H$_{14}$O: 162.1045. Found: 162.1042.

(1R,2S)-1-(4-Fluorophenyl)-1-propene oxide (Table 3, entry 5). Colorless oil; $^1$H NMR δ7.30–7.19 (m, 2H), 7.09–6.98 (m, 2H), 4.03 (d, J=4.2 Hz, 1H), 3.33 (qd, J=5.1, 4.2 Hz, 1H), 1.07 (d, J=5.1 Hz, 3H); $^{13}$C NMR δ128.3, 128.2, 115.2, 115.0, 57.2, 55.3, 12.7. Anal. Calcd C$_9$H$_9$FO: C, 71.04; H, 5.96. Found: C, 71.21; H, 5.90.

(1R,2S)-1-(4-Trifluoromethylphenyl)-1-propene oxide (Table 3, entry 6). Colorless oil; $^1$H NMR δ7.62 (d, J=8.1 Hz, 2H), 7.43 (d, J=8.1 Hz, 2H), 4.10 (d, J=4.2 Hz, 1H), 3.39 (m, 1H), 1.08 (d, J=5.4 Hz, 3H); $^{13}$C NMR δ127.0, 125.1, 57.2, 55.4, 12.7. Anal. Calcd C$_{10}$H$_9$F$_3$: C, 59.41; H, 4.49. Found: C, 59.19; H, 4.65.

(1R,2S)-1-(2-Naphthyl)-1-propene oxide (Table 3, entry 7). White solid; $[\alpha]^{20}_D$=−13.5 (c 1.31, CHCl$_3$); IR (KBr) 3051, 1511, 1341cm$^{-1}$; $^1$H NMR δ7.86–7.77 (m,4H), 7.50–7.44 (m, 3H), 4.23 (d, J=4.5 Hz, 1H), 3.43 (qd, J=5.4, 4.5 Hz, 1H), 1.12 (d, J=5.4 Hz, 3H); $^{13}$C NMR δ133.1, 132.9, 127.9, 127.8, 126.3, 125.9, 125.6, 124.6, 57.9, 55.6, 12.8. Anal. Calcd for C$_{13}$H$_{12}$O: C, 84.75; H, 6.57. Found: C, 84.60; H, 6.41.

(1R,2S)-Indene oxide (Table 3, entry 8). Colorless oil; $[\alpha]^{20}_D$=−38.3 (c 1.2, CHCl$_3$).

(1R,2S)-3,4-Dihydronaphthalene oxide (Table 3, entry 9). Colorless oil; $[\alpha]^{20}_D$=+133.2 (c 1.57, CHCl$_3$).

(5R,6S)-5,6-Epoxy-6,7,8,9-tetrahydro-5H-benzocycloheptene (Table 3, entry 10). Colorless oil; $[\alpha]^{20}_D$=−23.4 (c 0.82, CHCl$_3$).

(3R,4R)-6-Cyano-3,4-epoxy-2,2-dimethylchromene (Table 3, entry 11). White solid; $[\alpha]^{20}_D$=+62.7 (c 0.71, CHCl$_3$).

(2S,3R)-2-Methyl-3-(phenylethynyl)oxirane (Table 3, entry 12). Colorless oil; $[\alpha]^{20}_D$=−33.0 (c 0.98, CHCl$_3$).

(2S,3R)-2-Methyl-3-(1-octynyl)oxirane (Table 3. entry 13). Colorless oil; $[\alpha]^{20}_D$=−31.4 (c 0.29, CHCl$_3$); IR (KBr) 2215, 1347 cm$^{-1}$; $^1$H NMR δ3.45 (dt, J=3.9, 1.8 Hz, 1H), 3.16 (qd, J=5.1, 3.9 Hz, 1H), 2.70 (td, J=7.2, 1.8 Hz, 2H), 1.63–1.25 (m, 8H), 1.45 (d, J=5.1 Hz, 3H), 0.93 (t, J=6.9 Hz, 3H); $^{13}$C NMR δ100.1, 86.8, 54.1, 46.1, 31.5, 30.1, 28.6, 22.7, 19.0, 14.9, 14.3. Anal. Calcd for C$_{11}$H$_{18}$O: C, 79.46; H, 10.91. Found: C, 79.28; H, 10.95.

(+)-3,3-Ethylenedioxycyclopentene oxide (Table 3, entry 14). Colorless oil; $[\alpha]^{20}_D$=+12.7 (c 0.132, CHCl$_3$); IR (KBr) 1347, 1130 cm$^{-1}$; $^1$H NMR δ4.10–3.85 (m, 4H), 3.51 (m, 1H), 3.25 (d, J=3 Hz, 1H), 2.10 (m, 1H), 1.85–1.55 (m, 3H); $^{13}$C NMR δ114.8, 65.4, 65.0, 55.9, 55.7, 29.5, 25.2. Anal. Calcd for C$_7$H$_{10}$O$_3$: C, 59.14; H, 7.09. Found: C, 59.32; H, 7.18.

(+)-3,3-Ethylenedioxycyclohexene oxide (Table 3, entry 15). Colorless oil; $[\alpha]^{20}_D$=+9.7 (c 2.3, hexane).

(+)-3,3-Ethylenedioxycycloheptene oxide (Table 3, entry 16). Colorless oil; $[\alpha]^{20}_D$=+6.5 (c 0.71, CHCl$_3$); IR (KBr) 1147, 1087, 1061 cm$^{-1}$; $^1$H NMR δ4.10–3.86(m, 4H), 3.09 (td, J=5.3, 1.2 Hz, 1H), 2.95 (dd, J=4.5, 1.2 Hz, 1H), 2.28–2.21 (m, 1H), 1.95–1.43 (m, 6H), 1.30–1.21 (m, 1H); $^{13}$C NMR δ110.9, 65.1, 64.9, 59.4, 54.3, 34.9, 28.0, 23.7, 22.9. Anal. Calcd for C$_9$H$_{14}$O$_3$: C, 63.51; H, 8.29. Found: C, 63.65; H, 8.50.

(R)-(−)-Styrene oxide (Table 4, entry 1). Colorless oil; [α]$^{20}_D$=−19.2 (c 1.34, CHCl$_3$).
(R)-(−)-2-Chlorostyrene oxide (Table 4, entry 2). Colorless oil; [α]$^{20}_D$=−49.7 (c 0.7, CHCl$_3$).
(R)-(−)-3-Chlorostyrene oxide (Table 4, entry 3). Colorless oil; [α]$^{20}_D$=−10.3 (c 1.04, CHCl$_3$).
(R)-(−)-4-Chlorostyrene oxide (Table 4, entry 4). Colorless oil; [α]$^{20}_D$=−21.8 (c 0.83, CHCl$_3$).
(R)-(−)-2-Fluorostyrene oxide (Table 4, entry 5). Colorless oil; [α]$^{20}_D$=−13.2 (c 0.92, hexane)
(R)-(−)-3-Fluorostyrene oxide (Table 4, entry 6). Colorless oil; [α]$^{20}_D$=−3.24 (c 1.27, hexane)
(R)-(−)-4-Fluorostyrene oxide (Table 4, entry 7). Colorless oil; [α]$^{20}_D$=−14.0 (c 1.13, CHCl$_3$).
(−)-3-Nitrostyrene oxide (Table 4 entry 8). Colorless oil; [α]$^{20}_D$=−3.7 (c 0.46, CHCl$_3$).
(R)-(−)-2-Naphthyloxirane (Table 4, entry 9). White solid; [α]$^{20}_D$=−11.4 (c 0.67, CHCl$_3$).
Cyclohexyloxirane (Table 4, entry 10). Colorless oil.
(S)-(+)-α-Methylstyrene oxide (Table 4, entry 11). Colorless oil; [α]$^{20}_D$=+2.78 (c 1.1, CHCl$_3$).
(+)-α-Isopropylstyrene oxide (Table 4, entry 12). Colorless oil; [α]$^{20}_D$=+23.2 (c 0.6, hexane); $^1$H NMR δ7.44–7.30 (m, 5H), 3.05 (d, J=5.1 Hz, 1H), 2.77 (d, J=5.1 Hz, 1H), 2.21–2.07 (m, 1H), 1.02 (d, J=6.9 Hz, 3H), 1.00 (d, J=6.9 Hz, 3H); $^{13}$C NMR δ139.4, 128.0, 127.4, 127.3, 64.7, 53.4, 33.4, 18.8, 18.1.

As shown in Tables 2–6, surprising and unexpectedly it was found that ketones of Formula IV gave very high enantioselectivity for the epoxidation of cis- and terminal olefins. In addition, high conversions of olefins to epoxides were obtained with compounds of Formula XII even when only 2–5 mole % of the ketone (i.e., Compound of Formula XII) was used as a catalyst (see for example, Table 2).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A compound of the formula:

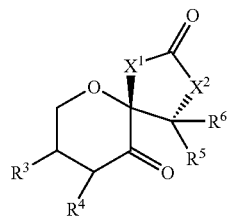

I wherein
each of $R^3$ and $R^4$ is independently hydrogen or —OR$^c$, where R$^c$ is a non-ring forming hydroxy protecting group, or $R^3$ and $R^4$ together with the carbon atoms to which they are attached form an optionally substituted heterocyclyl;
each of $R^5$ and $R^6$ is independently hydrogen or alkyl; and
one of $X^1$ and $X^2$ is O and the other is NR$^7$, where R$^7$ is hydrogen, alkyl, aryl, —(R$^8$)$_n$—C(=O)—R$^9$, or nitrogen protecting group,
where
n is 0 or 1;
R$^8$ is alkylene, and
R$^9$ is hydroxy, alkyl, alkoxy, aryl, aryloxy, or —NR$^a$R$^b$, where each of R$^a$ and R$^b$ is independently hydrogen or alkyl.

2. The compound according to claim 1, wherein the relative stereochemiswy of $R^3$ and $R^4$ is a cis-configuration.

3. The compound according to claim 1 of the formula:

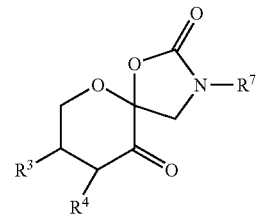

or a sterecisomer thereof,
wherein
$R^3$ $R^4$, and R$^7$ are those defined in claim 1.

4. The compound according to claim 3, wherein $R^3$ and $R^4$ together wit the carbon atoms to which they are attached form an optionally substituted heterocyclyl.

5. The compound according to claim 4 of the formula:

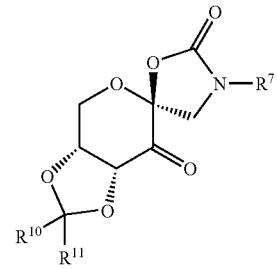

or a sterecisomer thereof,
wherein
R$^7$ is that defined in claim 1; and
each of R$^{10}$ and R$^{11}$ is independently selected from the group consisting of hydrogen, alkyl, aralkyl and aryl.

6. The compound according to claim 2, wherein $R^3$ and $R^4$ together with the carbon atoms to which they are attached form an optionally substituted nitrogen atom containing heterocyclyl.

7. The compound according to claim 6 of the formula:

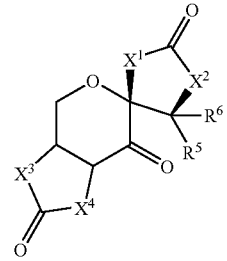

wherein
$R^1$, $R^2$, $R^5$, $R^6$, $X^1$, and $X^2$, are those defined in claim 1; and one of $X^3$ and $X^4$ is O and the other is $NR^7$, where $R^7$ is defined in claim 1.

8. A method for producing a spiro-bicyclic compound of the formula:

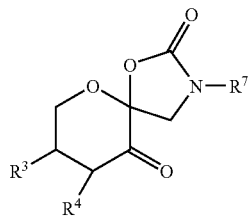

IA wherein
each of $R^3$ and $R^4$ is independently hydrogen or —$OR^c$, where $R^c$ is a non-ring forming hydroxy protecting group, or $R^3$ and $R^4$ together with the carbon atoms to which they are attached to form an optionally substituted heterocyclyl; and
$R^7$ is selected from the group consisting of hydrogen, alkyl, and, —$(R^8)_n$—C(=O)—$R^9$, and another nitrogen protecting group,
where
n is 0 or 1,
$R^8$ is alkylene, and
$R^9$ is hydroxy, alkyl, alkoxy, and, aryloxy and —$NR^aR^b$, where $R^a$ and $R^b$ is independently hydrogen or alkyl;
said method comprising:
(a) contacting a carbohydrate selected from glucose and fructose with an amine under condition sufficient to produce an amino tetrahydroxy carbohydrate;
(b) protecting two hydroxy groups by contacting the amino tetrahydroxy carbohydrate wit a hydroxy protecting group under conditions sufficient to produce a dihydroxy-protected amino dihydroxy carbohydrate;
(c) forming a heterocyclic moiety by contacting the dihydroxy-protected amino dihydroxy carbohydrate with an activated carbonate under conditions sufficient to produce a hydroxy spiro-bicyclic compound; and
(d) oxidizing the hydroxy group by contacting the hydroxy spiro-bicyclic compound with an oxidizing agent under conditions sufficient to produce the spiro-bicyche compound of Formula IA.

9. The method of claim 8, wherein the spiro-bicyclic compound is enantiomerically enriched chiral compound.

10. The method of claim 9, wherein the carbohydrate is glucose.

11. The method of claim 10, wherein the carbohydrate is D-glucose.

12. The method of claim 10, wherein the enantiomerically enriched spiro-bicyclic compound is of the formula:

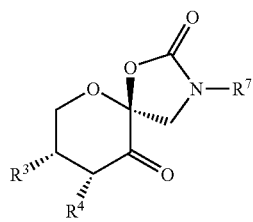

or stereoisomers thereof,
where $R^3$, $R^4$ and $R^7$ are those defined in claim 8.

13. The method of claim 12, wherein the enantiomerically enriched spiro-bicyclic compound is of the formula:

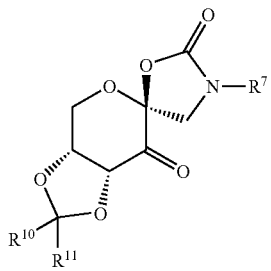

or a stereoisomers thereof,
wherein
$R^7$ is that defined in claim 8; and each of $R^{10}$ and $R^{11}$ is independently selected from the group consisting of hydrogen, alkyl, aralkyl and aryl.

14. The method of claim 8, wherein the activated carbonate is selected from the group consisting of phosgene, triphosgene and a haloformate.

15. The method of claim 8, wherein the amine is diaralkyl amine.

16. The method of claim 15 further comprising removing aralkyl groups from the amino nitrogen by contacting the dihydroxy-protected amino dihydroxy carbohydrate with hydrogen in the presence of a hydrogenation catalyst under conditions sufficient to produce a dihydroxy-protected free-amino carbohydrate prior to said heterocyclic moiety forming step (c).

17. A method for producing an epoxide from an olefin comprising admixing a ketone compound of claim 1, an olefin, and an oxidizing agent under conditions sufficient to produce the epoxide.

18. The method of claim 17, wherein the olefin comprises a chiral or a pro-chiral center.

19. The method of claim 18, wherein the ketone compound of claim 1 is an enantiomerically enriched chiral ketone compound.

20. The method of claim 19, wherein the epoxide is enariomerically enriched.

21. The method of claim 20, wherein the olefin is a cis-olefin or a terminal olefin.

22. The method of claim 19, wherein the enantiomerically enriched chiral ketone is of the formula:

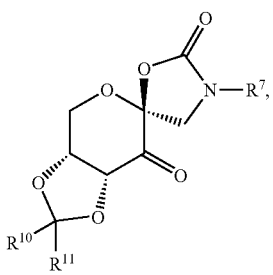

or a stereisomer thereof,
wherein
$R^7$ is that defined in claim 1; and
each of $R^{10}$ and $R^{11}$ is independently selected from the group consisting of hydrogen, alkyl, aralkyl and aryl.

23. The method of claim 17, wherein said oxidizing agent is selected from the group consisting of peracids, hydrogen peroxide, sodium hypochlorite, potassium peroxormonosulfate, sodium perborate and hypofluoride (HOF).

24. The method of claim 23, wherein said oxidizing agent is potassium peroxomonosulfate.

25. The method of claim 17, wherein said admixture further comprises a base.

26. The method of claim 17 further comprising maintaining pH of the admixture within the range of from about pH 5 to about pH 14, 27. The method of claim 17, wherein said asymmetric epoxide is produced in an enantiomeric excess of at least about 80% ee.

28. A method for stereoselecrively epoxidizing a cis-olefin or a terminal olefin comprising the steps of admixing a chiral ketone compound of claim 1, the cis- or the terminal olefin, and an oxidizing agent under conditions sufficient to produce an asymmetric epoxide in at least about 80% ee.

29. The method of claim 28, wherein said chiral ketone is of the formula:

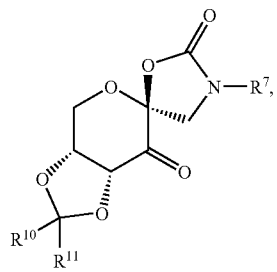

and a sterecisomer thereof,
wherein
$R^7$ is that defined in claim 1 each of $R^{10}$ and $R^{11}$ is independently selected from the group consisting of hydrogen, alkyl, aralkyl and aryl.

* * * * *

UNITED STATES PATENT AND TRADEMARK OFFICE
CERTIFICATE OF CORRECTION

PATENT NO. : 7,153,971 B2
APPLICATION NO. : 10/343302
DATED : December 26, 2006
INVENTOR(S) : Yian Shi It is certified that error appears in the above-identified patent and that said Letters Patent is hereby corrected as shown below:

Claim 1, Col. 60, line 11, delete "-NR$^3$R$^b$" and insert --"-NR$^a$R$^b$"--.
Claim 1, Col. 60, line 12, delete "R$^2$" and insert --"R$^a$"--.
Claim 2, Col. 60, line 15, delete "stereochemiswy" and insert --stereochemistry--.
Claim 3, Col. 60, line 27, delete "sterecisomer" and insert --stereoisomer--.
Claim 3, Col. 60, line 29, delet "R$^3$ R$^4$" and insert --R$^3$, R$^4$--.
Claim 4, Col. 60, line 31, delete "wit" and insert --with--.
Claim 5, Col. 60, line 47, delete "sterecisomer" and insert --stereoisomer--.
Claim 7, Col. 61, line 2, delete "R$^{1, R2}$," and insert --R$^1$, R$^2$,--.
Claim 8, Col. 61, line 22, delete "alkyl, and," and insert --alkyl, aryl,--.
Claim 8, Col. 61, line 27, delete "and, aryloxy and" and insert --aryl, aryloxy or--.
Claim 8, Col. 61, line 48, delete "spiro-bicyche" and insert --spiro-bicyclic--.
Claim 13, Col. 62, line 15, delete "stereoisomers" and insert --stereoisomer--.
Claim 20, Col. 62, line 43, delete "enariomerically" and insert --enantiomerically--.
Claim 22, Col. 62, line 59, delete "sterecisomer" and insert --stereoisomer--.
Claim 28, Col. 63, line 13, delete "stereoselecrively" and insert --stereoselectively--.
Claim 29, Col. 64, line 14, delete "sterecisomer" and insert --stereoisomer--.

Signed and Sealed this

Tenth Day of April, 2007

JON W. DUDAS
*Director of the United States Patent and Trademark Office*